United States Patent
Andersson et al.

(10) Patent No.: US 10,300,065 B2
(45) Date of Patent: May 28, 2019

(54) METHOD OF TREATING OR PREVENTION OF ATHEROTHROMBOTIC EVENTS IN PATIENTS WITH HISTORY OF MYOCARDIAL INFARCTION

(71) Applicants: ASTRAZENECA AB, Sodertalje (SE); THE UNIVERSITY OF SHEFFIELD, Sheffield (GB); SHEFFIELD TEACHING HOSPITALS NHS FOUNDATION TRUST, Sheffield (GB); Robert Storey, Sheffield (GB)

(72) Inventors: Lars Magnus Andersson, Mölndal (SE); Tomas Lars-Gunnar Andersson, Mölndal (SE); Olof Fredrik Bengtsson, Mölndal (SE); Hans Peter Held, Mölndal (SE); Garnet Edward Howells, Edinburgh (GB); Eva Christina Jensen, Mölndal (SE); Robert Storey, Sheffield (GB)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 15/546,626

(22) PCT Filed: Jan. 27, 2016

(86) PCT No.: PCT/IB2016/000275
§ 371 (c)(1),
(2) Date: Jul. 26, 2017

(87) PCT Pub. No.: WO2016/120729
PCT Pub. Date: Aug. 4, 2016

(65) Prior Publication Data
US 2018/0015089 A1 Jan. 18, 2018

Related U.S. Application Data

(60) Provisional application No. 62/108,453, filed on Jan. 27, 2015, provisional application No. 62/112,318, filed on Feb. 5, 2015, provisional application No. 62/117,871, filed on Feb. 18, 2015, provisional application No. 62/133,224, filed on Mar. 13, 2015, provisional application No. 62/133,327, filed on Mar. 14, 2015, provisional application No. 62/156,083, filed on May 1, 2015, provisional application No. 62/156,823, filed on May 4, 2015, provisional application No. 62/211,635, filed on Aug. 28, 2015.

(51) Int. Cl.
*A61K 31/519* (2006.01)
*A61K 31/60* (2006.01)
*A61K 31/609* (2006.01)
*A61K 31/616* (2006.01)
*A61K 9/20* (2006.01)

(52) U.S. Cl.
CPC .............. *A61K 31/519* (2013.01); *A61K 9/20* (2013.01); *A61K 31/60* (2013.01); *A61K 31/609* (2013.01); *A61K 31/616* (2013.01)

(58) Field of Classification Search
CPC .. A61K 2300/00; A61K 31/519; A61K 31/60; A61K 31/609; A61K 31/616; A61K 9/20
See application file for complete search history.

(56) References Cited

FOREIGN PATENT DOCUMENTS

WO    WO-2008024044 A1 *   2/2008   .......... A61K 9/2009

OTHER PUBLICATIONS

Biondi-Zoccai et al. "Adjusted indirect comparison meta-analysis of prasugrel versus ticagrelor for patients with acute coronary syndromes", International Journal of Cardiology, 2011, vol. 150, pp. 325-331. (Year: 2011).*
International Search Report dated Jun. 21, 2016, for International Application No. PCT/IB2016/000275, 4 pages.
Written Opinion of the International Searching Authority dated Jun. 21, 2016, for International Application No. PCT/IB2016/000275, 6 pages.
Anonymous, "Positive PEGASUS-TIMI 54 Study With Ticagrelor (Brilinta)," Jan. 14, 2015, retrieved from Internet on May 24, 2015 (URL:https://www.medscape.com/viewarticle/838127), 2 pages.
Anonymous, "PEGASUS-TIMI 54 study of BRILINTA—AstraZeneca," Jan. 14, 2015, retrieved from Internet on May 24, 2016 (URL:https://www.astrazeneca.com/media-centre/press-releases/2015/pegasus-timi-54-study-brilinta-reduction-cardiovascular-thrombotic-events-14012015.htm), 6 pages.
Bonaca et al., "Design and rationale for the Prevention of Cardiovascular Events in Patients with Prior Heart Attack Using Ticagrelor Compared to Placebo on a Background of Aspirin-Thrombolysis in Myocardial Infarction 54 (PEGASUS-TIMI 54) trial," *American Heart Journal*, vol. 167, No. 4, pp. 437-444 (2014).
Lindholm et al., "Ticagrelor vs. clopidogrel in patients with non-ST-elevation acute coronary syndrome with or without revascularization: results from the PLATO trial," *European Heart Journal*, vol. 35, No. 31, pp. 2083-2093 (2014).
Serebruany, "Ticagrelor shift from PLATO to PEGASUS: Vanished mortality benefit, excess cancer deaths, massive discontinuations, and overshooting target events," *International Journal of Cardiology*, vol. 201, pp. 508-512 (2015).
Bonaca et al., "Long-Term Use of Ticagrelor in Patients with Prior Myocardial Infarction," *New England Journal of Medicine*, vol. 372, No. 19, pp. 1791-1800 (2015).

(Continued)

*Primary Examiner* — Kendra D Carter
(74) *Attorney, Agent, or Firm* — Finnegan, Henderson, Farabow, Garrett & Dunner LLP

(57) ABSTRACT

The present disclosure relates to methods for reducing the rate of cardiovascular death, myocardial infarction, or stroke in a patient in recognized need thereof, comprising administering to the patient a pharmaceutical composition comprising 60 mg ticagrelor twice daily.

21 Claims, 27 Drawing Sheets

(56) References Cited

OTHER PUBLICATIONS

Alexopoulos D., "Long-term ticagrelor therapy in patients with prior myocardial infarction significantly reduces ischaemic events, albeit with increased bleeding," Evid Based Med, 2015, vol. 20, No. 4, p. 132.

Amico F, et al., "Long-term use of ticagrelor in patients with prior heart attack: ticagrelor plus aspirin versus aspirin monotherapy," Postgraduate Medicine, 128(2):164-169 (2016).

Bansilal S, et al., "Ticagrelor for Secondary Prevention of Atherothrombotic Events in Patients With Multivessel Coronary Disease," J Am Coll Cardiol. 2018;71(5):489-496.

Bhatt DL, et al., "Reduction in Ischemic Events With Ticagrelor in Diabetic Patients With Prior Myocardial Infarction in PEGASUS-TIMI 54," J Am Coll Cardiol. Jun. 14, 2016;67(23):2732-40.

Bonaca MP, et al., "Prevention of stroke with ticagrelor in patients with prior myocardial infarction. Circulation," Sep. 20, 2016;134(12):861-71.

Bonaca MP, et al., "Efficacy and safety of ticagrelor over time in patients with prior MI in PEGASUS-TIMI 54," J Am Coll Cardiol 2017;70:1368-1375.

Bonaca M, et al., "Ticagrelor for Prevention of Ischemic Events After Myocardial Infarction in Patients With Peripheral Artery Disease," J Am Coll Cardiol. Jun. 14, 2016;67(23):2719-28.

Brilinta®, "Highlights of Prescribing Information," Product Label Revised Mar. 2018, 10 pages.

Cavallari I, et al., "Frequency, Predictors and Impact of Combined Antiplatelet Therapy on Venous Thromboembolism in Patients with Symptomatic Atherosclerosis. Circulation," Feb. 13, 2018;137(7):684-692.

Keaney J., "Balancing the Risks and Benefits of Dual Platelet Inhibition," New England Journal of Medicine, 372(19):1854-56 (2015).

Magnani G, et al., "Efficacy and safety of ticagrelor for long-term secondary prevention of atherothrombotic events in relation to renal function: insights from the PEGASUS-TIMI 54 trial," Eur Heart J. Jan. 21, 2016;37(4):400-8.

Magnuson EA, et al., "Cost-Effectiveness of Long-Term Ticagrelor in Patients With Prior Myocardial Infarction: Results From the PEGASUS-TIMI 54 Trial," J Am Coll Cardiol. Aug. 1, 2017;70(5):527-538.

Magnuson EA, et al., "Reply: Cost-Effectiveness of Long-Term Ticagrelor in Patients With Prior Myocardial Infarction: Analysis by Subgroups," J Am Coll Cardiol. Jan. 2, 2018;71(1):108.

Mearns B., "Long-term ticagrelor use in patients with history of MI," Nature Reviews Cardiology 12, 260 (2015).

Observations by a Third Party in European Application No. 16716055.5-1112 / 3250207; dated Jul. 24, 2018 (40 pages).

Röshammar D, et al., "Exposure-response analyses supporting ticagrelor dosing recommendation in patients with prior myocardial infarction," J Clin Pharmacol. May 2017;57(5):573-583.

Röshammar D, et al., "Population pharmacokinetics of ticagrelor and AR-C124910XX in patients with prior myocardial infarction," Int J Clin Pharmacol Ther. May 2017;55 (2017)(5):416-424.

Sharma S. et al., "Long-Term Use of Ticagrelor in Patients with Prior Myocardial Infarction," N Engl J Med, 2015, 373:1271-275, Letters to the Editor (5 pages).

Storey RF, et a., "Platelet Inhibition With Ticagrelor 60 mg Versus 90 mg Twice Daily in the PEGASUS-TIMI 54 Trial," J Am Coll Cardiol. 2016;67(10):1145-1154.

Thomas MR, et al., "Consistent platelet inhibition with ticagrelor 60 mg twice-daily following myocardial infarction regardless of diabetes status," Thromb Haemost. May 3, 2017;117(5):940-947.

Bonaca MP, et al., "Ischaemic risk and efficacy of ticagrelor in relation to time from $P2Y_{12}$ inhibitor withdrawal in patients with prior myocardial infarction: insights from PEGASUS-TIMI 54," Eur Heart J. Apr. 7, 2016;37(14):1133-42.

Bonaca et al., "Long-Term Use of Ticagrelor in Patients with Prior Myocardial Infarction," New England Journal of Medicine, vol. 372, No. 19, pp. 1791-1800 (2015), Supplementary Appendix (45 pages).

* cited by examiner

Figure 2-Panel A
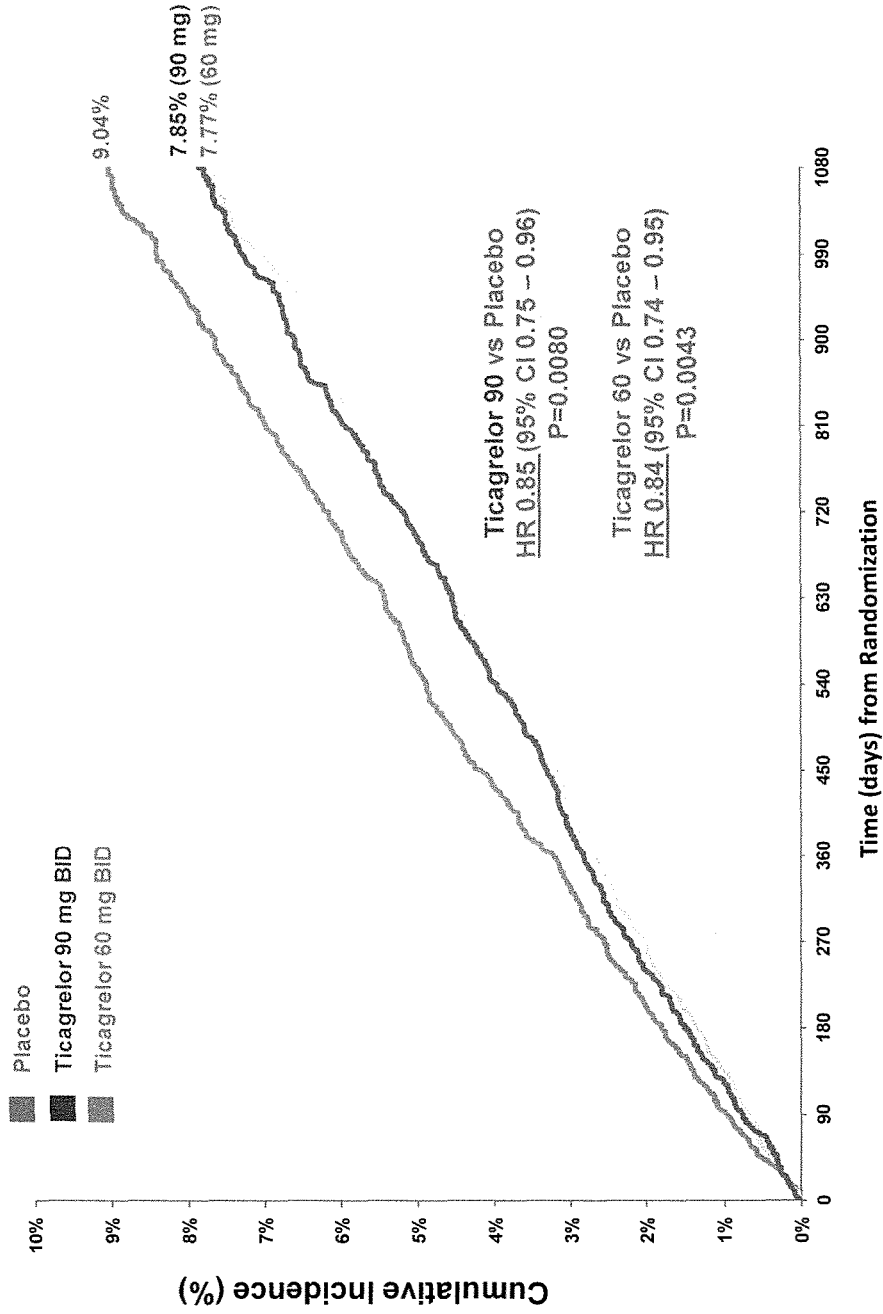

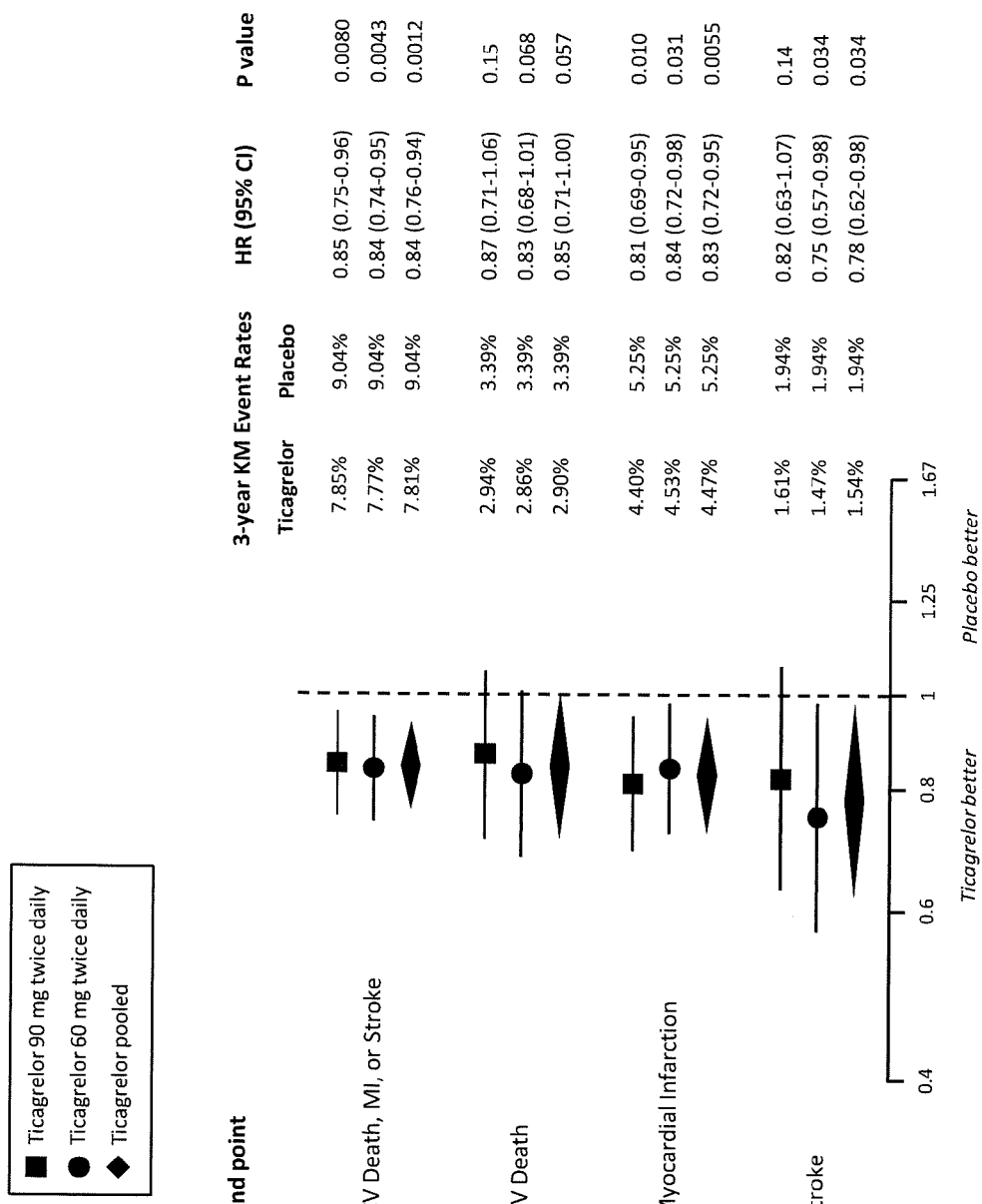
Figure 2-Panel B

Ti = Ticagrelor BID, CI = Confidence interval; HR = Hazard ratio; KM = Kaplan-Meier; N = Number of patients.

The probability of event in each treatment arm is calculated given the median ticagrelor exposure for each arm. The vertical error bars illustrates the median probability of event (point) and the corresponding 95% CI based on parameter uncertainty and assuming a typical patient without risk factors.

The horizontal line within each box represents the median. The box edges represent the lower (25th) and upper (75th) quartiles. The whiskers extend from the lower and upper quartiles to the furthest data points still within a distance of 1.5 interquartile ranges from the lower and upper quartiles The horizontal line within each box represents the median. The box edges represent the lower (25th) and upper (75th) quartiles. The whiskers extend from the lower and upper quartiles to the furthest data points still within a distance of 1.5 interquartile ranges from the lower and upper quartile.

*The dashed thin lines represent the 95% confidence intervals of the KM estimator.

METHOD OF TREATING OR PREVENTION OF ATHEROTHROMBOTIC EVENTS IN PATIENTS WITH HISTORY OF MYOCARDIAL INFARCTION

This application is a National Phase filing of International Application No. PCT/IB2016/000275, filed Jan. 27, 2016, which claims the benefit of priority under 35 U.S.C. § 119 to U.S. provisional patent application Ser. Nos. 62/108,453, filed Jan. 27, 2015; 62/112,318, filed Feb. 5, 2015; 62/117,871, filed Feb. 18, 2015; 62/133,224, filed Mar. 13, 2015; 62/133,327, filed Mar. 14, 2015; 62/156,083, filed May 1, 2015; 62/156,823, filed May 4, 2015; and 62/211,635, filed Aug. 28, 2015.

The present disclosure generally relates to methods of treating or preventing antithrombotic events in patients with acute coronary syndrome (ACS) or a history of myocardial infarction (MI). In one aspect, the present disclosure relates to methods for reducing the rate of cardiovascular death, myocardial infarction, or stroke in a patient with a history of myocardial infarction, comprising administering twice daily to the patient a pharmaceutical composition comprising 60 mg ticagrelor and a pharmaceutically acceptable carrier. In another aspect, the present disclosure relates to methods for reducing the rate of cardiovascular death, myocardial infarction, or stroke in a patient with acute coronary syndrome, comprising administering twice daily to the patient a pharmaceutical composition comprising 60 mg ticagrelor and a pharmaceutically acceptable carrier.

Ticagrelor is a direct-acting reversible binding $P2Y_{12}$ receptor antagonist that inhibits platelet activation and aggregation mediated by the $P2Y_{12}$ ADP-receptor. Ticagrelor, a cyclopentyltrizolopyrimidine, is not in the same chemical class as any other available antiplatelet agent. Currently marked antiplatelet agents include the cyclooxygenase inhibitor acetylsalicylic acid (also known as ASA or aspirin) and the thienopyridines clopidogrel, ticlopidine, and prasugrel. In addition to acting as a $P2Y_{12}$ receptor antagonist, ticagrelor is also known to increase local endogenous adenosine levels by inhibiting equilibrative nucleoside transporter-1 (ENT-1). Adenosine is formed locally at sites of hypoxia and tissue damage through degradation of released adenosine tri- and di-phosphate (ATP and ADP). As adenosine degradation is essentially restricted to the intracellular space, inhibition of ENT-1 by ticagrelor prolongs the half-life of adenosine and thereby increases its local extracellular concentration, providing enhanced local adenosine responses. Adenosine has been documented to have a number of effects that include: vasodilation, cardioprotection, platelet inhibition, modulation of inflammation, and induction of dyspnea, which may contribute to the clinical profile of ticagrelor.

Ticagrelor is also known by its chemical name (1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclopentane-1,2-diol. The empirical formula of ticagrelor is $C_{23}H_{28}F_2N_6O_4S$, and its molecular weight is 522.57 Da. The chemical structure of ticagrelor is:

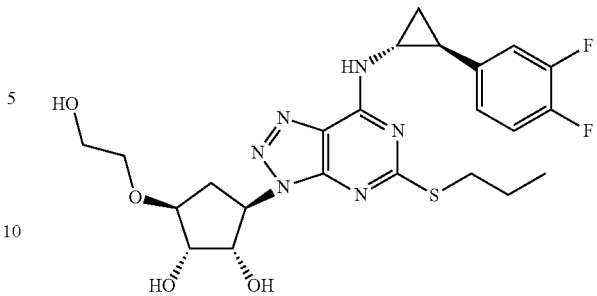

At room temperature, ticagrelor is a crystalline powder with an aqueous solubility of approximately 10 µg/mL.

Ticagrelor can be taken with or without food. In patients, absorption of ticagrelor occurs with a median time to reach the peak plasma concentration of ticagrelor ($c_{max}$) after administration ($t_{max}$) of 1.5 hours with a $t_{max}$ range of 1.0 to 4.0 hours. The formation of the major circulating metabolite AR-C124910XX from ticagrelor occurs with a median $t_{max}$ of 2.5 hours and a range of 1.5 to 5.0 hours. The mean absolute bioavailability of ticagrelor is about 36% (range 30% to 42%). Ingestion of a high-fat meal has no effect on the peak plasma concentration of ticagrelor ($c_{max}$), but results in a 21% increase in the integral of the concentration-time curve (AUC).

Furthermore, ticagrelor as crushed tablets mixed in water, given orally or administered through a nasogastric tube into the stomach, is bioequivalent to whole tablets (AUC and $c_{max}$ within 80% to 125% for ticagrelor and its major metabolite AR-C124910XX) with a median $t_{max}$ of 1.0 hour (range 1.0 to 4.0 hours) for ticagrelor and 2.0 hours (range 1.0 to 8.0 hours) for AR-C124910XX. The steady state volume of distribution of ticagrelor is 88 L. Ticagrelor and AR-C124910XX are extensively bound to human plasma proteins (>99%).

Ticagrelor presents several advantages over other commercially available $P2Y_{12}$ receptor antagonists. For example, ticagrelor is not a prodrug and therefore does not require metabolic activation. In addition, administration of ticagrelor results in a rapid onset of antiplatelet effect (within 2 hours for most patients), low interindividual variability, and reversibility that results in a faster offset of platelet inhibition when compared with thienopyridines such as clopidogrel, ticlopidine, and prasugrel.

The randomized, double blind Platelet Inhibition and Patient Outcomes (PLATO) clinical trial studied ticagrelor 90 mg with aspirin twice daily compared with clopidogrel 75 mg with aspirin once daily in patients presenting across the spectrum of acute coronary syndrome. The results of the PLATO trial showed that ticagrelor reduced ischemic events for up to a year after an acute coronary syndrome. In 2011, BRILINTA®, which contains ticagrelor, was approved by the US Food and Drug Administration (USFDA) in view of the PLATO clinical trial results.

Myocardial infarction is a global problem. In the United States alone, the incidence of acute myocardial infarction is approximately 600,000 cases a year, and nearly 8 million people have a history of myocardial infarction. Moreover, patients who have suffered a myocardial infarction are at heightened risk of recurrent ischemic events. The recent APOLLO RWE clinical trial found that approximately one in every five patients who remain event free for 12 months after a myocardial infarction will suffer a recurrent myocardial infarction, stroke or die from a cardiovascular event in the subsequent 36 months. Accordingly, patients with a history of myocardial infarction may derive particular benefit from intensive secondary prevention.

A key element in the pathobiology of cardiovascular ischemic events is the activated platelet. Correspondingly, antiplatelet therapy is a cornerstone in the prevention of such events. To that end, aspirin reduces ischemic risk in patients presenting with an acute coronary syndrome as well as in long-term secondary prevention. The addition of a $P2Y_{12}$ receptor antagonist to aspirin (referred to as dual anti platelet therapy or DAPT) has previously been shown to further reduce the risk of ischemic events in this population in the first year after an acute coronary syndrome.

The role of $P2Y_{12}$ receptor antagonists in long-term secondary prevention after myocardial infarction, however, has not been established. Both U.S. and European practice guidelines currently recommend treatment with a $P2Y_{12}$ receptor antagonist for up to one year after a myocardial infarction. One of the preferred $P2Y_{12}$ receptor antagonists in patients with an acute coronary syndrome is ticagrelor, a reversibly-binding, direct-acting agent that achieves a high degree of platelet inhibition and has low inter-individual variability. When added to aspirin for up to 1 year in patients with an acute coronary syndrome, ticagrelor 90 mg twice daily reduced major adverse cardiovascular events including cardiovascular death compared with clopidogrel 75 mg once daily, with steady accrual of benefit over time.

Following PLATO, the Prevention of Cardiovascular Events in Patients with Prior Heart Attack Using Ticagrelor Compared to Placebo on a Background of Aspirin (PEGASUS-TIMI 54) trial (also referred to as the PEGASUS trial or PEGASUS study herein) was designed to test the hypothesis that long-term therapy with ticagrelor added to low-dose aspirin will reduce the risk of major adverse cardiovascular events in stable patients with a history of myocardial infarction. Aspirin is known to reduce the risk of ischemic events in patients who present with an acute coronary syndrome and in secondary prevention of myocardial infraction. A significant majority of patients in the PEGASUS trial were administered a daily maintenance dose of 75 mg to 150 mg of aspirin, with less than 0.1% of patients being administered a daily maintenance dose of more or less than 75 mg to 150 mg of aspirin.

Bleeding represents an important safety issue for all antiplatelet medications. Inherent to their pharmacodynamic effects, antiplatelet agents increase the risk of bleeding. There is a risk of bleeding across all degrees of severity from minimal nuisance bleeding to life-threatening and fatal bleeding that may occur during long-term out-of-hospital care or as a result of cardiac and other surgical procedures.

Moreover, it was previously established that ticagrelor is metabolized by the liver, and impaired hepatic function can increase risks for bleeding and other adverse events. Recognizing the balance between ischemic and bleeding risk with antithrombotic therapy and considering that the intensity of antiplatelet therapy required may differ between the acute and chronic settings, the PEGASUS trial evaluated two intensities of ticagrelor therapy: the 90 mg twice daily dose studied in PLATO as well as a lower dose, 60 mg twice daily, to examine whether lower intensity in the chronic phase of long-term therapy may improve the balance of efficacy and bleeding.

Prior to the PEGASUS trial, the optimal intensity of platelet inhibition for long-term therapy was unknown. Ticagrelor doses lower than 60 mg bid were also considered for study in the PEGASUS trial, but modelling predicted that, for example, ticagrelor 45 mg bid would not generate a sustained inhibition of platelet aggregation (IPA) level greater than clopidogrel 75 mg bid. Furthermore, modeling predicted that intra-individual variability in IPA would increase with decreasing ticagrelor dose and that individual variability in IPA would be two to three times greater with ticagrelor 45 mg bid compared to ticagrelor 90 mg bid. While modeling suggested that ticagrelor 60 mg bid could generate a sustained IPA level greater than clopidrogel 75 mg bid with acceptable intra-individual variability, the ticagrelor 60 mg bid dosing regimen had not been tested in man prior to the PEGASUS study. The Dec. 13, 2013 USFDA label, as revised, for the BRILINTA® drug refers only to the PLATO study.

After PLATO, the PEGASUS-TIMI 54 clinical trial (Prevention of Cardiovascular Events in Patients with Prior Heart Attack Using Ticagrelor Compared to Placebo on a Background of Aspirin) was designed to evaluate whether long-term therapy with ticagrelor in addition to aspirin, in an experimental arm, reduces the risk of major adverse cardiovascular events in stable patients with a history of myocardial infarction in comparison with placebo administered in a placebo comparator arm.

In a first aspect, disclosed herein is a method comprising, in a randomized, double blind clinical trial, administering, in an experimental arm, to a patient in recognized need of reducing the risk of cardiovascular death, myocardial infarction, or stroke in the patient, an amount of ticagrelor and aspirin effectively reducing the risk of cardiovascular death, myocardial infarction, or stroke, in the patient, the risk in the experimental arm being effectively reduced compared, in a placebo comparator arm, with the reduction of risk in a patient in recognized need of reducing the risk of cardiovascular death, myocardial infarction, or stroke resulting from administering to the patient a placebo and aspirin, wherein the placebo comparator arm is not an active comparator arm, such as clopidrogel with aspirin, which was the active comparator arm of the PLATO study, and further wherein the patients in both the experimental and the placebo comparator arms had a history of myocardial infarction within 12 to 36 months prior to treatment in the experimental and the placebo comparator arms.

This method was tested and found to be efficacious in the PEGASUS study, a randomized, double blind clinical trial involving over 21,000 patients. Following a comprehensive review of the PEGASUS study results, the USFDA approved a label expansion for the BRILINTA® drug to include administration of ticagrelor 60 mg bid to patients with a history of myocardial infarction. The expanded indication for BRILINTA was approved under USFDA Priority Review, a designation granted to medicines that the USFDA determines to have the potential to provide significant improvements in the treatment, prevention or diagnosis of a disease. The September 2015 USFDA label, as revised, for the BRILINTA® drug refers to both the PLATO and PEGASUS studies.

In some embodiments of the first aspect, the method also shows a trend toward reduced risk of fatal bleeding in a patient administered ticagrelor in an experimental arm compared to a patient administered placebo in the placebo comparator arm.

In some embodiments of the first aspect, ticagrelor is administered 90 mg twice daily in the experimental arm. In some embodiments of the first aspect, ticagrelor is administered 60 mg twice daily in the experimental arm.

In some embodiments of the first aspect, a pharmaceutical composition comprising 90 mg of ticagrelor and a pharmaceutically acceptable carrier is administered twice daily. In some embodiments of the first aspect, a pharmaceutical composition comprising 60 mg of ticagrelor and a pharmaceutically acceptable carrier is administered twice daily in the experimental arm. In some embodiments of the first aspect, the pharmaceutical composition comprising ticagrelor and a pharmaceutically acceptable carrier administered in the experimental arm is a formulation in the form of a tablet administered orally.

In a second aspect, disclosed herein is a method for reducing the rate of a composite endpoint of cardiovascular death, myocardial infarction, or stroke in a patient in recognized need thereof, comprising administering to the patient twice daily a pharmaceutical composition comprising 60 mg ticagrelor and a pharmaceutically acceptable carrier, wherein the patient has a history of myocardial infarction, wherein the patient is also administered a daily maintenance dose of aspirin of 75 mg to 150 mg, and wherein the rate of the composite endpoint in the patient is reduced relative to a dosing regimen where the patient receives the daily maintenance dose of aspirin of 75 mg to 150 mg only.

The efficacy of the disclosed methods of the first and second aspects for reducing the rate of cardiovascular death, myocardial infarction, or stroke was demonstrated by the PEGASUS-TIMI 54 study.

In some embodiments of the first and second aspects, the daily maintenance dose of aspirin is 75 mg to 100 mg.

In some embodiments of the first and second aspects, the patient has a history of myocardial infarction at least 12 months prior to the twice daily administration of the pharmaceutical composition comprising 60 mg ticagrelor and a pharmaceutically acceptable carrier.

In some embodiments of the first and second aspects, the patient has a history of myocardial infarction 12 to 36 months prior to the twice daily administration of the pharmaceutical composition comprising 60 mg ticagrelor and a pharmaceutically acceptable carrier.

In some embodiments of the first and second aspects, the patient has a history of myocardial infarction as a result of an acute coronary syndrome. In some further embodiments of the first and second aspects, prior to the administration, the patient was administered twice daily a pharmaceutical composition comprising 90 mg ticagrelor and a pharmaceutically acceptable carrier for a portion of 12 months after the acute coronary syndrome. In some further embodiments of the first and second aspects, prior to the administration, the patient was administered twice daily a pharmaceutical composition comprising 90 mg ticagrelor and a pharmaceutically acceptable carrier for 12 months after the acute coronary syndrome. In still some further embodiments of the first and second aspects, prior to the administration, the patient was administered a pharmaceutical composition comprising a 180 mg ticagrelor loading dose prior to administration twice daily of a pharmaceutical composition comprising 90 mg ticagrelor and a pharmaceutically acceptable carrier for a portion of the 12 months after the acute coronary syndrome.

In some embodiments of the first and second aspects, no loading dose of ticagrelor is required. In some further embodiments of the first and second aspects, wherein no loading dose of ticagrelor is required, the patient has a history of myocardial infarction at least 12 months prior to the twice daily administration of the pharmaceutical composition comprising 60 mg ticagrelor and a pharmaceutically acceptable carrier.

In some embodiments of the first and second aspects, the method satisfies at least one of the following conditions:

(a) the method numerically reduces the absolute risk of the composite endpoint of cardiovascular death, myocardial infarction, or stroke relative to a dosing regimen where the patient receives the daily maintenance dose of aspirin of 75 mg to 150 mg only;

(b) the method results in a relative risk of the composite endpoint of cardiovascular death, myocardial infarction, or stroke of less than one relative to a dosing regimen where the patient receives the daily maintenance dose of aspirin of 75 mg to 150 mg only;

(c) the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only;

(d) the method results in a statistically significant reduction in the rate of the composite endpoint of cardiovascular death, myocardial infarction, or stroke relative to a dosing regimen where the patient receives the daily maintenance dose of aspirin of 75 mg to 150 mg only;

(e) the method results in a relative risk of the composite endpoint of cardiovascular death, myocardial infarction, or stroke that is statistically significantly less than one relative to a dosing regimen where the patient receives the daily maintenance dose of aspirin of 75 mg to 150 mg only;

(f) the method results in a Kaplan-Meier rate for the composite endpoint of cardiovascular death, myocardial infarction, or stroke at three years of approximately 7.8%;

(g) the method results in a Kaplan-Meier rate for the composite endpoint of cardiovascular death, myocardial infarction, or stroke at three years of 7.8%;

(h) the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only;

(i) the method results in a numerical reduction in the percentage of patients with composite endpoint events of cardiovascular death, myocardial infarction, or stroke relative to a dosing regimen where the patient receives the daily maintenance dose of aspirin of 75 mg to 150 mg only;

(j) the method results in a hazard ratio for time to first composite endpoint of cardiovascular death, myocardial infarction, or stroke that is statistically significantly less than 1 relative to a dosing regimen where the patient receives the daily maintenance dose of aspirin of 75 mg to 150 mg only;

(k) the method results in a hazard ratio for time to first composite endpoint of cardiovascular death, myocardial infarction, or stroke at three years of approximately 0.84 relative to a dosing regimen where the patient receives the daily maintenance dose of aspirin of 75 mg to 150 mg only;

(l) the method results in a hazard ratio for time to first composite endpoint of cardiovascular death, myocardial infarction, or stroke at three years of 0.84 relative to a dosing regimen where the patient receives the daily maintenance dose of aspirin of 75 mg to 150 mg only;

(m) the method results in a hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only;

(n) the method results in a 95% confidence interval for the hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only;

(o) the method reduces the absolute risk of the composite endpoint of cardiovascular death, myocardial infarction, or stroke at three years by approximately 1.27% relative to a dosing regimen where the patient receives the daily maintenance dose of aspirin of 75 mg to 150 mg only;

(p) the method reduces the absolute risk of the composite endpoint of cardiovascular death, myocardial infarction, or stroke at three years by 1.27% relative to a dosing regimen where the patient receives the daily maintenance dose of aspirin of 75 mg to 150 mg only;

(q) the method results in a relative risk reduction of approximately 17% for the composite endpoint of cardiovascular death, myocardial infarction, or stroke from 1 to 360 days relative to a dosing regimen where the patient receives the daily maintenance dose of aspirin of 75 mg to 150 mg only;

(r) the method results in a relative risk reduction of 17% for the composite endpoint of cardiovascular death, myocardial infarction, or stroke from 1 to 360 days relative to a dosing regimen where the patient receives the daily maintenance dose of aspirin of 75 mg to 150 mg only;

(s) the method reduces the Kaplan-Meier rate for the composite endpoint of cardiovascular death, myocardial infarction, or stroke at three years by approximately 1.2% compared to a dosing regimen where the patient receives the daily maintenance dose of aspirin of 75 mg to 150 mg only;

(t) the method reduces the Kaplan-Meier rate for the composite endpoint of cardiovascular death, myocardial infarction, or stroke at three years by 1.2% compared to a dosing regimen where the patient receives the daily maintenance dose of aspirin of 75 mg to 150 mg only;

(u) the method reduces the percentage of patients with composite endpoint events of cardiovascular death, myocardial infarction, or stroke at three years by approximately 1.3% relative to a dosing regimen where the patient receives the daily maintenance dose of aspirin of 75 mg to 150 mg only; or (v) the method reduces the percentage of patients with composite endpoint events of cardiovascular death, myocardial infarction, or stroke at three years by 1.3% relative to a dosing regimen where the patient receives the daily maintenance dose of aspirin of 75 mg to 150 mg only.

In some embodiments of the first and second aspects, the method satisfies at least one of the following conditions:

(a) the method does not result in a hazard ratio for fatal bleeding at 3 years of greater than one relative to a dosing regimen where the patient receives a daily maintenance dose of aspirin of 75 mg to 150 mg only;

(b) the method does not result in a hazard ratio for fatal bleeding at 3 years that is nominally significantly greater than one relative to a dosing regimen where the patient receives a daily maintenance dose of aspirin of 75 mg to 150 mg only;

(c) the method does not result in a relative risk for fatal bleeding at 3 years of greater than one relative to a dosing regimen where the patient receives a daily maintenance dose of aspirin of 75 mg to 150 mg only;

(d) the method does not result in a relative risk for fatal bleeding at 3 years that is nominally significantly greater than one relative to a dosing regimen where the patient receives a daily maintenance dose of aspirin of 75 mg to 150 mg only;

(e) the method does not result in a relative risk for intracranial hemorrhage at 3 years of greater than one relative to a dosing regimen where the patient receives a daily maintenance dose of aspirin of 75 mg to 150 mg only;

(f) the method does not result in a relative risk for intracranial hemorrhage at 3 years that is nominally significantly greater than one relative to a dosing regimen where the patient receives a daily maintenance dose of aspirin of 75 mg to 150 mg only;

(g) the method results in a numerical increase in the number of TIMI major bleeding events per 100 patient years of less than 0.5 relative to a dosing regimen where the patient receives the daily maintenance dose of aspirin of 75 mg to 150 mg only;

(h) the method results in a numerical increase in the number of TIMI major bleeding events per 100 patient years of 0.44 relative to a dosing regimen where the patient receives the daily maintenance dose of aspirin of 75 mg to 150 mg only;

(i) the method does not result in a numerical increase in the number of fatal bleeding events per 100 patient years relative to a dosing regimen where the patient receives the daily maintenance dose of aspirin of 75 mg to 150 mg only;

(j) the method results in a numerical increase in the number of intracranial hemorrhage events per 100 patient years of 0.05 relative to a dosing regimen where the patient receives the daily maintenance dose of aspirin of 75 mg to 150 mg only;

(k) the method results in a difference in the Kaplan-Meier rate of fatal bleeding at three years of less than 0.05% relative to a dosing regimen where the patient receives the daily maintenance dose of aspirin of 75 mg to 150 mg only; or (l) the method results in a difference in the Kaplan-Meier rate of intracranial hemorrhage at three years of less than 0.20% relative to a dosing regimen where the patient receives the daily maintenance dose of aspirin of 75 mg to 150 mg only.

In some embodiments of the first and second aspects, no overall differences in the safety or effectiveness of the method are observed between elderly and younger patients.

In some other embodiments of the first and second aspects, the relative risk reduction of cardiovascular death, myocardial infarction, or stroke with ticagrelor is similar regardless of renal function. In some embodiments of the first and second aspects, the patient is administered a pharmaceutical composition comprising 60 mg ticagrelor and a pharmaceutically acceptable carrier twice daily for up to 47 months.

In some embodiments of the first and second aspects, the method is as effective in reducing the rate of cardiovascular death, myocardial infarction, or stroke in the patient as a method wherein the patient is administered twice daily a pharmaceutical composition comprising 90 mg ticagrelor and a pharmaceutically acceptable carrier and a daily maintenance dose of aspirin of 75 to 100 mg.

In some embodiments of the first and second aspects, the method reduces the rate of irreversible harm to the patient relative to a method wherein the patient is administered twice daily a pharmaceutical composition comprising 90 mg ticagrelor and a pharmaceutically acceptable carrier and a daily maintenance dose of aspirin of 75 to 100 mg.

In some embodiments of the first and second aspects, the method reduces the rate of the composite endpoint of cardiovascular death, myocardial infarction, stroke, intracranial hemorrhage, or fatal bleeding relative to a method wherein the patient is administered twice daily a pharmaceutical composition comprising 90 mg ticagrelor and a pharmaceutically acceptable carrier and a daily maintenance dose of aspirin of 75 to 100 mg.

In some embodiments of the first and second aspects, the method improves the risk-benefit profile of ticagrelor administered on a background of aspirin. In some further embodiments, the method improves the risk-benefit profile relative to a method wherein the patient is administered twice daily a pharmaceutical composition comprising 90 mg ticagrelor and a pharmaceutically acceptable carrier and a daily maintenance dose of aspirin of 75 to 100 mg.

In some embodiments of the first and second aspects, the method results in a net clinical benefit relative to a method wherein the patient is administered twice daily a pharmaceutical composition comprising 90 mg ticagrelor and a pharmaceutically acceptable carrier and a daily maintenance dose of aspirin of 75 to 100 mg.

In some embodiments of the first and second aspects, the method reduces the rate of the composite endpoint of cardiovascular death, myocardial infarction, stroke, TIMI major bleeding relative to a method wherein the patient is administered twice daily a pharmaceutical composition comprising 90 mg ticagrelor and a pharmaceutically acceptable carrier and a daily maintenance dose of aspirin of 75 to 100 mg.

In a third aspect, disclosed herein is a method for reducing the rate of a composite endpoint of cardiovascular death, myocardial infarction, or stroke in a patient in recognized need thereof, comprising administering to the patient twice daily a pharmaceutical composition comprising 60 mg ticagrelor and a pharmaceutically acceptable carrier, wherein the patient has or had acute coronary syndrome, wherein the patient is also administered a daily maintenance dose of aspirin of 75 mg to 150 mg, and wherein the rate of the composite endpoint in the patient is reduced relative to a dosing regimen where the patient receives the daily maintenance dose of aspirin of 75 mg to 150 mg only.

In some embodiments of the third aspect, the patient has acute coronary syndrome.

In some embodiments of the third aspect, the patient had acute coronary syndrome.

In some embodiments of the third aspect, the patient has a history of myocardial infarction.

In some embodiments of the third aspect, the patient has a history of myocardial infarction as a result of acute coronary syndrome.

In some embodiments of the third aspect, the daily maintenance dose of aspirin is 75 mg to 100 mg.

In a fourth aspect, disclosed herein is a method for reducing the rate of a composite endpoint of cardiovascular death, myocardial infarction, or stroke in a patient in recognized need thereof, comprising administering to the patient twice daily a pharmaceutical composition comprising 60 mg ticagrelor and a pharmaceutically acceptable carrier, wherein the patient has history of myocardial infarction or the patient has or had acute coronary syndrome, wherein the patient is also administered a daily maintenance dose of aspirin of 75 mg to 150 mg, and wherein the rate of the composite endpoint in the patient is reduced relative to a dosing regimen where the patient receives the daily maintenance dose of aspirin of 75 mg to 150 mg only.

In some embodiments of the fourth aspect, the daily maintenance dose of aspirin is 75 mg to 100 mg.

In some embodiments of all the aspects, the pharmaceutical composition comprising 60 mg ticagrelor and a pharmaceutically acceptable carrier can be taken with or without food.

In some embodiments of all the aspects, the pharmaceutical composition comprising 90 mg ticagrelor and a pharmaceutically acceptable carrier can be taken with or without food.

In some embodiments of all the aspects, methods disclosed herein are stopped for five days prior to a surgery that has a major risk of bleeding and resumed as soon as possible after hemostasis is achieved.

In some embodiments of all the aspects, the pharmaceutical composition is a solid oral dosage form. In some embodiments of all the aspects, a pharmaceutical composition comprising 60 mg ticagrelor and a pharmaceutically acceptable carrier is formulated as a solid oral dosage form further comprising a filler present in an amount of 20% to 70% by weight, a binder present in an amount of 3% to 6% by weight, a disintegrant present in an amount of 2% to 6% by weight, and a lubricant present in an amount of 0.5% to 1% by weight. In still some further embodiments of all the aspects, the pharmaceutical composition comprising 60 mg ticagrelor and a pharmaceutically acceptable carrier is formulated as a solid oral dosage form further comprising a mixture of mannitol and dibasic calcium phosphate present in an amount of 20% to 70% by weight, hydroxypropyl cellulose present in an amount of 3% to 6% by weight, sodium starch glycolate present in an amount of 2% to 6% by weight, and magnesium stearate present in an amount of 0.5% to 1% by weight.

In some further embodiments of all the aspects, the pharmaceutical composition comprising 60 mg ticagrelor and a pharmaceutically acceptable carrier is formulated as a tablet and administered orally.

In some embodiments of all the aspects, the pharmaceutical composition comprising 60 mg ticagrelor and a pharmaceutically acceptable carrier is formulated as an orally administered tablet further comprising a filler present in an amount of 20% to 70% by weight, a binder present in an amount of 3% to 6% by weight, a disintegrant present in an amount of 2% to 6% by weight, and a lubricant present in an amount of 0.5% to 1% by weight. In still some further embodiments of all the aspects, the pharmaceutical composition comprising 60 mg ticagrelor and a pharmaceutically acceptable carrier is formulated as an orally administered tablet further comprising a mixture of mannitol and dibasic calcium phosphate present in an amount of 20% to 70% by weight, hydroxypropyl cellulose present in an amount of 3% to 6% by weight, sodium starch glycolate present in an amount of 2% to 6% by weight, and magnesium stearate present in an amount of 0.5% to 1% by weight.

In some other embodiments of all the aspects, the pharmaceutical composition comprising 60 mg ticagrelor and a pharmaceutically acceptable carrier is formulated as an orally administered tablet further comprising mannitol, dibasic calcium phosphate, sodium starch glycolate, hydroxypropyl cellulose, magnesium stearate, hydroxypropyl methylcellulose, titanium dioxide, polyethylene glycol 400, ferric oxide black and ferric oxide red. In still some other embodiments of all the aspects, the pharmaceutical composition comprising 60 mg ticagrelor and a pharmaceutically acceptable carrier is formulated as an orally administered tablet further comprising mannitol, dibasic calcium phosphate, sodium starch glycolate, hydroxypropyl cellulose, magnesium stearate, hydroxypropyl methylcellulose, titanium dioxide, polyethylene glycol 400, ferric oxide black and ferric oxide red.

In some embodiments of all the aspects, the pharmaceutical composition comprising 60 mg ticagrelor and a pharmaceutically acceptable carrier is formulated as an orally administered tablet as described in Table 1.

TABLE 1

Orally Administered Tablet Formulation

| Component | Quantity per unit (mg) |
|---|---|
| Tablet core | |
| Ticagrelor | 60 |
| Mannitol | 84 |
| Dibasic calcium phosphate | 42 |
| Sodium starch glycolate | 6 |
| Hydroxypropyl cellulose | 6 |
| Magnesium stearate | 2 |
| Tablet coating | |
| Hydroxypropyl methylcellulose | 4.4 |
| Titanium dioxide | 2.2 |
| Polyethylene glycol 400 | 0.4 |
| Ferric oxide black | 0.001 |
| Ferric oxide red | 0.01 |

In some embodiments of all the aspects, a pharmaceutical composition comprising 90 mg ticagrelor and a pharmaceutically acceptable carrier is formulated as a solid oral dosage form further comprising a filler present in an amount of 20% to 70% by weight, a binder present in an amount of 3% to 6% by weight, a disintegrant present in an amount of 2% to 6% by weight, and a lubricant present in an amount of 0.5% to 1% by weight.

In still some further embodiments of all the aspects, the pharmaceutical composition comprising 90 mg ticagrelor and a pharmaceutically acceptable carrier is formulated as a solid oral dosage form further comprising a mixture of mannitol and dibasic calcium phosphate present in an amount of 20% to 70% by weight, hydroxypropyl cellulose present in an amount of 3% to 6% by weight, sodium starch glycolate present in an amount of 2% to 6% by weight, and magnesium stearate present in an amount of 0.5% to 1% by weight.

In some further embodiments of all the aspects, the pharmaceutical composition comprising 90 mg ticagrelor and a pharmaceutically acceptable carrier is formulated as a tablet and administered orally.

In some embodiments of all the aspects, a pharmaceutical composition comprising 90 mg ticagrelor and a pharmaceutically acceptable carrier is formulated as an orally administered tablet further comprising a filler present in an amount of 20% to 70% by weight, a binder present in an amount of 3% to 6% by weight, a disintegrant present in an amount of 2% to 6% by weight, and a lubricant present in an amount of 0.5% to 1% by weight. In still some further embodiments of all the aspects, the pharmaceutical composition comprising 90 mg ticagrelor and a pharmaceutically acceptable carrier is formulated as an orally administered tablet further comprising a mixture of mannitol and dibasic calcium phosphate present in an amount of 20% to 70% by weight, hydroxypropyl cellulose present in an amount of 3% to 6% by weight, sodium starch glycolate present in an amount of 2% to 6% by weight, and magnesium stearate present in an amount of 0.5% to 1% by weight.

In some other embodiments of all the aspects, the pharmaceutical composition comprising 90 mg ticagrelor and a pharmaceutically acceptable carrier is formulated as an orally administered tablet further comprising mannitol, dibasic calcium phosphate, sodium starch glycolate, hydroxypropyl cellulose, magnesium stearate, hydroxypropyl methylcellulose, titanium dioxide, talc, polyethylene glycol 400, and ferric oxide yellow.

In some further embodiments of all the aspects, the orally administered tablet comprising 90 mg ticagrelor is round, biconvex, yellow, film-coated tablet marked with a "90" above "T" on one side.

In some further embodiments of all the aspects, the orally administered tablet comprising 60 mg ticagrelor is round, biconvex, pink, film-coated tablet marked with "60" above "T" on one side.

In some embodiments of all the aspects, tablets comprising ticagrelor may be crushed, mixed with water and drunk. In some other embodiments of all the aspects, a pharmaceutical composition comprising ticagrelor and a pharmaceutically acceptable carrier may be administered via a nasogastric tube (CH8 or greater).

In some embodiments of all the aspects, a patient who misses an administration of a pharmaceutical composition comprising ticagrelor and a pharmaceutically acceptable carrier is next administered a pharmaceutical composition comprising ticagrelor and a pharmaceutically acceptable carrier (their next pharmaceutical composition) at its scheduled time.

The dosage unit forms of the disclosure can be produced by compacting or compressing an admixture or composition, for example, a powder or granules, under pressure to form a stable three-dimensional shape (e.g., a tablet). As used herein, "tablet" includes compressed pharmaceutical dosage unit forms of all shapes and sizes, whether coated or uncoated.

The expression "dosage unit form" as used herein refers to a physically discrete unit of agent appropriate for the patient to be treated. In general, a compacted mixture has a density greater than that of the mixture prior to compaction. A dosage unit form of the disclosure can have almost any shape including concave and/or convex faces, rounded or angled corners, and a rounded to rectilinear shape. In some embodiments, the compressed dosage forms of the disclosure comprise a rounded tablet having flat faces. The solid pharmaceutical dosage forms of the disclosure can be prepared by any compaction and compression method known by persons of ordinary skill in the art of forming compressed solid pharmaceutical dosage forms. In particular embodiments, the pharmaceutical compositions provided herein may be prepared using conventional methods known to those skilled in the field of pharmaceutical formulation, as described, e.g., in pertinent textbooks. See, e.g., Remington: The Science and Practice of Pharmacy, 21st Ed., Lippincott Williams & Wilkins, Baltimore, Md. (2003); Ansel et al., Pharmaceutical Dosage Forms And Drug Delivery Systems, 7th Edition, Lippincott Williams & Wilkins, (1999); The Handbook of Pharmaceutical Excipients, 4th edition, Rowe et al., Eds., American Pharmaceuticals Association (2003); Gibson, Pharmaceutical Preformulation And Formulation, CRC Press (2001), these references are hereby incorporated herein by reference to the extent they disclose suitable, conventional methods known to those skilled in the field of pharmaceutical formulation.

As described above, the pharmaceutical compositions of the present disclosure comprise a pharmaceutically acceptable carrier, adjuvant, or vehicle, which, as used herein, includes any and all suitable solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with ticagrelor, such as by producing any undesirable biological effect or otherwise interacting in a deleterious manner with any other component(s) of the pharmaceutically acceptable composition, its use is contemplated to be within the scope of this disclosure. Some examples of materials which can serve as suitable pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such as propylene glycol or polyethylene glycol; esters such as ethyl oleate and ethyl laurate; agar; buffering agents, such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator of ordinary skill in the art.

In some embodiments, a pharmaceutical composition comprising ticagrelor and a pharmaceutically acceptable carrier further comprises a filler, a binder, a disintegrant, and a lubricant. In some embodiments, a filler is selected from mannitol, sorbitol, dibasic calcium phosphate dihydrate, dibasic calcium phosphate anhydrate, and tribasic calcium phosphate, or any mixture thereof. In some embodiments, a binder is selected from hydroxypropyl cellulose, alginic acid, carboxymethylcellulose sodium, copovidone, and methylcellulose, or any mixture thereof. In some embodiments, a disintegrant is selected from sodium starch glycolate, croscarmellose sodium, and crospovidone, or any mixture thereof. In some embodiments, a lubricant is selected from magnesium stearate, stearic acid, palmitic acid, calcium stearate, carnauba wax, hydrogenated vegetable oils, mineral oil, polyethylene glycols, and sodium stearyl fumarate.

In some embodiments of all the aspects, a pharmaceutical composition comprising ticagrelor and a pharmaceutically acceptable carrier further comprises a filler present in an amount of 20% to 70% by weight, a binder present in an amount of 3% to 6% by weight, a disintegrant present in an amount of 2% to 6% by weight, and a lubricant present in an amount of 0.5% to 1% by weight.

In some embodiments of all the aspects, a pharmaceutical composition comprising ticagrelor and a pharmaceutically acceptable carrier further comprises a mixture of mannitol and dibasic calcium phosphate present in an amount of 20% to 70% by weight, hydroxypropyl cellulose present in an amount of 3% to 6% by weight, sodium starch glycolate present in an amount of 2% to 6% by weight, and magnesium stearate present in an amount of 0.5% to 1% by weight.

BRIEF DESCRIPTION OF FIGURES

FIG. 2 depicts Kaplan-Meier rates of cardiovascular Death, myocardial infarction, and stroke through 3 years in the PEGASUS-TIMI 54 study by treatment allocation (Panel A), hazard ratios and rates of the primary endpoint and individual components for each dose as well as both doses pooled (Panel B).

DEFINITIONS

Figure 1:
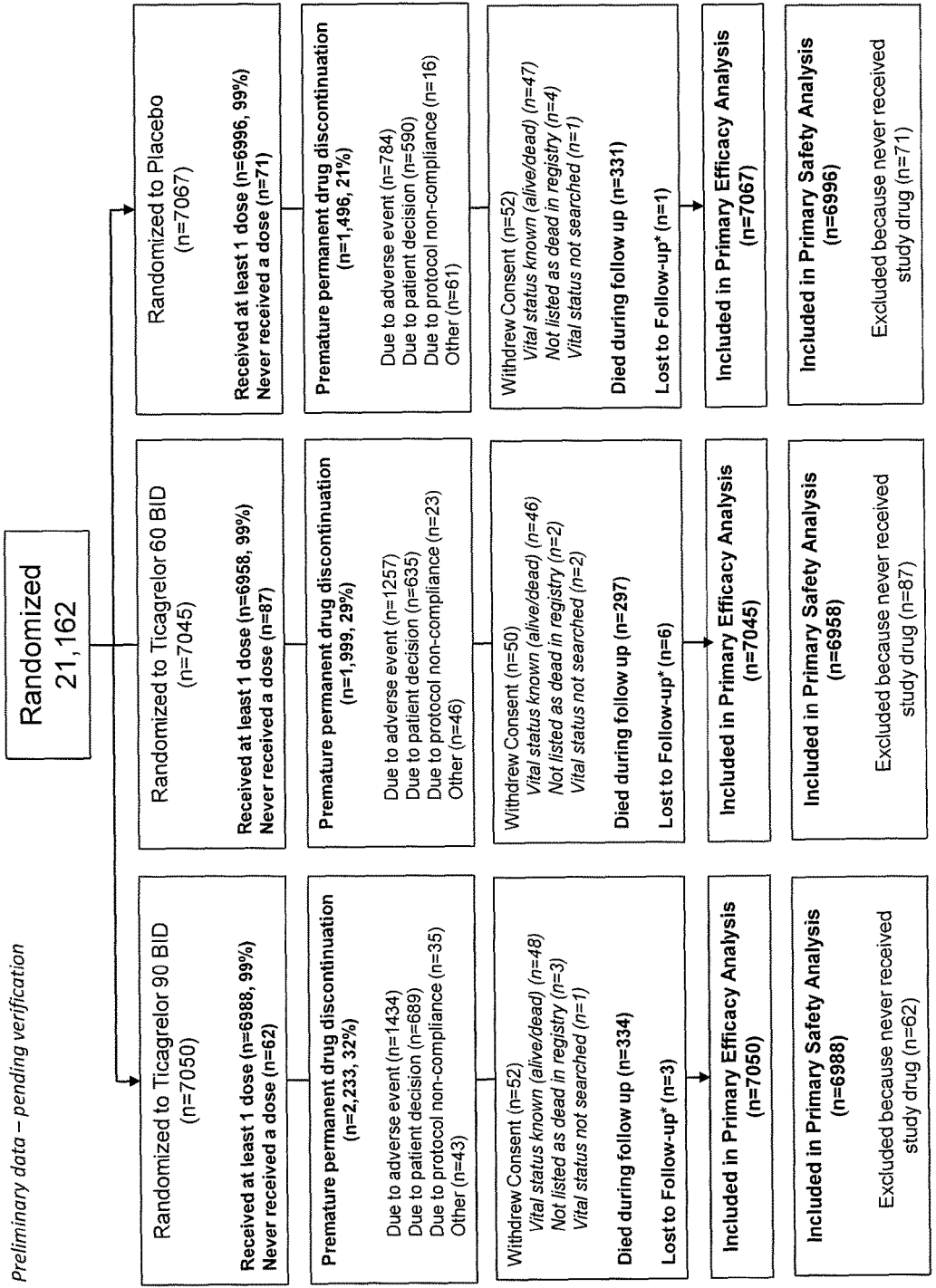
FIG. 1 depicts the trial consort diagram in the PEGASUS-TIMI 54 study.

As used herein, the following definitions shall apply unless otherwise indicated.

As used herein, the term "solid dosage form" generally refers to a pharmaceutical composition, which when used in an oral mode of administration include capsules, tablets, pills, powders and granules. In such solid dosage forms, the active compound is mixed with at least one inert, pharmaceutically acceptable carrier, which can also be referenced as an excipient.

As used herein, an "excipient" or "a pharmaceutically acceptable carrier" includes functional and non-functional ingredients in a pharmaceutical composition.

As used herein, a "disintegrant" is an excipient that hydrates a pharmaceutical composition and aids in tablet dispersion. As used herein, a "diluent" or "filler" is an excipient that adds bulkiness to a pharmaceutical composition.

As used herein, a "surfactant" is an excipient that imparts pharmaceutical compositions with enhanced solubility and/or wetability.

As used herein, a "binder" is an excipient that imparts a pharmaceutical composition with enhanced cohesion or tensile strength (e.g., hardness).

As used herein, a "glidant" is an excipient that imparts a pharmaceutical compositions with enhanced flow properties.

As used herein, a "colorant" is an excipient that imparts a pharmaceutical composition with a desired color. Examples of colorants include commercially available pigments such as FD&C Blue #1 Aluminum Lake, FD&C Blue #2, other FD&C Blue colors, titanium dioxide, iron oxide, and/or combinations thereof. In one embodiment, the pharmaceutical composition provided by the disclosure is purple.

As used herein, a "lubricant" is an excipient that is added to pharmaceutical compositions that are pressed into tablets. The lubricant aids in compaction of granules into tablets and ejection of a tablet of a pharmaceutical composition from a die press.

As used herein, a "$P2Y_{12}$ receptor antagonist" is an antiplatelet agent that at least partially inhibits the function of the G-protein coupled receptor $P2Y_{12}$. Examples of $P2Y_{12}$ receptor antagonists include clopidogrel, prasugrel, ticlopidine, ticagrelor, cangrelor, and elinogrel.

As used herein, an "adenosine diphosphate receptor inhibitor," also referred to as an "ADP receptor blocker" or "ADP rec. block." is an antiplatelet agent that at least partially inhibits the function of some or all types of adenosine diphosphate receptors (i.e., P2Y receptors). "Adenosine diphosphate receptor inhibitor," "ADP receptor blocker," "ADP rec. block," and "$P2Y_{12}$ receptor antagonist" are used interchangeably herein.

As used herein, "net clinical benefit" or "risk-benefit profile" is the time from randomization to the first occurrence of any event from the composite of cardiovascular death, myocardial infarction, stroke or TIMI major bleeding.

As used herein, "irreversible harm" is the time from randomization to first occurrence of any event from the composite of cardiovascular death, myocardial infarction, stroke, intracranial bleeding or fatal bleeding.

As used herein, a "risk factor" is a demographic factor that influences the underlying risk of an event independently of any drug treatment.

As used herein, a "covariate" is a demographic factor that modifies the effect of drug treatment after the impact of risk factors has already been taken into account.

As used herein, the "absolute risk reduction" is the difference in the risk of an outcome in a treatment arm in relation to a comparator or placebo arm.

As used herein, the "relative risk reduction" is the absolute risk reduction divided by the risk of an outcome (alternatively referred to as the rate of an outcome) in the comparator or placebo arm.

As used herein, a "statistically significant reduction in the rate of cardiovascular death, myocardial infarction, or stroke" means the reduction in the rate of cardiovascular death, myocardial infarction, or stroke for the disclosed method relative to a dosing regimen where the patient receives the daily maintenance dose of aspirin of 75 to 150 mg only is statistically significant for at least one of the following statistical metrics: relative risk reduction or hazard ratio. Formal statistical testing included the endpoints of cardiovascular death and all-cause mortality, as well as the composite endpoint of cardiovascular death, myocardial infarction, and stroke. The limit for establishing statistical significance in formal statistical testing, accounting for interim analysis and multiple testing of the two doses of ticagrelor, was p<0.02598. All other p-values recited herein for exploratory endpoints should be considered nominal because the p-values are not controlled for multiplicity. In some embodiments, a statistically significant reduction in the rate of cardiovascular death, myocardial infarction, or stroke is characterized by a p-value of less than 0.026 for one of the aforementioned statistical metrics. In some other embodiments, a statistically significant reduction in the rate of cardiovascular death, myocardial infarction, or stroke is characterized by a p-value of less than 0.01 for one of the aforementioned statistical metrics. In some embodiments, a statistically significant reduction in the rate of cardiovascular death, myocardial infarction, or stroke is characterized by a p-value of less than 0.001 for one of the aforementioned statistical metrics.

As used herein, a "nominally significant" exploratory endpoint is characterized by a p-value of less than 0.05.

As used herein, "Kaplan-Meier rate" or "Kaplan-Meier estimate" refers to the probability of an event or outcome occurring in a given time interval as calculated by the Kaplan-Meier method. More information regarding Kaplan-Meier analysis and survival statistics may be found in Rich, Jason T., et al. "A practical guide to understanding Kaplan-Meier curves." Otolaryngology-Head and Neck Surgery 143.3 (2010): 331-336 and Jager, Kitty J., et al. "The analysis of survival data: the Kaplan-Meier method." Kidney international 74.5 (2008): 560-565.

As used herein, "hazard ratio" means the ratio of hazard rates corresponding to a particular event or outcome in an experimental arm relative to a comparator arm. Hazard ratios measure how often a particular event or outcome occurs in an experimental arm compared to how often in occurs in a comparator arm over time. A hazard ratio of one means that there is no difference in event frequency between the experimental arm and the comparator arm. A hazard ratio of greater than one means an event or outcome occurred more frequently in the experimental arm compared to the comparator arm. A hazard ratio of less than one means an event or outcome occurred less frequently in the experimental arm compared to the comparator arm.

As used herein, "number needed to treat" (NNT) is the number of patients who must follow a treatment regimen over a specified time in order to achieve the desired treatment outcome or endpoint for one person.

As used herein, "number needed to harm" (NTH) is the number of patients who must follow a treatment regimen over a specified time in order to observe an adverse event for one person.

As used herein, "cardiovascular death" means sudden cardiac death, death due to acute myocardial infarction, death due to heart failure, death due to a cerebrovascular event, death due to other cardiovascular causes (i.e., pulmonary embolism, aortic disease, cardiovascular intervention), and deaths for which there was no clearly documented non-cardiovascular cause.

As used herein, "acute coronary syndrome" refers to a condition where blood supplied to the heart muscle is suddenly stopped, i.e., heart attack or unstable angina. Acute coronary syndromes may entail a sudden and complete blockage of blood flow to the heart or a transient blockage.

As used herein, "coronary heart diseases death" (CHD death) means sudden cardiac death, death due to acute myocardial infarction, and the subset of death due to other cardiovascular causes that are secondary to a coronary revascularization procedure.

As used herein, "myocardial infarction" (MI) is diagnosed based on the Universal Myocardial infarction definition published by Thygesen et al in 2007. The terms "myocardial infarction", "myocardial infarction," "spontaneous myocardial infarction," and "spontaneous MI" are used interchangeably herein. Myocardial infarction is diagnosed based on a detection of rise and/or fall of cardiac biomarkers, preferably troponin, with at least one value above the 99th percentile of the upper reference limit (URL) together with evidence of myocardial ischemia with at least one of the following symptoms of myocardial ischemia:

ECG changes (ST segment, T waves, or new left bundle branch block) indicative of new ischemia; development of pathologic Q waves on the ECG; imaging evidence of new loss of viable myocardium or new regional wall motion abnormality;

Sudden unexpected cardiac death, involving cardiac arrest, often with symptoms suggestive of myocardial ischemia, and accompanied by presumably new ST-elevation or new LBBB, and/or evidence of fresh thrombus by coronary angiography and/or autopsy, but death occurring before blood samples could be obtained, or at a time before the appearance of cardiac biomarkers in the blood;

PCI-related Myocardial Infarction: elevation of cardiac biomarkers N3× 99th percentile of the URL within 48 hours after PCI;

CABG-related Myocardial infarction: Elevation of cardiac biomarkers N5×, 99th percentile of the URL within 72 hours after CABG, plus either new pathological Q waves or new LBBB, or angiographically documented new graft or native coronary occlusion, or imaging evidence of loss of viable myocardium;

Silent myocardial infarction based on ECG or imaging findings; or

Pathological findings of an acute myocardial infarction not otherwise meeting above definitions.

As used herein, a patient with a "history of myocardial infarction" or a "history of spontaneous myocardial infarction" refers to a patient who has experienced at least one myocardial infarction diagnosed based on the Universal Myocardial infarction definition published by Thygesen et al in 2007. For example, as referred to herein, a patient with acute coronary syndrome (ACS) is also considered to be a patient with a history of myocardial infarction.

As used herein, "stroke" means an acute episode of neurologic dysfunction attributed to a central nervous system vascular cause.

As used herein, "primary ischemic stroke" means an acute episode of focal brain, spinal, or retinal dysfunction caused by an infarction of central nervous system tissue and documented by imaging.

As used herein, "primary hemorrhagic stroke" means an acute episode of focal or global brain, spinal, or retinal dysfunction caused by non-traumatic intraparenchy-mal, intraventricular, or subarachnoid hemorrhage as documented by neuroimaging or autopsy.

As used herein, "TIMI major bleeding" refers to at least one of: intracranial bleeding; clinically overt signs of hemorrhage associated with a drop in hemoglobin (Hgb) of ≥5 g/dL (or, when hemoglobin is not available, a fall in hematocrit of ≥15%); or fatal bleeding (a bleeding event that directly led to death within 7 days).

As used herein, "other TIMI major bleeding events" refers to TIMI major bleeding events other than intracranial hemorrhage or fatal bleeding.

As used herein, "TIMI minor bleeding" refers to any clinically overt sign of hemorrhage (including imaging) that is associated with a fall in Hgb of 3 to b 5 g/dL (or, when hemoglobin is not available, a fall in hematocrit of 9 to below 15%).

As used herein, the "safety analysis set" refers to all patients who received at least 1 dose of randomized ticagrelor or placebo and for whom post-dose data were available were included in the safety population. Any erroneously treated patients (e.g., randomized to ticagrelor but actually given placebo) were to be accounted for in the actual treatment group.

As used herein, the "efficacy analysis set," the "intention-to-treat analysis set," and the "full analysis set" refers to all randomized patients, irrespective of their protocol adherence and continued participation in the study. Patients were analyzed according to their randomized study drug irrespective of whether the event occurred before or following discontinuation of study drug.

As used herein, "about" or "approximately" means within 20%, such as within 10% and further such as within 5%, of a given value or range.

As used herein, "baseline" refers to "a dosing regimen where the patient receives the daily maintenance dose of aspirin of 75 to 150 mg only." "Baseline" and "a dosing regimen where the patient receives the daily maintenance dose of aspirin of 75 to 150 mg only" may be used interchangeably herein. Endpoints in the PEGASUS-TIMI 54 trial (i.e., relative risk reduction for the composite endpoint of cardiovascular death, myocardial infarction, or stroke) were evaluated for the two doses of ticagrelor relative to baseline.

Example: PEGASUS-TIMI 54 (PEGASUS)

The PEGASUS-TIMI 54 trial (also referred to as the PEGASUS trial or PEGASUS study herein) was a randomized, double-blind, placebo-controlled multinational clinical trial that enrolled over 21,000 patients at 1,161 sites in 31 countries. The protocol was approved by the relevant ethics committees at all participating sites. In the U.S., the PEGASUS trial was assigned a ClinicalTrials.gov number of NCT01225562. Results from the PEGASUS trial were discussed in Bonaca, Marc P., et al. "Long-term use of ticagrelor in patients with prior myocardial infarction." New England Journal of Medicine 372.19 (2015): 1791-1800.

Eligible patients had a history of a spontaneous myocardial infarction 1 to 3 years prior to enrollment and one of the following additional high risk features: age greater than or equal to 65 years; diabetes mellitus requiring medication; a second prior spontaneous myocardial infarction; multivessel coronary artery disease; or chronic renal dysfunction defined as an estimated creatinine clearance less than 60 mL/min. Patients were ineligible if there was planned use of a $P2Y_{12}$ receptor antagonist, dipyridamole, cilostazol, or anticoagulant therapy during the study period or if they required dialysis, had a bleeding disorder, a history of ischemic stroke, an intracranial bleed, tumor, or vascular abnormality, or a recent gastrointestinal bleed or major surgery. Patients could be randomized regardless of their prior adenosine diphosphate (ADP) receptor blocker therapy or a lapse in therapy.

Full eligibility criteria have been previously published (See Bonaca M P, Bhatt D L, Braunwald E, et al. Design and rationale for the Prevention of Cardiovascular Events in Patients With Prior Heart Attack Using Ticagrelor Compared to Placebo on a Background of Aspirin-Thrombolysis in Myocardial infarction 54 (PEGASUS-TIMI 54) trial. *Am Heart J* 2014; 167:437,444.e5, hereinafter referred to as Bonaca), the portions related to full eligibility criteria of which are incorporated herein by reference. Written informed consent was obtained from all patients. Inclusion/exclusion criteria for the PEGASUS trial are shown in Table 2. Most (89.1%) of the patients enrolled in the PEGASUS trial had received previous treatment with an adenosine diphosphate receptor blocker; most commonly clopidogrel (83.7%), with 4.4% having received prasugrel, 0.5% ticlopidine, and 0.4% ticagrelor (Table 3).

TABLE 2

Inclusion/Exclusion Criteria for the PEGASUS-TIMI 54 Trial

| Inclusion | Exclusion |
| --- | --- |
| At least 50 years old | Planned use of ADP receptor blockers, |
| Spontaneous MI 1-3 years prior | dipyridamole or cilostazol |
| plus at least one of the following risk factors: | Planned revascularization (coronary, peripheral, |
| Age of ≥65 | cerebrovascular) |
| Diabetes mellitus on medication | Potent inducer/inhibitor/substrate of CYP3A use |
| A second prior MI | Chronic anticoagulation |
| Multivessel CAD (≥50% in 2+ coronary | Known bleeding diathesis or coagulation disorder |
| territories) | Increased risk of bleeding defined as: |
| Chronic renal dysfunction (non-end | A history of intracranial bleed at any time, |
| stage, est. creat. cl. <60 mL/min) | A central nervous system tumor or |
| Taking ASA 75-150 mg daily | intracranial vascular |
| Contraception in women of child-bearing potential | abnormality (eg, aneurysm, arteriovenous |
| Provides written informed consent | malformation) at any time, |
| | Intracranial or spinal cord surgery within |
| | 5 years, or |
| | A gastrointestinal (GI) bleed within the |
| | past 6 months, or major surgery within 30 |
| | days |
| | History of ischemic stroke |
| | Patients considered to be at risk of bradycardic |
| | events (eg, known sick sinus syndrome or |
| | second or third degree atrioventricular [AV] block) |
| | unless already treated with a permanent |
| | pacemaker |
| | Coronary-artery bypass grafting in the last 5 |
| | years |

TABLE 2-continued

Inclusion/Exclusion Criteria for the PEGASUS-TIMI 54 Trial

| Inclusion | Exclusion |
|---|---|
| | Known severe liver disease |
| | Renal failure requiring dialysis |
| | Pregnancy or lactation |
| | Life-expectancy <1 year |
| | Any condition judged by the investigator to make participation unsafe for the patient |
| | Concern for inability to comply with the protocol |
| | Prior participation in a trial with ticagrelor (if treated with active ticagrelor) |
| | Involvement in planning or conduct of the study |
| | Participation in another clinical study with an investigational product during the prior 30 days |

TABLE 3

Previous treatment with ADP receptor blocker any time prior to randomization (full analysis set)

| | Number (%) of patients | | | |
|---|---|---|---|---|
| Previous treatment | Ticagrelor 90 mg bd N = 7050 | Ticagrelor 60 mg bd N = 7045 | Placebo N = 7067 | Total N = 21162 |
| Patients previously treated with ADP receptor blocker | 6271 (89.0%) | 6289 (89.3%) | 6285 (88.9%) | 18845 (89.1%) |
| Clopidogrel | 5922 (84.0%) | 5915 (84.0%) | 5878 (83.2%) | 17715 (83.7%) |
| Prasugrel | 287 (4.1%) | 317 (4.5%) | 325 (4.6%) | 929 (4.4%) |
| Ticlodipine | 34 (0.5%) | 35 (0.5%) | 38 (0.5%) | 107 (0.5%) |
| Ticagrelor | 31 (0.4%) | 26 (0.4%) | 38 (0.5%) | 95 (0.4%) |
| Missing | 4 (0.1%) | 1 (0.0%) | 5 (0.1%) | 10 (0.0%) |
| Time from last dose to randomisation | | | | |
| Ongoing at randomisation, prior to study drug[a] | 4 (0.1%) | 6 (0.1%) | 10 (0.1%) | 20 (0.1%) |
| After first dose of study drug[b] | 14 (0.2%) | 23 (0.3%) | 12 (0.2%) | 49 (0.2%) |
| 0-7 days | 1826 (25.9%) | 1816 (25.8%) | 1828 (25.9%) | 5470 (25.8%) |
| 8-90 days | 1243 (17.6%) | 1257 (17.8%) | 1243 (17.6%) | 3743 (17.7%) |
| 3-12 months | 1498 (21.2%) | 1520 (21.6%) | 1540 (21.8%) | 4558 (21.5%) |
| >12 months | 1676 (23.8%) | 1661 (23.6%) | 1645 (23.3%) | 4982 (23.5%) |
| Unknown | 10 (0.1%) | 6 (0.1%) | 7 (0.1%) | 23 (0.1%) |
| Reason stopped | | | | |
| Treating physician recommendation | 5901 (83.7%) | 5897 (83.7%) | 5899 (83.5%) | 17697 (83.6%) |
| Patient preference | 325 (4.6%) | 345 (4.9%) | 346 (4.9%) | 1016 (4.8%) |
| Bleeding | 9 (0.1%) | 9 (0.1%) | 9 (0.1%) | 27 (0.1%) |
| Non-bleeding adverse reaction or symptom | 9 (0.1%) | 7 (0.1%) | 7 (0.1%) | 23 (0.1%) |
| Other | 6 (0.1%) | 3 (0.0%) | 4 (0.1%) | 13 (0.1%) |
| Missing | 21 (0.3%) | 28 (0.4%) | 20 (0.3%) | 69 (0.3%) |

Source: CSR Table 11.1.3.11.1
Treatment with ADP receptor blocker at any time prior to randomisation.
[a]Treatment with open label ADP receptor blocker continued on or after day of randomisation, but stopped prior to first dose of study drug
[b]Treatment with open label ADP receptor blocker continued after the first dose of study drug (protocol violation)
ADP Adenosine diphosphate;
bd Twice daily;
N Number of patients in treatment group Eligible patients were randomized in a 1:1:1 ratio to receive ticagrelor 90 mg orally twice daily, ticagrelor 60 mg orally twice daily, or placebo. Randomization was performed using a central computerized telephone or web based system, and allocation was double-blind. The mean time from qualifying myocardial infarction to randomization in the study was 21.8 months, and the majority of patients (60.7%) had a qualifying myocardial infarction one to two years prior to randomization.

A modified study treatment option (blinded double dummy ticagrelor or clopidogrel) was provided to investigators for use if a patient developed an indication for $P2Y_{12}$ receptor blockade as previously published (See Bonaca). The modified treatment option was used by less than 4% of patients during the study. Patients undergoing elective major non-cardiovascular procedures were advised to stop study treatment 5 days prior to the procedure and resume it when deemed appropriate by the treating physician. The protocol also defined discontinuation criteria for temporary interruption and permanent discontinuation from treatment with ticagrelor (Table 4).

All patients enrolled in the PEGASUS trial were instructed to take open label aspirin at a dose of 75 to 150 mg daily. Because the study population was stable, no loading dose of ticagrelor was administered.

The primary efficacy endpoint was the composite of cardiovascular death, myocardial infarction, or stroke. Secondary endpoints were cardiovascular death and all-cause mortality. The analysis of secondary endpoints proceeded in a hierarchical fashion, starting with cardiovascular death and then death from any cause. Additional endpoints listed below were evaluated on an exploratory basis. Exploratory efficacy endpoints included substituting coronary heart disease death for cardiovascular death, and the additional end points of urgent coronary revascularization, unstable angina, and transient ischemic attack. The primary safety endpoint was TIMI major bleeding. Other safety endpoints included intracranial hemorrhage (ICH) and fatal bleeding. Definitions of the endpoints have been previously published (See Bonaca). A central clinical events committee whose members were unaware of the treatment assignments adjudicated all efficacy endpoints and bleeding episodes.

TABLE 4

Protocol-defined discontinuation criteria

| Temporary interruption of study drug | Permanent discontinuation from treatment with study drug |
|---|---|
| Severe thrombocytopenia (platelet count <50,000/: L). Patients could restart study drug once severe thrombocytopenia resolved. Major surgery (for elective minor surgery or other invasive procedures, study drug could be continued or interrupted temporarily at the Investigator's discretion) Major bleeding Development of a reversible bleeding diathesis or coagulation disorder Need for treatment with prohibited concomitant medications Development of significant conduction system disease (eg sick sinus syndrome or second or third degree atrioventricular [AV] block) until treated with a pacemaker Severe hepatic impairment | The Investigator could decide to permanently discontinue study drug, in consultation with the TIMI Hotline, for the following safety-related reasons: Incorrectly enrolled patient in whom the eligibility criteria violation would put the patient at undue risk Development of a condition that would subject the patient to undue risk: Ischaemic stroke or intracranial bleeding of any kind; intracranial or spinal cord surgery; discovery of a CNS tumour or intracranial vascular abnormality (eg, aneurysm, arteriovenous malformation) Development of chronic bleeding diathesis or coagulation disorder Renal failure requiring dialysis Pregnancy Development of significant conduction system disease (eg, sick sinus syndrome or second or third degree AV block) not treated with a permanent pacemaker AE considered to be related to study drug, for which the Investigator felt continued treatment would put the patient at undue risk. Severe non-compliance with protocol. |

A total of 1360 primary endpoint events would be required to provide approximately 90% power to detect a 20% relative risk reduction with the 90 mg twice daily dose and approximately 83% power to detect a 19% relative risk reduction with the 60 mg twice daily dose when each dose was compared individually with placebo. The primary efficacy analysis was conducted on an intention-to-treat basis, with each of the two doses individually compared to placebo, as a time to event analysis from randomization to the first occurrence of any element of the primary composite endpoint: cardiovascular death, myocardial infarction, or stroke. Analysis of secondary endpoints proceeded in a hierarchical fashion, starting with CV death. An exploratory analysis of both doses combined compared with placebo was prespecified.

Safety analyses included all randomized patients who received at least one dose of study drug and for whom post-dose data were available. Patients were censored at the first of the pre-specified Common Study End Date, withdrawal of consent, or the last clinical event assessment. Safety was analyzed as on-treatment including all events occurring after first dose and within 7 days after the last dose of study drug. To control overall type I error, alpha was apportioned to each ticagrelor dose-placebo comparison (using a correlation of 0.5 between the test statistics) and a Haybittle-Peto approach was employed to take into account an interim analysis of efficacy that was performed by the Independent Data Monitoring Committee, resulting in a significance level of 0.026 being indicative of statistical significance for the final analyses. Event rates are expressed as Kaplan-Meier estimates of cumulative incidence. Hazard ratios and 95% confidence intervals were generated using a Cox proportional hazards model and all reported P values are two-sided. Because clinical trials are conducted under widely varying conditions, adverse reaction rates observed in clinical trials cannot be directly compared to rates in the clinical trials of another drug and may not reflect the rates observed in practice.

A total of 21,162 patients were randomized between October 2010 and April 2013. Trial sample size determination was made with the assumptions of a 3.5% per year event rate for the primary endpoint in the placebo group based on prior studies in similar populations and a target relative risk reduction for the ticagrelor 90 mg bid arm of 20% and approximately 19% for the ticagrelor 60 mg bid dose compared with placebo arm. Baseline characteristics of the patients were well balanced between the experimental and comparator placebo treatment arms (Tables 5 and 6).

TABLE 5

Baseline Characteristics of All Patients in the PEGASUS-TIMI 54 Trial

| Demographic | % Patients |
|---|---|
| <65 years | 45% |
| Diabetes | 32% |
| Multivessel disease | 59% |
| History of >1 MI | 17% |
| Chronic non-end stage renal disease | 19% |
| Stent | 80% |
| Prior P2Y12 platelet inhibitor therapy | 89% |
| Lipid lowering therapy | 94% |

TABLE 6

Baseline Characteristics of the Patients by Treatment Group

| Characteristic | Ticagrelor 90 mg bid N = 7050 n (%) | Ticagrelor 60 mg bid N = 7045 n (%) | Placebo N = 7067 n (%) |
|---|---|---|---|
| Demographics | | | |
| Age - yr, mean (SD) | 65.4 (8.4) | 65.2 (8.4) | 65.4 (8.3) |
| Female | 1682 (23.9) | 1661 (23.6) | 1717 (24.3) |
| Caucasian* | 6126 (86.9) | 6077 (86.3) | 6124 (86.7) |
| Weight - kg, mean (SD) | 82 (16.7) | 82 (17.0) | 82 (16.6) |

TABLE 6-continued

Baseline Characteristics of the Patients by Treatment Group

| Characteristic | Ticagrelor 90 mg bid N = 7050 n (%) | Ticagrelor 60 mg bid N = 7045 n (%) | Placebo N = 7067 n (%) |
|---|---|---|---|
| Clinical Characteristics | | | |
| Hypertension | 5462 (77.5) | 5461 (77.5) | 5484 (77.6) |
| Hypercholesterolemia | 5410 (76.7) | 5380 (76.4) | 5451 (77.1) |
| Current smoker | 1187 (16.8) | 1206 (17.1) | 1143 (16.2) |
| Diabetes mellitus | 2241 (31.8) | 2308 (32.8) | 2257 (31.9) |
| Multivessel coronary disease | 4155 (58.9) | 4190 (59.5) | 4213 (59.6) |
| History of PCI | 5852 (83.0) | 5879 (83.5) | 2837 (82.6) |
| History of more than 1 prior MI | 1143 (16.2) | 1168 (16.6) | 1188 (16.8) |
| Peripheral artery disease | 371 (5.3) | 368 (5.2) | 404 (5.7) |
| Creatinine clearance <60 mL/min | 428 (6.1) | 403 (5.7) | 423 (6.0) |
| Qualifying Event | | | |
| Years from MI - median (IQR) | 1.7 (1-2) | 1.7 (1-2) | 1.7 (1-2) |
| STEMI | 3763 (53.4) | 3757 (53.4) | 3809 (54.0) |
| NSTEMI | 2898 (41.1) | 2842 (40.4) | 2743 (40.3) |
| MI type unknown | 382 (5.4) | 436 (6.2) | 405 (5.7) |
| Medications at enrollment | | | |
| Aspirin (any dose) | 6846 (97.1) | 6847 (97.2) | 6865 (97.1) |
| Statin | 6532 (92.5) | 6491 (92.1) | 6582 (93.1) |
| Beta-blocker | 5809 (82.4) | 5787 (82.1) | 5870 (83.1) |
| ACEI or ARB | 5709 (81.0) | 5637 (80.0) | 5703 (80.7) |
| Geographic region/country | | | |
| Asia and Australia | 793 (11.2%) | 788 (11.2%) | 788 (11.2%) |
| Europe and South Africa | 4128 (58.6%) | 4146 (58.9%) | 4154 (58.8%) |
| North America | 1307 (18.5%) | 1297 (18.4%) | 1303 (18.4%) |
| South America | 822 (11.7%) | 814 (11.6%) | 822 (11.6%) |
| USA | 866 (12.3%) | 863 (12.2%) | 872 (12.3%) |

*Self-reported
ACEI, angiotensin-converting enzyme inhibitor; ARB, angiotensin receptor blocker.

The mean (SD) age was 65 (8) years, nearly one quarter of patients were female, and close to one third had diabetes mellitus. Patients were predominantly Caucasian (87%), and 99.8% of patients received prior aspirin therapy. The safety population was predominantly Caucasian (86.7%). 12.1% of patients enrolled in PEGASUS were Hispanic or Latino, and Black (1.7%), Asians (10.7%), and other (0.9%) races also participated in the study. The median time from the qualifying myocardial infarction to randomization was 1.7 years (IQR 1.0-2.0) with 54% of the qualifying events being ST-segment-elevation myocardial infarction. The majority of the patients had a history of percutaneous coronary intervention (PCI) (83%) and multivessel coronary artery disease (59%). In regards to additional pre-defined atherothrombotic risk factors, 54.4% of the patients were aged ≥65 years, 28.5% had diabetes mellitus requiring medication, 16.5% had a history of a second prior presumed spontaneous MI (≥1 year prior to randomization), 59.3% had a history of angiographic evidence of multivessel CAD, and 5.9% had chronic non-end stage renal dysfunction (as reported by the investigator). 47.8% of the patients had more than one risk factor for atherothrombosis, and 14.6% had three or more risk factors. The randomized treatment groups were balanced with regard to these pre-defined atherothrombotic risk factors.

Patients were well treated according to current guidelines (Table 7) (see Fihn S D, Gardin J M, Abrams J, et al. 2012 "ACCF/AHA/ACP/AATS/PCNA/SCAI/STS guideline for the diagnosis and management of patients with stable ischemic heart disease: a report of the American College of Cardiology Foundation/American Heart Association task force on practice guidelines, and the American College of Physicians, American Association for Thoracic Surgery, Preventive Cardiovascular Nurses Association, Society for Cardiovascular Angiography and Interventions, and Society of Thoracic Surgeons." Circulation 2012; 126:e354-471, and Task Force Members, Montalescot G, Sechtem U, et al. "2013 ESC guidelines on the management of stable coronary artery disease: the Task Force on the management of stable coronary artery disease of the European Society of Cardiology." Eur Heart J 2013; 34:2949-3003).

Nearly all patients (95.7%) received aspirin at a dose between 75 mg and 100 mg. Few patients (2.7%) took more than 100 mg of aspirin, and very few patients (<0.1%, N=97) took more or less than the daily maintenance dose of 75 to 150 mg of aspirin mandated in the PEGASUS-TIMI 54 study protocol. As expected, due to prescription practices in the United States and elsewhere, doses of 75 to 81 mg and 100 mg of aspirin dominated (48.9% and 48.3%, respectively). Maintenance doses of aspirin above 100 mg were shown to reduce the effectiveness of ticagrelor for patients with acute coronary syndrome in the PLATO trial.

20,942 patients (99.0%) received at least one dose of study drug. The proportion of patients in each arm who prematurely discontinued treatment over the duration of the trial was 32.0%, 28.7%, and 21.4% in ticagrelor 90 mg, ticagrelor 60 mg, and placebo arms, respectively (P<0.001 for each dose versus placebo). Of patients on study drug, compliance (defined as taking ≥80% of pills administered while on treatment) was 79%, 80%, and 82% in ticagrelor 90 mg, ticagrelor 60 mg, and placebo arms, respectively.

Figure 3:
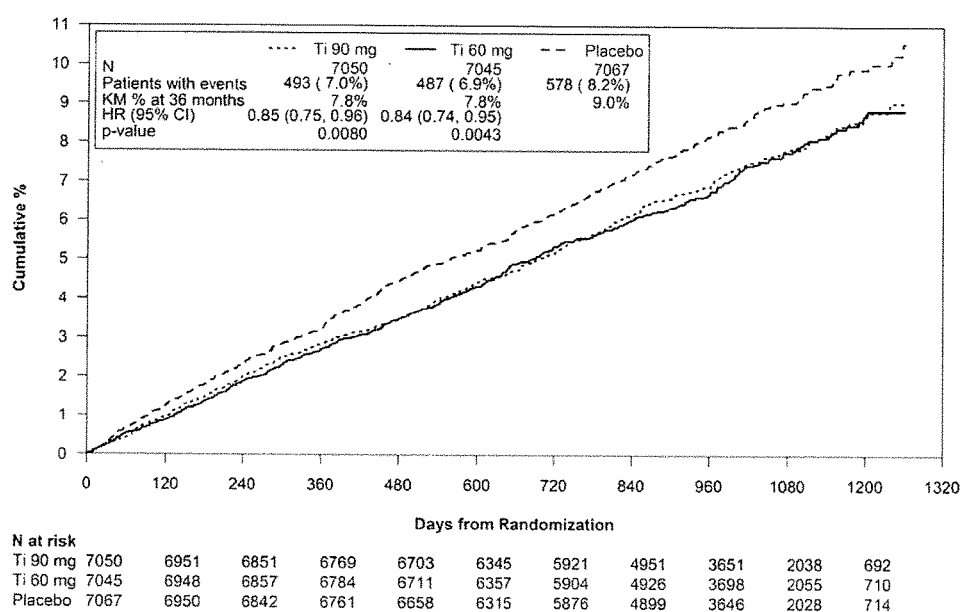
FIG. 3 depicts Kaplan-Meier rates of cardiovascular death, myocardial infarction, and stroke through 3 years in the PEGASUS-TIMI 54 study by treatment allocation.

The median duration of follow up was 33 months (IQR 28-37) resulting in 55,266 patient years of follow-up. Ascertainment of the primary endpoint was complete for 98.8% of potential patient years of follow up. Details of patient disposition are described in FIG. 1. Both doses of ticagrelor in the experimental arm significantly reduced the primary endpoint of cardiovascular death, myocardial infarction, or stroke compared to placebo with Kaplan-Meier rates at 3 years of 7.85% in the ticagrelor 90 mg arm, 7.77% in the ticagrelor 60 mg arm, and 9.04% in the placebo arm (HR for ticagrelor 90 mg vs placebo 0.85, 95% CI 0.75-0.96, P=0.0080; HR for ticagrelor 60 mg vs placebo 0.84, 95% CI 0.74-0.95, P=0.0043) (FIG. 2A, FIG. 3). Each of the primary endpoint components of cardiovascular death, myocardial infarction, and stroke contributed to the reduction in the primary composite endpoint. Based on intention-to-treat data (i.e., regardless of study drug discontinuation), if 10,000 patients were started on treatment with ticagrelor versus placebo, 40 and 42 ischemic events would be prevented with ticagrelor 90 mg bid and ticagrelor 60 mg bid, respectively. The effect of ticagrelor on each of the components of the primary endpoint was highly consistent (FIG. 2B). Similarly, there was a numerical reduction in the rate of the composite of coronary heart disease death, myocardial infarction, or stroke for both ticagrelor doses compared with placebo (18% RRR, HR 0.82 (95% CI 0.72, 0.93), p=0.0016 for 90 mg bid and 17% RRR, HR 0.83 (95% CI 0.73, 0.94), p=0.0033 for ticagrelor 60 mg bid). In addition, there was a numerical reduction in the rate of coronary stent thrombosis for both ticagrelor doses compared with placebo (36% RRR, HR 0.64 (95% CI 0.41, 1.00), p=0.0499 for ticagrelor 90 mg bid, and 18% RRR, HR 0.82 (95% CI 0.54, 1.23), p=0.3328 for ticagrelor 60 mg bid). Analysis of time to first stent thrombosis for each treatment group is shown in Table 7. There was a trend with ticagrelor toward a numerical reduction in the rate of cardiovascular death alone, but the effect was not statistically significant. The difference in the rate of death from any cause was not statistically significant for either dose of ticagrelor compared to placebo (Table 8). The frequency of death (including bleeding) was 4.8% (n=333), 4.2% (n=290), and 4.7% (n=329) for the ticagrelor 90 mg bid, ticagrelor 60 mg bid, and placebo arms, respectively. When bleeding events were excluded, the frequency of death was 4.4% (n=304), 3.9% (n=274), and 4.4% (n=309) for ticagrelor 90 mg bid, ticagrelor 60 mg bid, and placebo arms, respectively. Of note, PEGASUS was powered to detect changes in the primary composite endpoint of CV death, MI or stroke only. The study was not powered to detect changes in cardiovascular death or total mortality. P-values recited in Table 8 except for the cardiovascular death endpoint, all-cause mortality endpoint, and primary composite endpoint of cardiovascular death, myocardial infarction, or stroke were not controlled for multiplicity and should be considered as nominal. Other prespecified efficacy endpoints including hospitalization for unstable angina and transient ischemic attack were infrequent in all arms ($\leq 1\%$ at 3 years) and are shown in Tables 9 and 10. There were no significant differences in the rates of urgent revascularization, hospitalization for unstable angina, or transient ischemic attack with either ticagrelor dose compared to placebo (Table 9).

TABLE 7

Analysis of Time to First Stent Thrombosis (Full Analysis Set)

| Characteristic | Ticagrelor 90 mg bd N = 7050 | | | | Ticagrelor 60 mg bd N = 7045 | | | | Placebo N = 7067 | |
|---|---|---|---|---|---|---|---|---|---|---|
| | Patients (%) with events | KM % | HR (95% CI) | p-value | Patients (%) with events | KM % | HR (95% CI) | p-value | Patients (%) with events | KM % |
| Patients with a history of coronary stent implantation or receiving a stent during the study | 5651 | | | | 5695 | | | | 5661 | |
| Stent thrombosis | 32 (0.6%) | 0.6% | 0.64 (0.41, 1.00) | 0.0499 | 41 (0.7%) | 0.8% | 0.82 (0.54, 1.23) | 0.3328 | 50 (0.9%) | 0.9% |

Hazard ratios and p-values are calculated separately for each ticagrelor dose vs placebo from Cox proportional hazards model with treatment group as the only explanatory variable.
Kaplan-Meier percentage calculated at 36 months.
For patients with stent thrombosis attributed to a stent implanted before randomization, time is calculated from the date of randomization.
For patients with stent thrombosis attributed to a stent implanted after randomization, time is calculated from the date of stent implantation.
If a patient had more than 1 stent and the stent thrombosis could not be attributed to a specific stent, then it is assumed to have occurred in the most recent stent.
bd Twice daily;
CI Confidence interval;
HR Hazard ratio;
KM Kaplan-Meier;
N Number of patients in treatment group

TABLE 8

Efficacy Endpoints

| Endpoint | Ticagrelor 90 mg bid (N = 7050) n (%) | Ticagrelor 60 mg bid (N = 7045) n (%) | Placebo (N = 7067) n (%) | Ticagrelor 90 mg bid vs Placebo HR (95% CI) p-value | Ticagrelor 60 mg bid vs Placebo HR (95% CI) p-value |
|---|---|---|---|---|---|
| Cardiovascular Death, Myocardial infarction, or Stroke | 493 (7.85) | 487 (7.77) | 578 (9.04) | 0.85 (0.75-0.96) P = 0.0080 | 0.84 (0.74-0.95) P = 0.0043 |
| Coronary Heart Disease Death, Myocardial infarction, or Stroke | 438 (6.99) | 445 (7.09) | 535 (8.33) | 0.82 (0.72-0.93) P = 0.0016 | 0.83 (0.73-0.94) P = 0.0033 |
| Cardiovascular Death or Myocardial infarction | 424 (6.79) | 422 (6.77) | 497 (7.81) | 0.85 (0.75-0.97) P = 0.014 | 0.85 (0.74-0.96) P = 0.012 |
| Coronary Heart Disease Death or Myocardial infarction | 350 (5.59) | 360 (5.57) | 429 (6.68) | 0.81 (0.71-0.94) P = 0.0041 | 0.84 (0.73-0.96) P = 0.013 |
| Cardiovascular Death | 182 (2.94) | 174 (2.86) | 210 (3.39) | 0.87 (0.71-1.06) P = 0.15 | 0.83 (0.68-1.01) P = 0.067 |
| Coronary Heart Disease Death | 97 (1.53) | 106 (1.72) | 132 (2.08) | 0.73 (0.56-0.95) P = 0.021 | 0.80 (0.62-1.04) P = 0.093 |

TABLE 8-continued

Efficacy Endpoints

| Endpoint | Ticagrelor 90 mg bid (N = 7050) n (%) | Ticagrelor 60 mg bid (N = 7045) n (%) | Placebo (N = 7067) n (%) | Ticagrelor 90 mg bid vs Placebo HR (95% CI) p-value | Ticagrelor 60 mg bid vs Placebo HR (95% CI) p-value |
|---|---|---|---|---|---|
| Myocardial infarction | 275 (4.40) | 285 (4.53) | 338 (5.25) | 0.81 (0.69-0.95) P = 0.010 | 0.84 (0.72-0.98) P = 0.031 |
| All Stroke | 100 (1.61) | 91 (1.47) | 122 (1.94) | 0.82 (0.63-1.07) P = 0.14 | 0.75 (0.57-0.98) P = 0.034 |
| Ischemic Stroke | 88 (1.41) | 78 (1.28) | 103 (1.65) | 0.85 (0.64-1.14) P = 0.28 | 0.76 (0.56-1.02) P = 0.063 |
| Death from any cause | 326 (5.15) | 289 (4.69) | 326 (5.16) | 1.00 (0.86-1.16) P = 0.99 | 0.89 (0.76-1.04) P = 0.14 |

Rates are presented as 3-year Kaplan-Meier estimates

TABLE 9

Other Efficacy Endpoints

| Endpoint | Ticagrelor 90 mg bid (N = 7050) n (%) | Ticagrelor 60 mg bid (N = 7045) n (%) | Placebo (N = 7067) n (%) | Ticagrelor 90 mg bid vs Placebo HR (95% CI) p-value | Ticagrelor 60 mg bid vs Placebo HR (95% CI) p-value |
|---|---|---|---|---|---|
| Hospitalization for Unstable Angina | 33 (0.50) | 39 (0.61) | 37 (0.57) | 0.89 (0.56-1.43) 0.63 | 1.05 (0.67-1.65) 0.82 |
| Urgent Coronary Revascularization for Unstable Angina | 74 (1.16) | 62 (0.95) | 76 (1.13) | 0.97 (0.71-1.34) 0.87 | 0.82 (0.58-1.14) 0.24 |
| Transient Ischemic Attack | 17 (0.27) | 17 (0.27) | 17 (0.29) | 1.00 (0.51-1.96) P = 1.00 | 1.00 (0.51-1.96) P = 1.00 |

TABLE 10

Incidences of the Primary Composite Endpoint, Primary Composite Endpoint Components, and Secondary Endpoints in the PEGASUS-TIMI 54 Trial

| | Ticagrelor 60 mg bid (N = 7045) | | Placebo (N = 7067) | | | |
|---|---|---|---|---|---|---|
| | n (patients with event) | KM % | n (patients with event) | KM % | HR (95% CI) | p-value |
| Time to first CV death, MI, or stroke* | 487 | 7.8 | 578 | 9.0 | 0.84 (0.74, 0.95) | 0.0043 |
| CV Death$^a$ | 116 | | 128 | | | |
| Myocardial infarction$^a$ | 283 | | 336 | | | |
| Stroke$^a$ | 88 | | 114 | | | |
| Subjects with events at any time | 174 | 2.9 | 210 | 3.4 | 0.83 (0.68, 1.01) | |
| CV Death$^{b}$** | | | | | | |
| Myocardial infarction$^b$ | 285 | 4.5 | 338 | 5.2 | 0.84 (0.72, 0.98) | |
| Stroke$^b$ | 91 | 1.5 | 122 | 1.9 | 0.75 (0.57, 0.98) | |
| All-cause mortality** | 289 | 4.7 | 326 | 5.2 | 0.89 (0.76, 1.04) | |

*60 mg BID
CI = Confidence interval;
CV = Cardiovascular;
HR = Hazard ratio;
KM = Kaplan-Meier percentage calculated at 36 months;
MI = Myocardial infarction;
N = Number of patients;
*Primary endpoint;
**Secondary endpoints.
$^a$For the components, the first-occurring component of the composite is included.
$^b$The number of first events for the components CV Death, MI and Stroke are the actual number of first events for each component and do not add up to the number of events in the composite endpoint.

Figure 4:
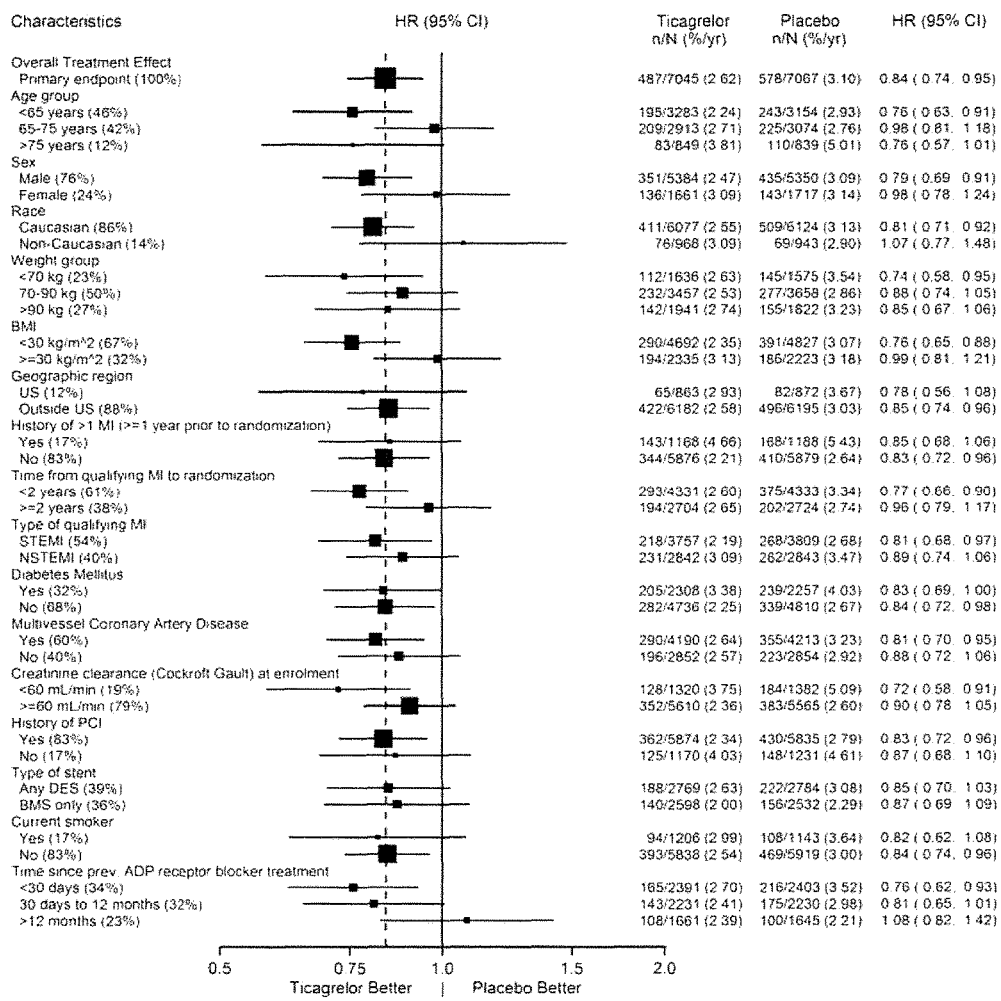
FIG. 4 depicts primary efficacy endpoint subgroup analyses of ticagrelor 60 mg bid in the PEGASUS-TIMI 54 trial.
Figure 5:
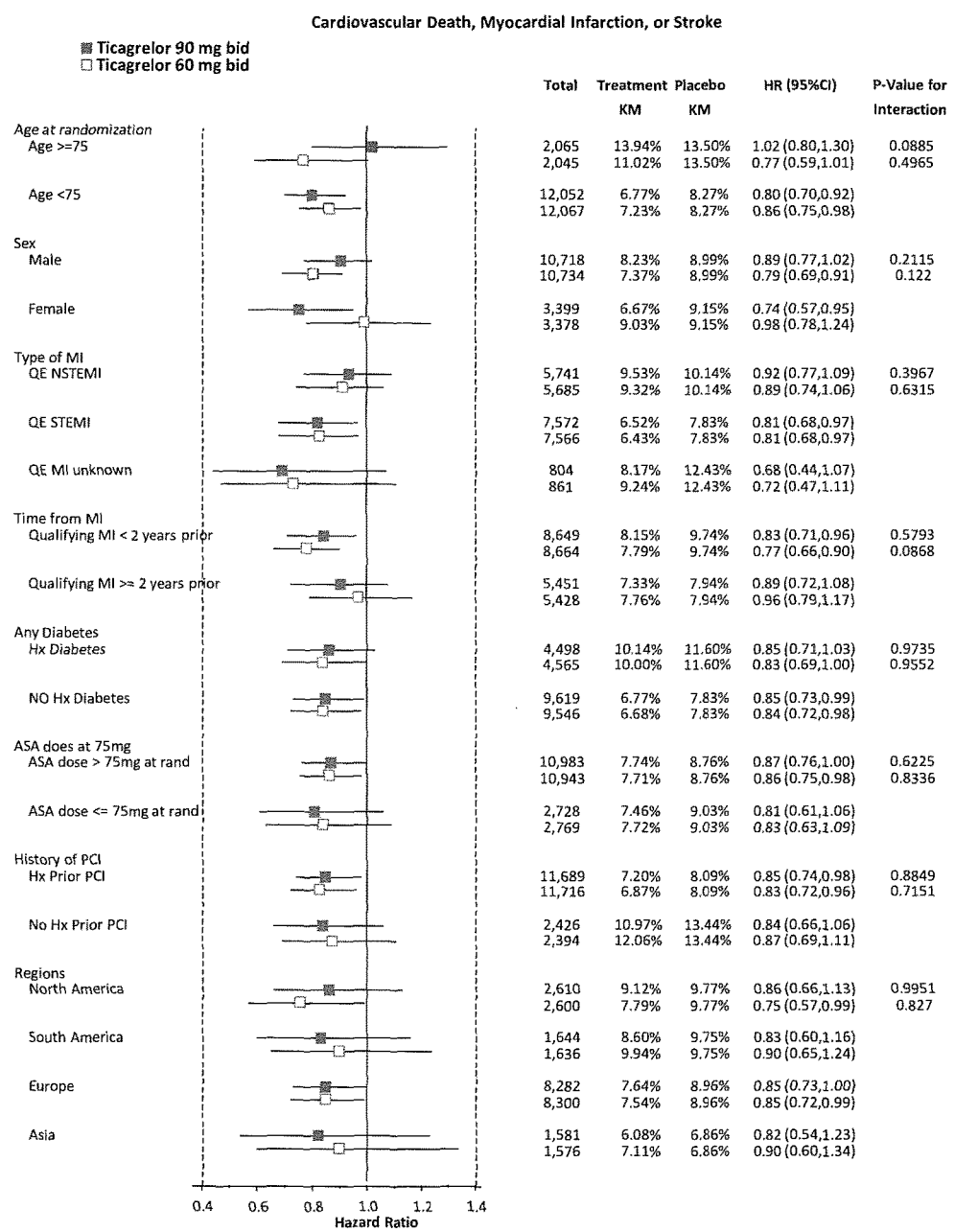
FIG. 5 depicts primary efficacy endpoint subgroup analyses in the PEGASUS-TIMI 54 trial.
Figure 6:
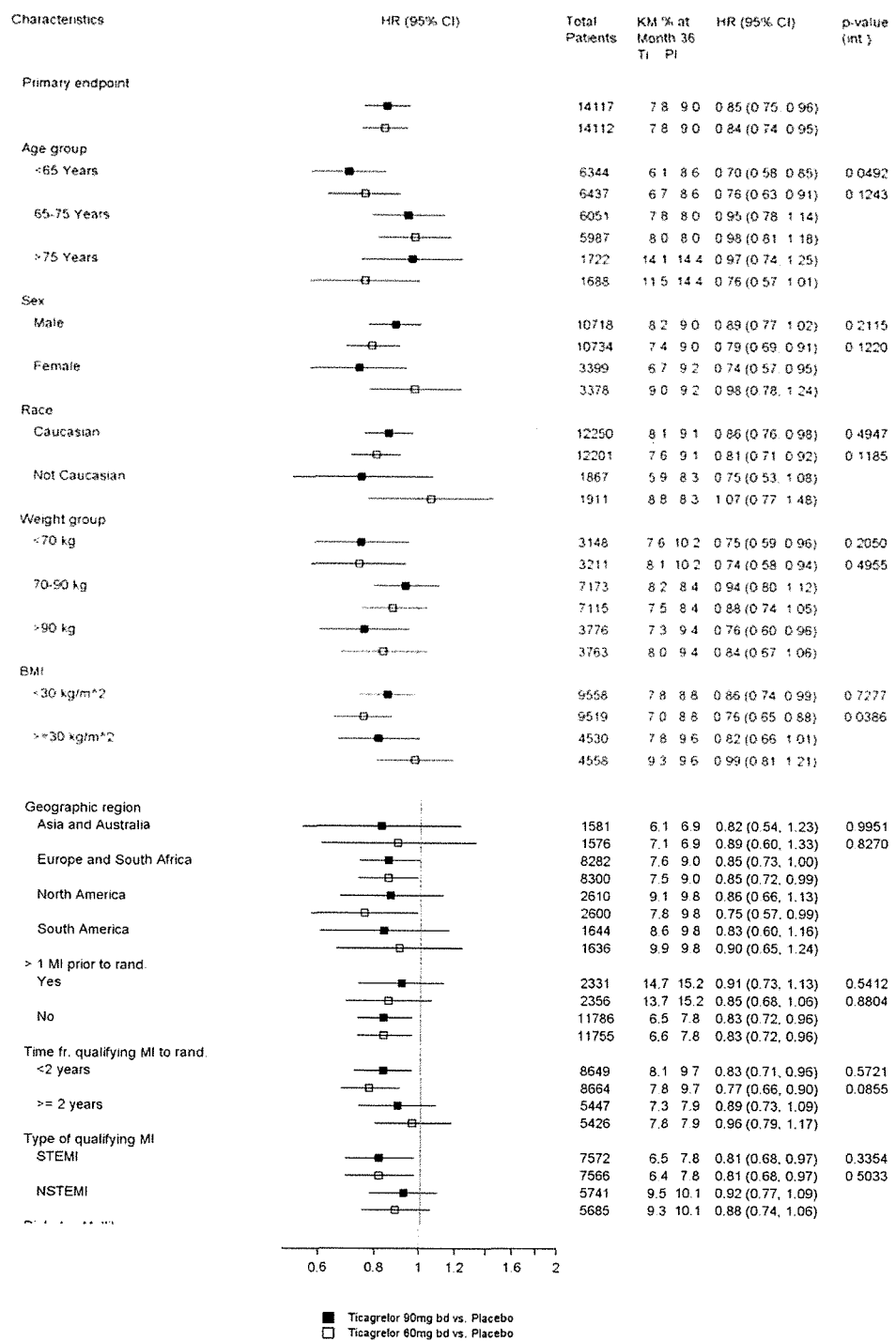
FIG. 6 depicts primary efficacy endpoint subgroup analyses in the PEGASUS-TIMI 54 trial.
Figure 7:
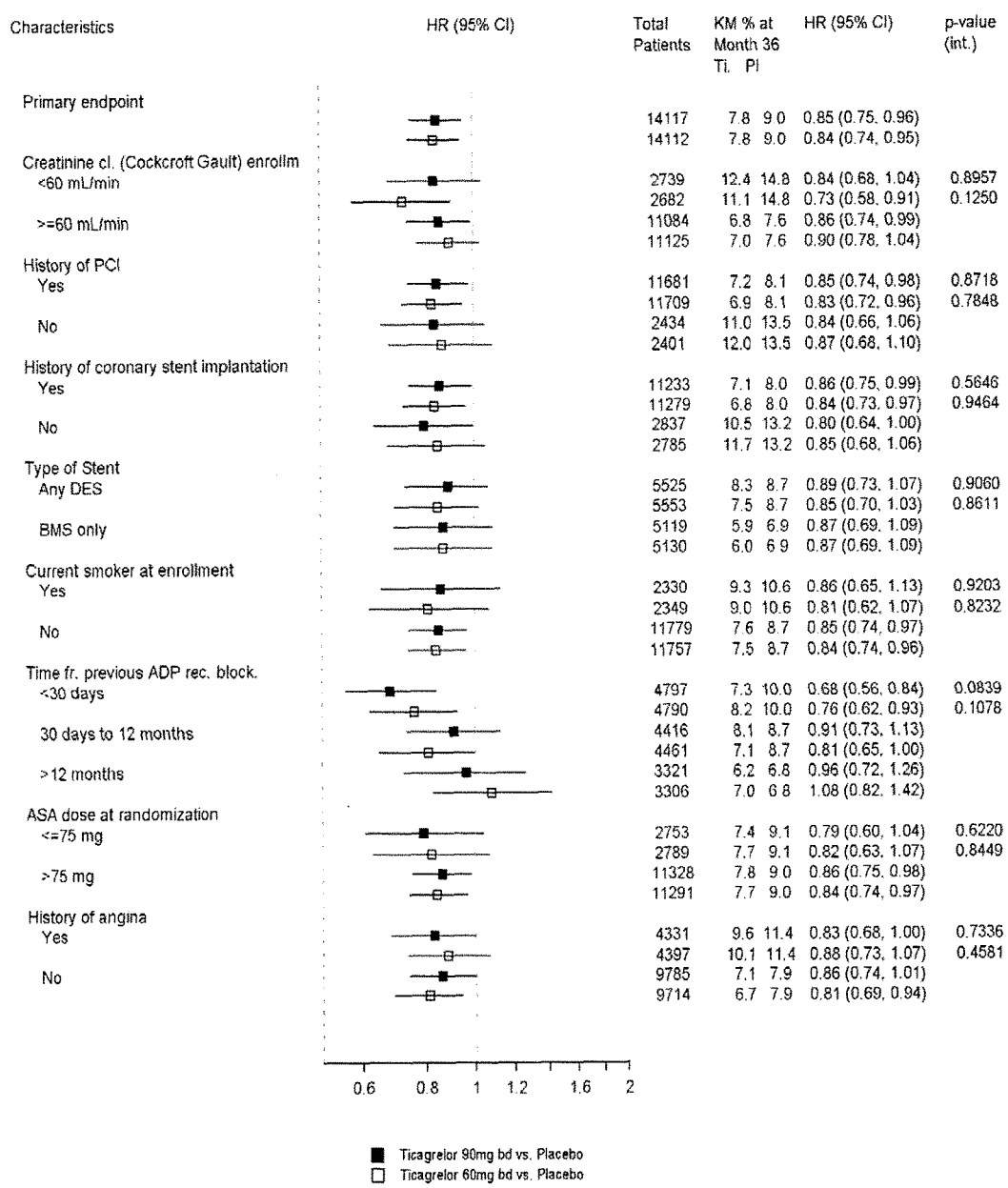
FIG. 7 depicts primary efficacy endpoint subgroup analyses of ticagrelor 60 mg bid in PEGASUS-TIMI 54 trial.

There was no apparent heterogeneity in the efficacy of ticagrelor at either dose on the rate of the primary composite endpoint across major subgroups including age, sex, index myocardial infarction type, time from qualifying myocardial infarction, diabetes, aspirin dose, history of percutaneous intervention, and region of randomization (FIG. 4). Additional subgroups are shown in FIGS. 5, 6, and 7, and efficacy data for ticagrelor stratified by aspirin dose is shown in Table 11.

TABLE 11

Efficacy Endpoint of Cardiovascular Death, Myocardial Infarction, or Stroke, Stratified by Post-Randomization Aspirin Dose

| Aspirin Dose Post-Randomization | | Ticagrelor 90 mg bid N = 7050 n (%) | Ticagrelor 60 mg bid N = 7045 n (%) | Placebo N = 7067 n (%) |
|---|---|---|---|---|
| ≤100 mg | n | 6851 | 6850 | 6881 |
| | Patients with events | 474 (6.9%) | 466 (6.8%) | 555 (8.1%) |
| | KM % | 7.89% | 7.6% | 8.9% |
| | HR (95% CI) | 0.85 (0.75, 0.96) | 0.84 (0.74, 0.95) | |
| | p-value | 0.0110 | 0.0046 | |
| >100 mg | n | 198 | 191 | 185 |
| | Patients with events | 19 (9.6%) | 21 (11.0%) | 23 (12.4%) |
| | KM % | 9.8% | 12.1% | 13.7% |
| | HR (95% CI) | 0.76 (0.42, 1.40) | 0.89 (0.49, 1.60) | |
| | p-value | 0.3849 | 0.6889 | |

The absolute risk reductions for the treatment arms (ticagrelor plus aspirin) vs. aspirin alone at three years were 1.27% in the ticagrelor 60 mg bid arm and 1.19% in the 90 mg bid arm. The relative risk reduction (RRR) for the composite endpoint of cardiovascular disease, myocardial infarction, or stroke from 1 to 360 days (17% RRR) and from 361 days and onwards (16% RRR) were similar for the ticagrelor 60 mg bid arm compared to placebo. In addition, the hazard ratio for the composite endpoint of cardiovascular disease, myocardial infarction, or stroke from 1 to 360 days (0.83) and from 361 days and onwards (0.84) were similar for the ticagrelor 60 mg bid arm relative to the placebo arm (Table 12). The superior treatment effect of ticagrelor was consistent throughout the study as evidenced by the Kaplan-Meier plot of cardiovascular death, myocardial infarction, and stroke through 3 years (FIG. 2A, FIG. 3), where the curves for the ticagrelor arms started to separate from the curve for the placebo arm following randomization and continued to separate throughout the study.

Figure 8:
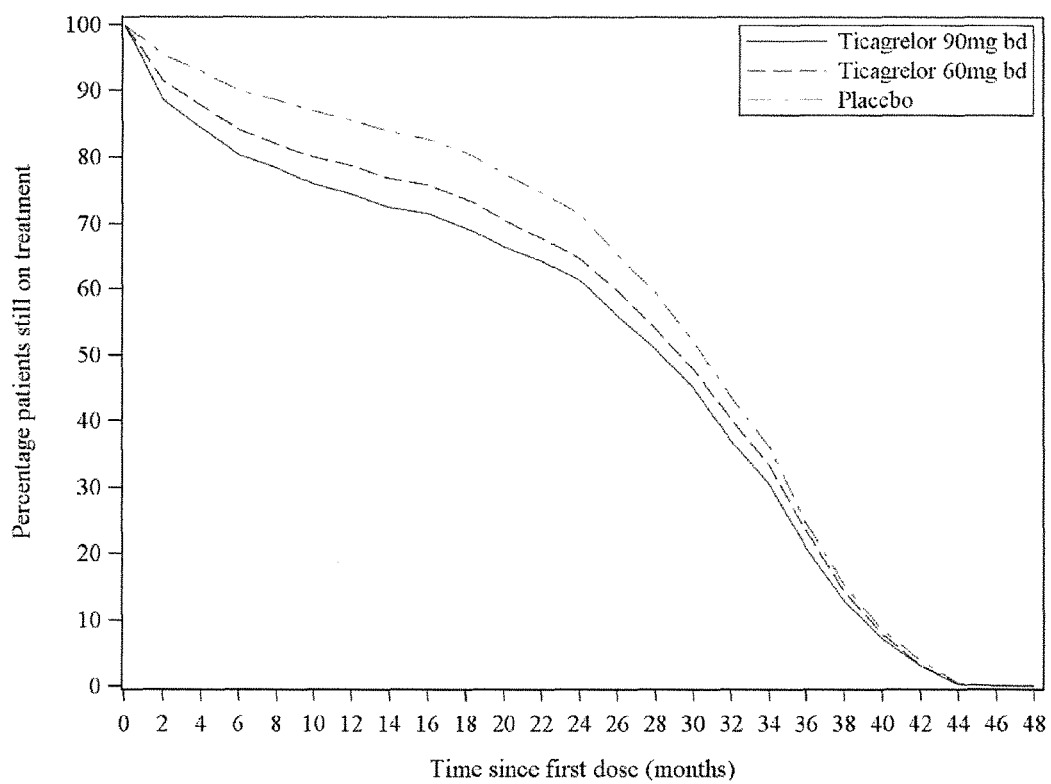
FIG. 8 depicts the percentage of patients still on treatment over time in the safety analysis set in the PEGASUS-TIMI 54 trial.

Patients in the ticagrelor 60 mg bid arm received study drug for up to 48 months (FIG. 8). For the ticagrelor 90 mg bid, ticagrelor 60 mg bid, and placebo arms, mean total duration of exposure to study drug (first dose to last dose) was 23.9, 25.3, and 27.3 months, respectively; median total duration of exposure was 28.3, 29.4, and 30.4 months, respectively. The higher proportion of patients prematurely permanently discontinued from study drug in both the ticagrelor arms relative to the placebo arm resulted in lower mean and median total duration of exposure in the ticagrelor arms. The superior treatment effect of ticagrelor over time suggests that it may be appropriate to continue treatment with ticagrelor as long as the patient remains at high risk of an atherothrombotic event.

Figure 9:
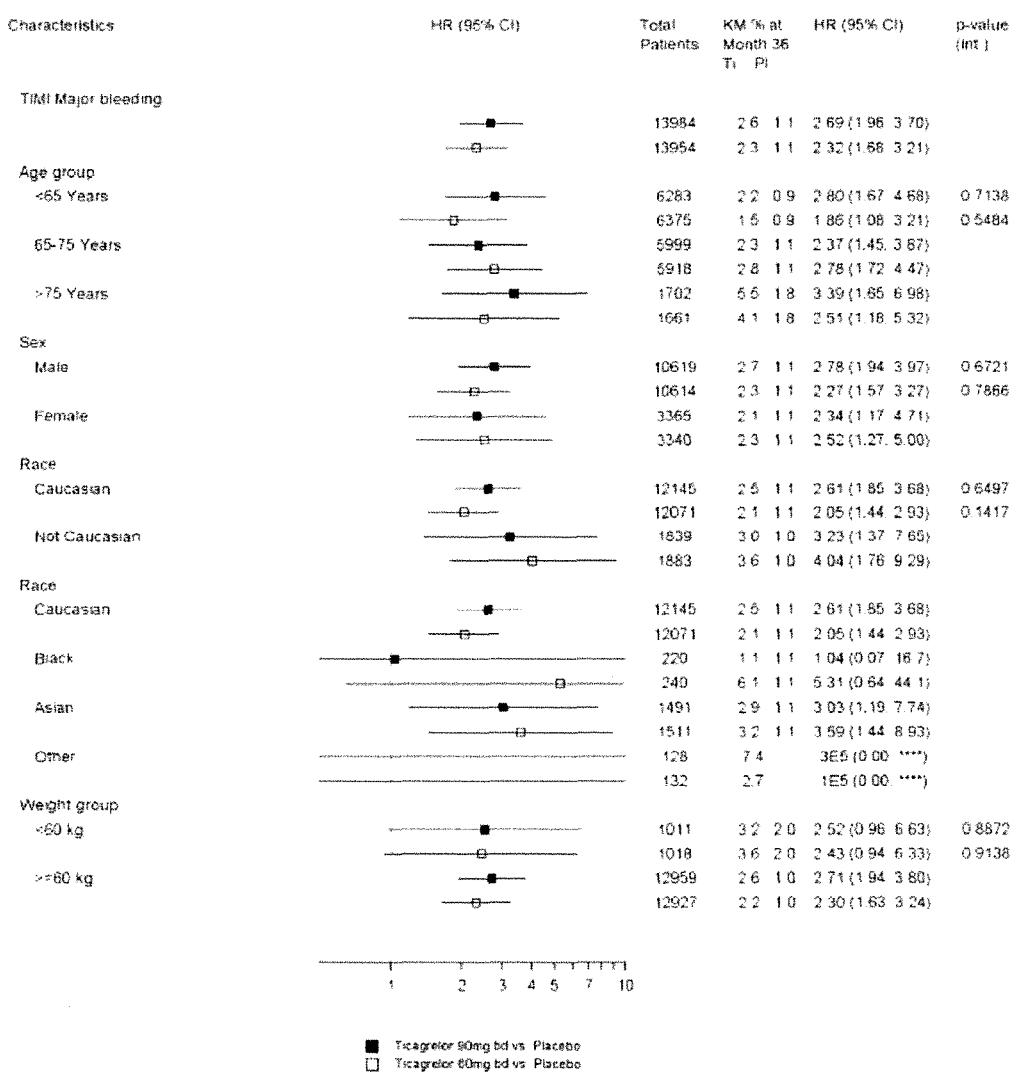
FIG. 9 depicts TIMI major bleeding—subgroups in the PEGASUS-TIMI 54 study.
Figure 10:
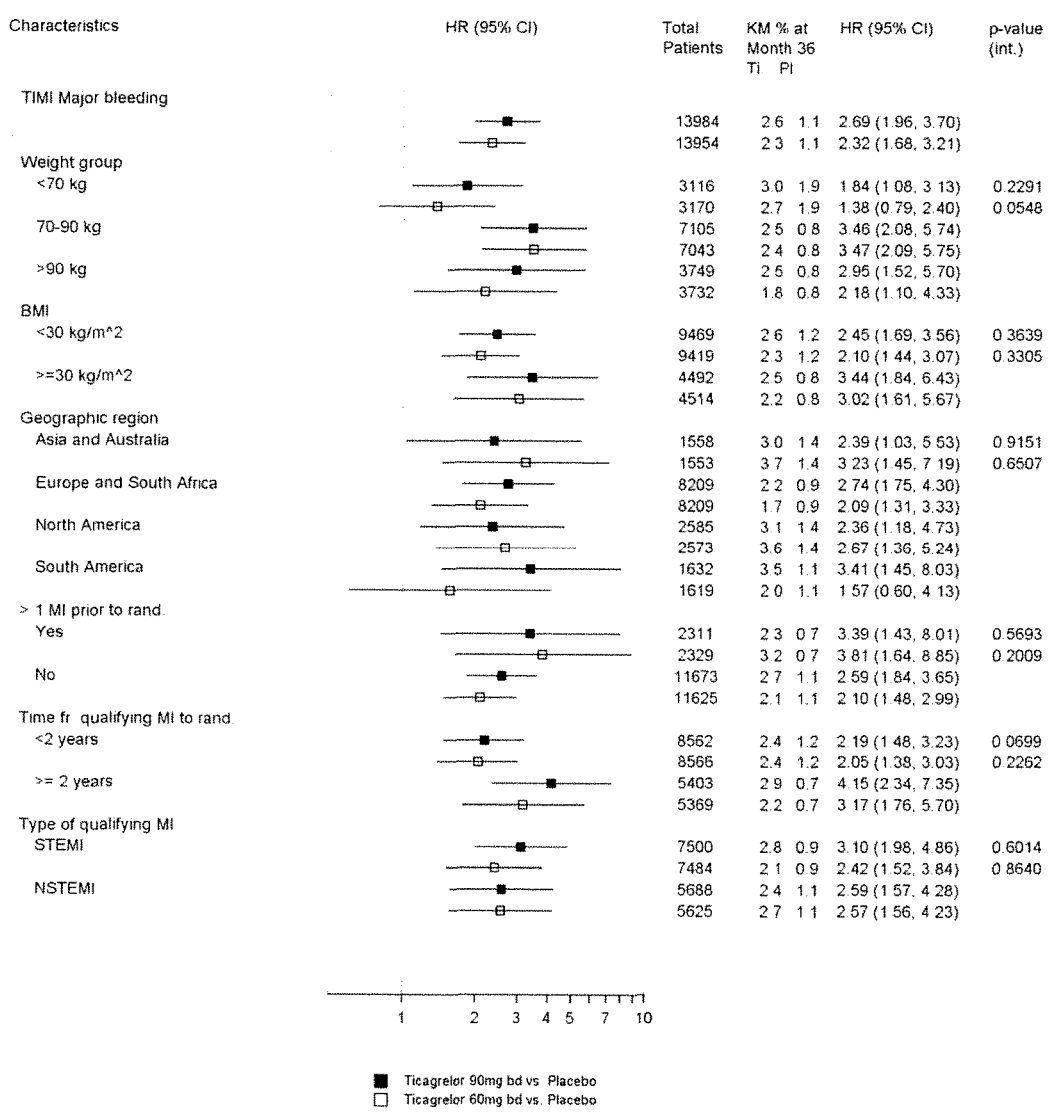
FIG. 10 depicts TIMI major bleeding—subgroups in the PEGASUS-TIMI 54 study.
Figure 11:
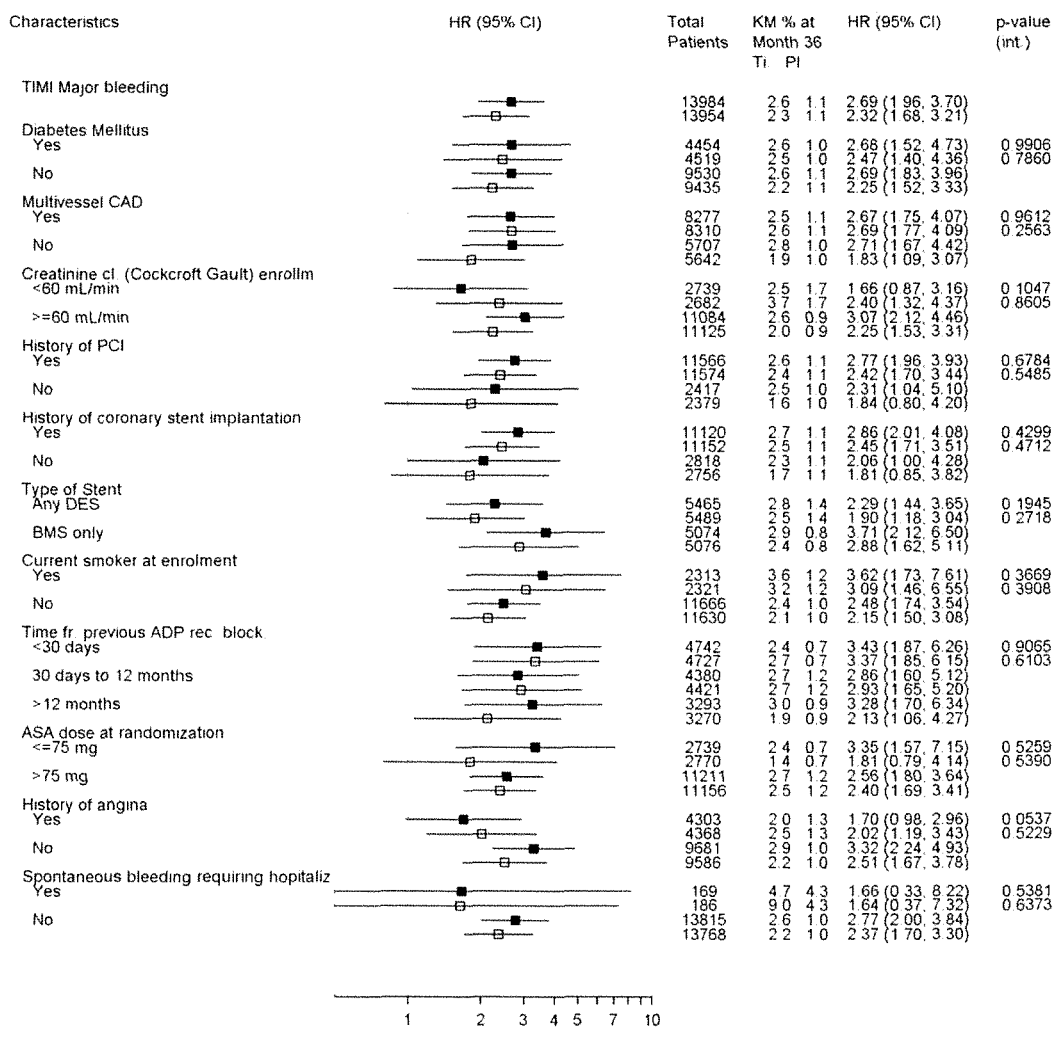
FIG. 11 depicts TIMI major bleeding—subgroups in the PEGASUS-TIMI 54 study.

The primary safety endpoint of TIMI major bleeding was higher with both doses of ticagrelor compared to placebo, with rates at 3 years of 2.60% in the ticagrelor 90 mg bid arm, 2.30% in the ticagrelor 60 mg bid arm, and 1.06% in the placebo arm (HR for ticagrelor 90 BID vs placebo 2.69, 95% CI 1.96-3.70, p<0.001; HR for ticagrelor 60 BID vs placebo 2.32, 95% CI 1.68-3.21, p<0.001, Table 14) with no apparent heterogeneity among major subgroups (FIGS. 9-11).

TABLE 12

Landmark analysis of primary clinical endpoint (full analysis set)

| Characteristic | Time Interval | | Ticagrelor 90 mg bd | Ticagrelor 60 mg bd | Placebo |
|---|---|---|---|---|---|
| Composite of CV Death/MI/Stroke | 1-360 days | n | 7050 | 7045 | 7067 |
| | | Patients with events | 198 (2.8%) | 189 (2.7%) | 227 (3.2%) |
| | | KM % at 12 months | 2.8% | 2.7% | 3.2% |
| | | Hazard Ratio (95% CI) | 0.87 (0.72, 1.06) | 0.83 (0.69, 1.01) | |
| | 361 days or more | n[a] | 6768 | 6783 | 6760 |
| | | Patients with events | 295 (4.4%) | 298 (4.4%) | 351 (5.2%) |
| | | KM % at 24 months[b] | 2.4% | 2.7% | 3.0% |
| | | KM % at 36 months[b] | 5.2% | 5.2% | 6.0% |

TABLE 12-continued

Landmark analysis of primary clinical endpoint (full analysis set)

| Characteristic | Time Interval | | Ticagrelor 90 mg bd | Ticagrelor 60 mg bd | Placebo |
|---|---|---|---|---|---|
| | Hazard Ratio (95% CI) | | 0.84 (0.72, 0.98) | 0.84 (0.72, 0.98) | |

Source: CSR Table 11.2.4.5
[a] Only patients who are event-free in the first period (days 1-360) are included in the second period (day 361 and onwards).
[b] Cumulative percentage from day 1 to 360 days after randomisation, and from day 361 to day 720 and 1080 respectively.
Hazard ratios are calculated separately for each ticagrelor dose vs placebo from Cox proportional hazards model with treatment group as the only explanatory variable
CI Confidence interval;
HR Hazard ratio;
KM Kaplan-Meier;
n Number of patients in category or analysis;
N Number of patients in treatment group

TABLE 13

Cumulative Exposure Over Time (Safety Analysis Set)

| Time on Study Drug[a] | Ticagrelor 90 mg bd (N = 6988) | Number(%) of patients Ticagrelor 60 mg bd (N = 6958) | Placebo (N = 6996) |
|---|---|---|---|
| 0 days | 6988 (100%) | 6958 (100%) | 6996 (100%) |
| 1 day | 6988 (100%) | 6958 (100%) | 6996 (100%) |
| 30 days | 6434 (92.1%) | 6527 (93.8%) | 6799 (97.2%) |
| 4 months | 5899 (84.4%) | 6110 (87.8%) | 6505 (93.0%) |
| 8 months | 5476 (78.4%) | 5705 (82.0%) | 6204 (88.7%) |
| 12 months | 5203 (74.5%) | 5481 (78.8%) | 5992 (85.6%) |
| 18 months | 4842 (69.3%) | 5126 (73.7%) | 5643 (80.7%) |
| 24 months | 4291 (61.4%) | 4505 (64.7%) | 4996 (71.4%) |
| 30 months | 3142 (45.0%) | 3328 (47.8%) | 3653 (52.2%) |
| 36 months | 1445 (20.7%) | 1620 (23.3%) | 1716 (24.5%) |
| 42 months | 216 (3.1%) | 222 (3.2%) | 270 (3.9%) |

Source: CSR Table 11.3.1.2.2
[a] Number of patients on treatment at the start of the interval.
Percentages are based on the total numbers of patients in the treatment group (N).
This table is based on total duration from first dose date to last dose date.
bd Twice daily The rate of fatal bleeding or non-fatal intracranial hemorrhage was not notably different, i.e., had very small differences, between treatment arms (Table 14). The number of fatal bleeding events was low, corresponding to Kaplan-Meier rates at 36 months of 0.1% (n=6), 0.3% (n=11), and 0.3% (n=12) for the ticagrelor 90 mg bid, ticagrelor 60 mg bid, and placebo arms, respectively. Similarly, there were few incidences of intracranial hemorrhage, corresponding to Kaplan-Meier rates at 36 months of 0.6% (n=29), 0.6% (n=28), and 0.5% (n=23) for the ticagrelor 90 mg bid, ticagrelor 60 mg bid, and placebo arms, respectively. The TIMI minor bleeding and bleeding leading to transfusion was similarly increased with ticagrelor versus placebo (Table 3). The rates of bleeding leading to transfusion were 2.4% for ticagrelor 90 mg, 2.1% for ticagrelor 60 mg and 0.7% for placebo (P<0.001 for each dose versus placebo).

"Other TIMI major bleeding," while important due to their potential to cause morbidity and increased care requirements, are manageable clinically and do not cause irreversible harm.

Figure 12:
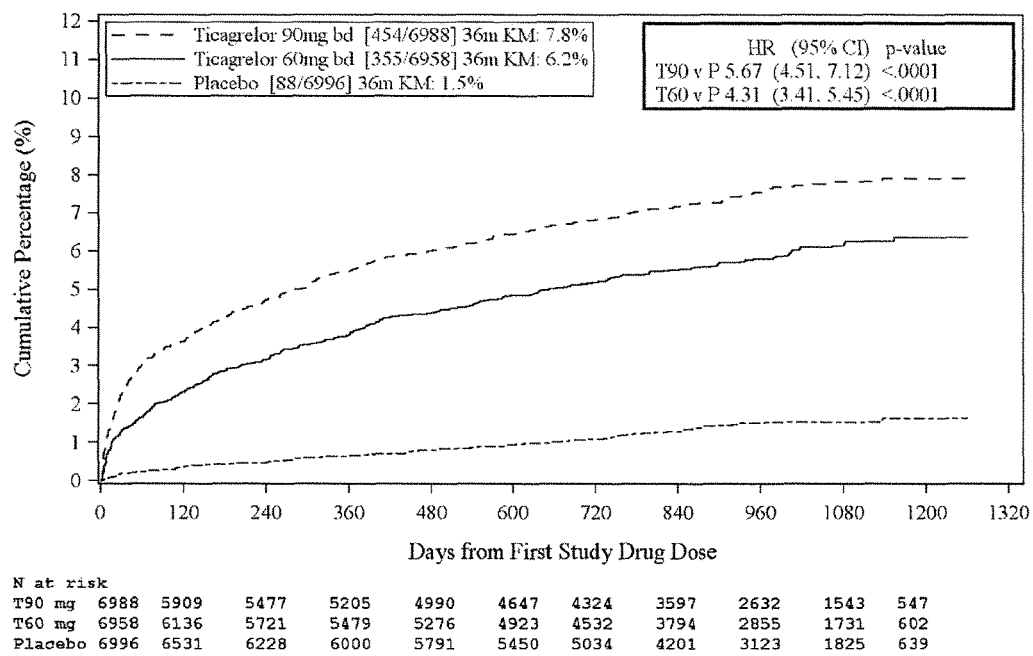
FIG. 12 depicts a Kaplan-Meier estimate of time to premature permanent discontinuation of study drug due to bleeding based on the safety analysis set.

Premature treatment discontinuation for bleeding was higher with both doses of ticagrelor compared to placebo at 7.8% for ticagrelor 90 mg bid, 6.2% for ticagrelor 60% bid, and 1.5% for placebo (Table 14). FIG. 12 shows a Kaplan-Meier estimate of time to premature permanent discontinuation of study drug due to bleeding based on the safety analysis set. Overall outcome of bleeding events in the PEGASUS-TIMI 54 trial are shown in Table 15.

However, the ticagrelor arms showed a trend toward reduced fatal bleeding rate compared to the placebo arm, with 6 and 11 fatal bleeding incidents in the 90 mg and 60 mg ticagrelor arms, respectively, versus 12 fatal bleeding incidents in the placebo arm. In particular, the ratio of fatal bleeding events over TIMI major bleeding events in each ticagrelor experimental arm (6/127, i.e., about 1/21, for 90 mg arm and 11/115, i.e, about 1/10, for 60 mg arm) is much less than that in the placebo comparator arm (12/54, i.e., 1/4.5). Overall, absolute bleeding rates are in line with what has been observed in other long-term dual antiplatelet therapy trials.

Dyspnea was more frequent with both doses of ticagrelor, with 3-year event rates of 18.9% in patients in the ticagrelor 90 mg bid arm, 15.8% in patients in the ticagrelor 60 mg bid arm, and 6.4% in patients in the placebo arm (P<0.001 for each dose versus placebo, Table 3). The median duration of resolved dyspnea adverse events was 22, 31, and 49 days in the ticagrelor 90 mg bid arm, ticagrelor 60 mg bid arm, and placebo arm, respectively. The frequency of dyspnea and the median duration of resolved dyspnea adverse events were numerically lower for patients in the ticagrelor 60 mg bid arm relative to the ticagrelor 90 mg bid arm. The majority of dyspneic episodes with either dose of ticagrelor were characterized as either mild (57%) or moderate (38%) in severity, and dyspnea as a serious adverse event in patients on ticagrelor was infrequent (3-year rate 0.3%). Regardless of treatment group, the majority of patients with dyspnea adverse events had only one episode. The rates of dyspnea leading to study drug discontinuation were 6.5% with ticagrelor 90 mg bid, 4.3% with ticagrelor 60 mg bid, and 0.7% with placebo (P<0.001 for each dose versus placebo, Table 3). In a substudy of PLATO in which 199 subjects underwent pulmonary function testing irrespective of whether they reported dyspnea, there was no indication of an adverse effect on pulmonary function assessed after one month or after at least 6 months of chronic treatment.

TABLE 14

Safety and Tolerability Endpoints

| End Point | Ticagrelor 90 mg bid (N = 6988) n (%) | Ticagrelor 60 mg bid (N = 6958) n (%) | Placebo (N = 6996) n (%) | Ticagrelor 90 mg bid vs Placebo HR (95% CI) p-value | Ticagrelor 60 mg bid vs Placebo HR (95% CI) p-value |
|---|---|---|---|---|---|
| Bleeding | | | | | |
| TIMI Major | 127 (2.60) | 115 (2.30) | 54 (1.06) | 2.69 (1.96-3.70) P < 0.001 | 2.32 (1.68-3.21) P < 0.001 |
| TIMI Minor | 66 (1.31) | 55 (1.18) | 18 (0.36) | 4.15 (2.47-7.00) P < 0.001 | 3.31 (1.94-5.63) P < 0.001 |
| Bleeding requiring transfusion | 122 (2.40) | 105 (2.10) | 37 (0.70) | 3.75 (2.59-5.42) P < 0.001 | 3.08 (2.12-4.48) P < 0.002 |
| Leading to study drug discontinuation | 454 (7.80) | 355 (6.2) | 88 (1.5) | 5.67 (4.51-7.12) P < 0.001 | 4.31 (3.41-5.45) P < 0.001 |
| Fatal bleeding or non-fatal intracranial hemorrhage | 33 (0.71) | 32 (0.63) | 30 (0.60) | 1.20 (0.73-1.97) p = 0.47 | 1.22 (0.74-2.01) p = 0.43 |
| Intracranial Hemorrhage | 29 (0.56) | 28 (0.61) | 23 (0.47) | 1.44 (0.83-2.49) P = 0.19 | 1.33 (0.77-2.31) P = 0.31 |
| Fatal Bleeding | 6 (0.11) | 11 (0.25) | 12 (0.26) | 0.58 (0.22-1.54) P = 0.27 | 1.00 (0.44-2.27) P = 1.00 |
| Other Adverse Events | | | | | |
| Dyspnea AE | 1204 (17.22) | 986 (14.17) | 382 (5.46) | 3.55 (3.17-3.99) P < 0.001 | 2.82 (2.50-3.17) P < 0.001 |
| Leading to study drug discontinuation | 430 (6.2) | 296 (4.3) | 51 (0.7) | 8.89 (6.65-11.88) P < 0.001 | 6.35 (4.84-8.12) P < 0.001 |
| SAE | 22 (0.3) | 22 (0.3) | 8 (0.1) | 3.02 (1.34-6.78) p = 0.0075 | 2.91 (1.30-6.54) p = 0.0097 |
| Renal adverse event | 166 (2.4) | 173 (2.5) | 161 (2.3) | | |
| Bradyarrythmia adverse event | 105 (1.5) | 121 (1.7) | 105 (1.5) | | |
| Gout adverse event | 99 (1.4) | 97 (1.4) | 70 (1.0) | | |

Rates are presented as 3-year Kaplan-Meier estimates

TABLE 15

Bleeding Events

| | Ticagrelor 60 mg bid (N = 6958) | | Placebo (N = 6996) | |
|---|---|---|---|---|
| | n (%) patients with event | Events/ 100 pt yrs | n (%) patients with event | Events/ 100 pt yrs |
| TIMI Major | 115 (1.7) | 0.78 | 54 (0.8) | 0.34 |
| Fatal | 11 (0.2) | 0.08 | 12 (0.2) | 0.08 |
| Intracranial hemorrhage | 28 (0.4) | 0.19 | 23 (0.3) | 0.14 |
| TIMI Major or Minor | 168 (2.4) | 1.15 | 72 (1.0) | 0.45 |

There were no notable differences in the rates of renal, hepatic, bradyarrythmic, or gout adverse events, and no liver or kidney related issues were identified during the PEGASUS trial (Table 14). Frequencies of pre-defined bradyarrhythmic AEs were similar across treatment groups. PLATO and PEGASUS excluded patients at increased risk of bradycardic events (e.g., patients who have sick sinus syndrome, 2nd or 3rd degree AV block, or bradycardic-related syncope and not protected with a pacemaker). An assessment of adverse events possibly related to bradyarrhythmia showed that dizziness, hypotension and syncope were more frequently reported in the ticagrelor 90 mg bid and ticagrelor 60 mg bid arms compared with the placebo arms. In the PEGASUS trial, syncope was reported by 1.2% and 0.9% of patients on 60 mg ticagrelor bid and placebo, respectively.

In addition, a reversible increase in serum uric acid levels consistent with previous findings was observed during the PEGASUS trial. In the PLATO trial, serum uric acid levels increased approximately 0.6 mg/dL from baseline for patients administered ticagrelor 90 mg bid compared to an approximately 0.2 mg/dL increase from baseline for patients administered clopidogrel. The difference in serum uric acid levels observed during the PLATO trial disappeared within 30 days of discontinuing treatment. Moreover, reports of gout did not differ between treatment groups in PLATO (0.6% in each group). During the PEGASUS trial, it was observed that serum uric acid levels increased approximately 0.2 mg/dL from baseline for patients administered ticagrelor 60 mg bid. No elevation in serum uric acid levels was observed in the placebo arm. Gout occurred more commonly in patients in the experimental arm (1.5%) than in the placebo arm (1.1%), and there were no reports of urate nephropathy. Hypotension occurred more commonly in patients in the ticagrelor 60 mg bid (0.66 events/100 patient (pt) years) and ticagrelor 90 mg bid (0.66 events/100 pt years) arms relative to the placebo arm (0.45 events/100 pt years).

In the PEGASUS trial, mean serum uric acid concentrations decreased after treatment was stopped. Furthermore, in the PEGASUS-TIMI 54 trial, serum creatinine concentration increased by >50% in approximately 4% of patients administered 60 mg ticareglor bid, which was comparable to the increase observed in patients in the placebo arm. There was no evidence that the increase in serum creatinine in the ticagrelor treatment groups is related to renal impairment. In addition, the frequency of renal related adverse events was similar for ticagrelor and aspirin alone regardless of age and baseline renal function. Rates of adverse events and serious adverse events are listed in Table 16. Rates of adverse events that occurred in the PEGASUS trial at rates of 3% or more are shown in Table 17.

TABLE 16

Adverse Events

| Adverse Event | Ticagrelor 90 mg bid (N = 6988) n (%) | Ticagrelor 60 mg bid (N = 6958) n (%) | Placebo (N = 6996) n (%) |
|---|---|---|---|
| Any adverse event | 5327 (76.2) | 5268 (75.7) | 4837 (69.1) |
| Leading to discontinuation of study drug | 1306 (18.7) | 1117 (16.1) | 596 (8.5) |
| Leading to death | 161 (2.3) | 149 (2.1) | 203 (2.9) |
| Any serious adverse event | 1514 (21.7) | 1499 (21.5) | 1511 (21.6) |
| Leading to discontinuation of study drug | 256 (3.7) | 255 (3.7) | 211 (3.0) |
| Non-Cardiovascular death | 142 (2.0) | 113 (1.6) | 111 (1.6) |
| Death | 326 (4.6) | 289 (4.1) | 326 (4.6) |

Nb, mortality data analyzed in the intention-to-treat population.

TABLE 17

Non-hemorrhagic Adverse Reactions Reported in >3.0% of Patients

|  | Ticagrelor 60 mg bid (N = 6958) | Placebo (N = 6996) |
|---|---|---|
| Dyspnea | 14.2 | 5.5 |
| Dizziness | 4.5 | 4.1 |
| Diarrhea | 3.3 | 2.5 |

Patients who have had a myocardial infarction remain at heightened risk of ischemic events over the long-term. Results of the PEGASUS clinical trial showed that the addition of the $P2Y_{12}$ receptor antagonist ticagrelor to low-dose aspirin in such patients reduces the risk of cardiovascular death, myocardial infarction or stroke significantly. The benefit of ticagrelor was consistent, among major clinical subgroups, and by region, consistent among the individual fatal and non-fatal components of the primary endpoint and continued to accrue over time.

The results of the PEGASUS clinical trial were used to develop an exposure response model for the ticagrelor 60 mg bid, ticagrelor 90 mg bid, and placebo arms. The influence of risk factors (RFs) associated with the composite endpoint of cardiovascular death, myocardial infarction, and stroke and the safety endpoint of TIMI major bleeding were evaluated using an RF model developed for the placebo data. The RF model was then used on all treatment groups to evaluate the hazard associated with each risk factor in patients treated with ticagrelor 60 mg bid or ticagrelor 90 mg bid. Risk factors included in the analysis were age, serum creatinine, body mass index, diabetes mellitus, hypertension, peripheral artery disease, history of more than one prior MI, qualifying STEMI event, history of unstable angina pectoris, dose of aspirin, race, gender, smoker status, ethnicity, coronary artery bypass grafting (CABG) during study, PCI during study, previous spontaneous bleeding requiring hospitalization, and left ventricular disease.

Figure 13:
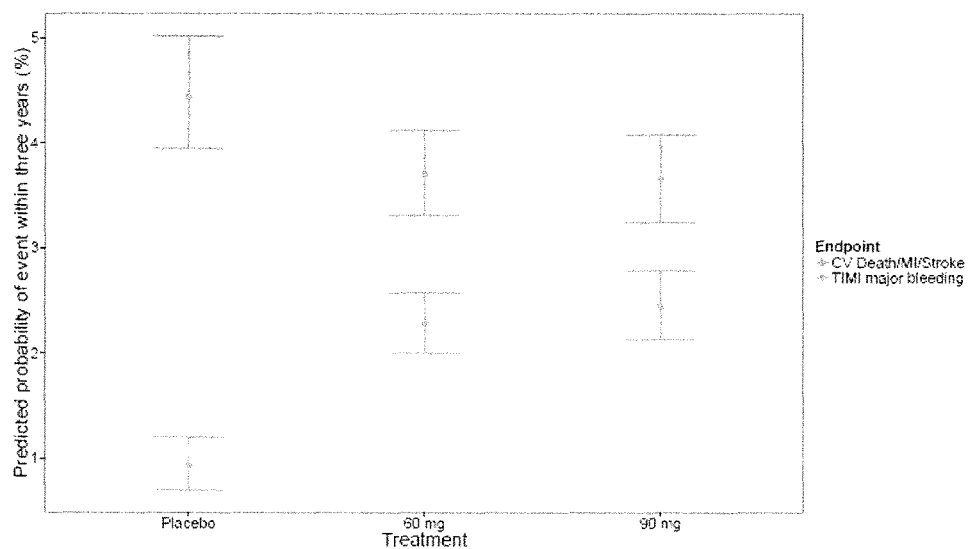
FIG. 13 depicts the predicted probability of a cardiovascular death, myocardial infarction, or stroke event and the predicted probability of a TIMI major bleeding event within three years using the final dose-exposure-response models, stratified by treatment arm.
Figure 14:
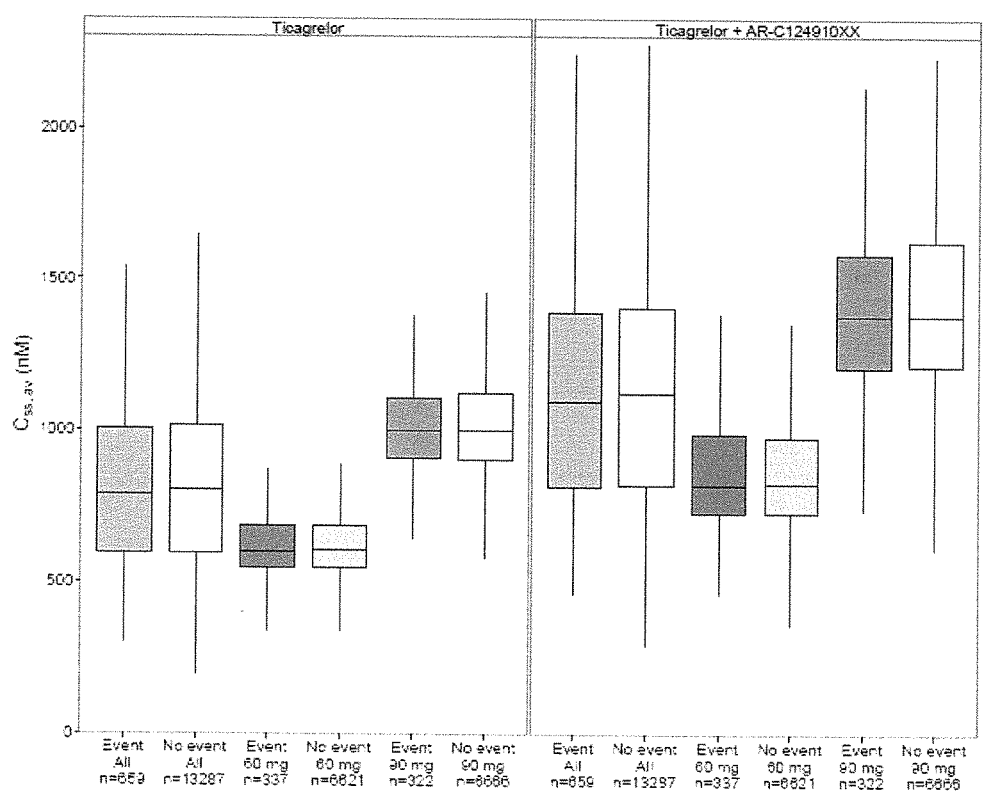
FIG. 14 depicts the composite endpoint of cardiovascular death, myocardial infarction, and stroke events/no events versus exposure using the final exposure-response analysis data set.
Figure 15:
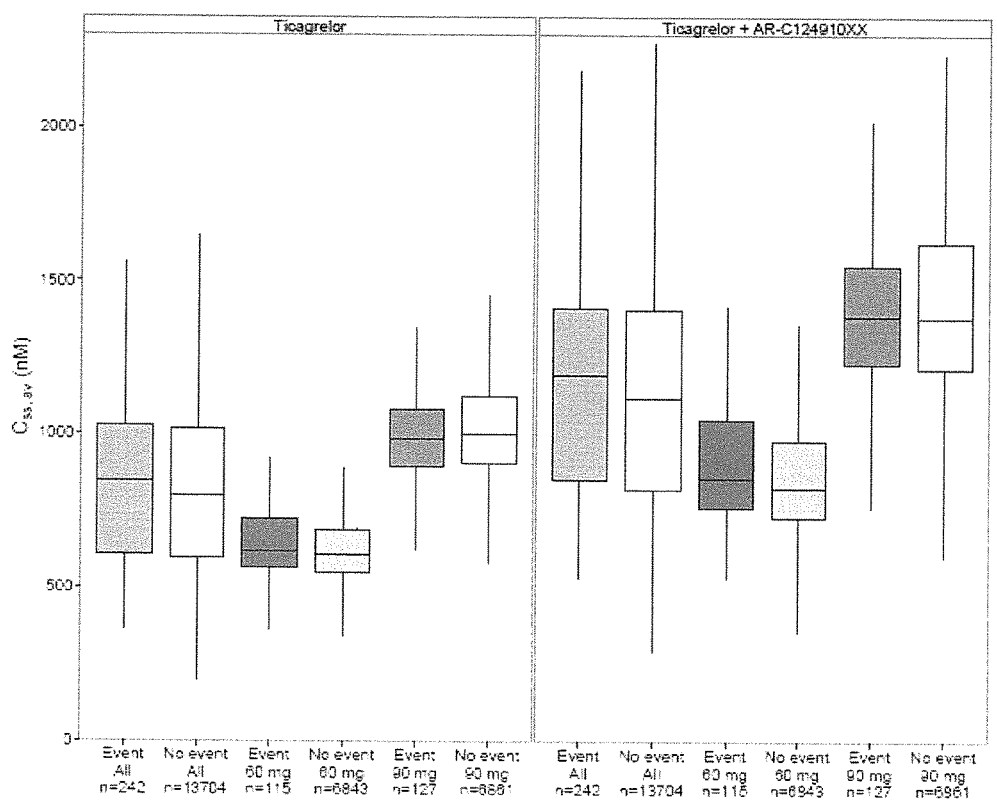
FIG. 15 depicts TIMI major bleeding events/no events versus exposure using the final exposure-response analysis data set.

In addition, potential dose-exposure-response relationships between plasma exposure of ticagrelor and the composite endpoint of cardiovascular death, myocardial infarction, and stroke and the safety endpoint of TIMI major bleeding, as well as potential covariate effects on the dose-exposure-response relationships, were investigated using exposure response modelling. FIG. 13 shows the predicted probability of a cardiovascular death, myocardial infarction, or stroke event and the predicted probability of a TIMI major bleeding event within three years using the final dose-exposure-response models, stratified by treatment arm. The average predicted probability of event in the placebo, ticagrelor 60 mg bid, ticagrelor 90 mg bid arms, were: 8.47%, 6.82% and 6.74% for cardiovascular death, myocardial infarction, or stroke events and 1.02%, 2.46% and 2.65% for TIMI major bleeding events. FIG. 14 depicts the composite endpoint of cardiovascular death, myocardial infarction, and stroke events/no events versus exposure using the final exposure-response analysis data set, and FIG. 15 depicts TIMI major bleeding events/no events versus exposure using the final exposure-response analysis data set.

Figure 16:
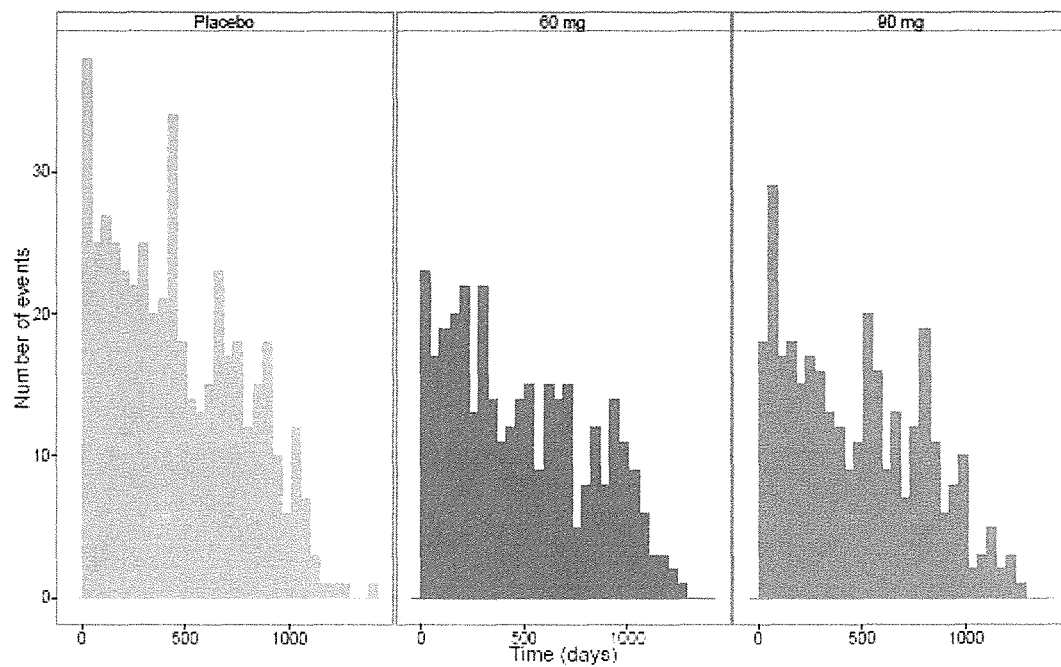
FIG. 16 depicts the distribution of cardiovascular death, myocardial infarction, and stroke event times, stratified by dose.

The cardiovascular death, myocardial infarction, or stroke events on treatment data generated in the PEGASUS-TIMI 54 clinical trial was also described by a parametric time-to-event model. FIG. 16 shows the distribution of cardiovascular death, myocardial infarction, and stroke event times, stratified by dose. The baseline hazard slightly decreased with time described by a Weibull distribution. A proportional hazards model was assumed when describing the influence of RFs and drug exposure.

The exposure response model developed from the PEGASUS study data demonstrated a similar and consistent benefit of ticagrelor across subgroups, with eight risk factors identified to increase the risk of the composite endpoint of cardiovascular death, myocardial infarction, or stroke in the placebo arm: age (hazard ratio (HR) of 1.03 per year above 65 years); serum creatinine (HR of 1.01 per μmol/L above 87 μmol/L); history of unstable angina pectoris (HR of 1.41); diabetes mellitus (HR of 1.58); peripheral artery disease (HR of 1.51); more than one previous MI (HR of 2.04); Hispanic/Latino ethnicity (HR of 1.33); and current smoker (HR of 1.43). No subgroup, apart from Japanese ethnicity, was statistically identified to be more or less sensitive to ticagrelor exposure after accounting for risk factors.

Based on the results of the exposure response model, there was a lower risk of event in Japanese patients compared to the overall population (e.g. a HR of 0.29 for a Japanese patient with a median exposure in the 60 mg group (606 nM) compared to placebo and a HR of 0.83 for a non-Japanese patient with median exposure in the 60 mg group (606 nM) compared to placebo). The observed lower risk of event in Japanese patients may be due to a lower underlying risk, Japanese patients being more sensitive to ticagrelor exposure or a combination of both. However, there was limited data (20 events in 901 patients) in the Japanese population.

The estimated exposure-response relationship was flat, indicating close to maximum response. The average concentration of ticagrelor at steady state ($c_{ss,av}$) exposure was a slightly stronger predictor of event over the studied exposure range compared to a pooled general ticagrelor treatment effect for 60 and 90 mg doses.

Figure 17:
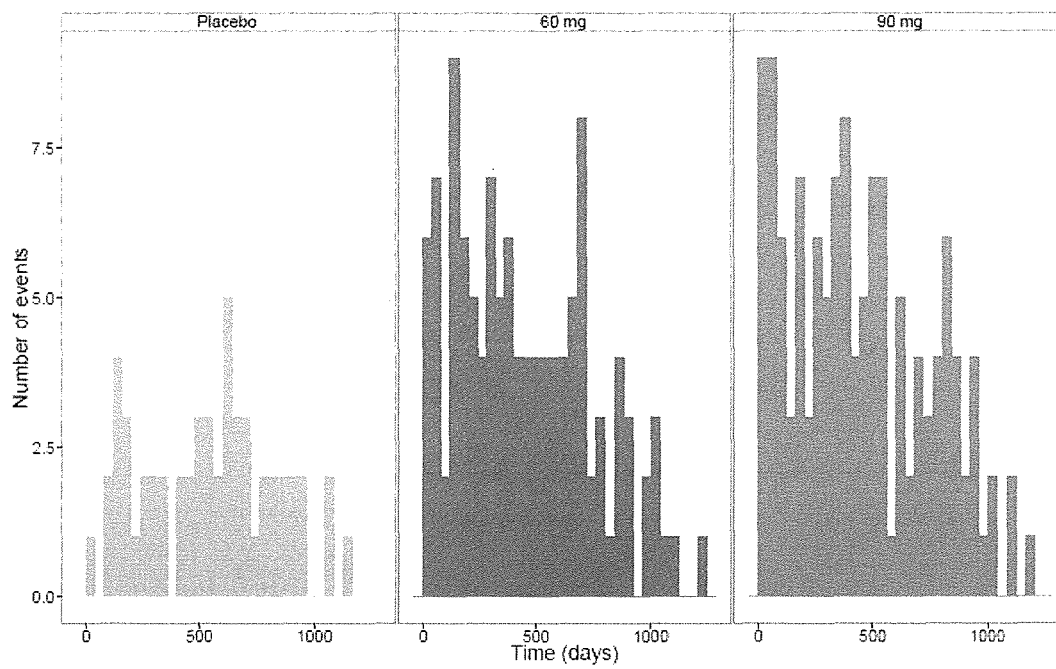
FIG. 17 depicts the distribution of TIMI major bleeding event times, stratified by dose.

The TIMI major bleeding on treatment data in the PEGASUS-TIMI 54 clinical trial was further described by a parametric time-to-event model. FIG. 17 shows the distribution of TIMI major bleeding event times, stratified by dose. The baseline hazard was constant over time described by an Exponential distribution. A proportional hazards model was assumed when describing the influence of risk factors and drug exposure. Only two risk factors were identified for TIMI major bleeding: age (increased risk with increasing age with a HR of 1.04 per year above 65 years) and coronary artery bypass grafting (CABG) (temporary effect up to 7 days after procedure with a HR of 575).

Figure 18:
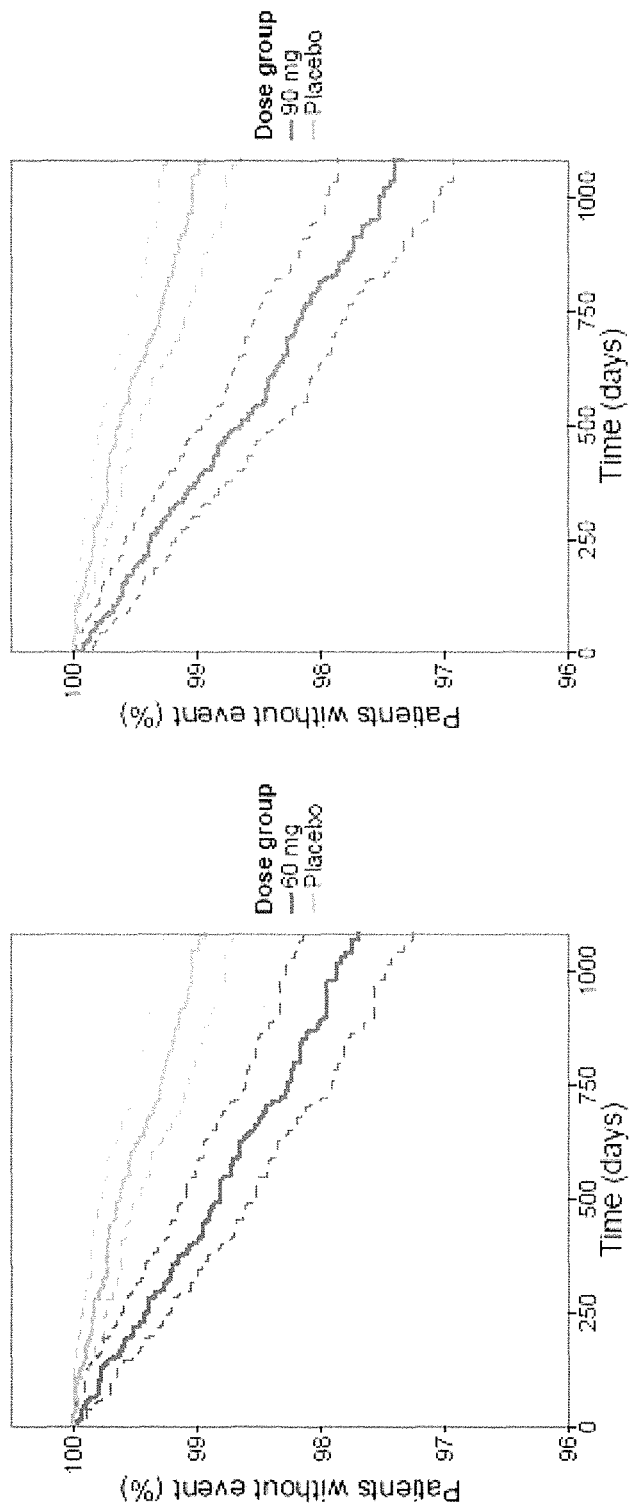
FIG. 18 depicts Kaplan-Meier estimates of patients without TIMI Major Bleeding events vs. time, stratified by dose.

Patients treated with ticagrelor 60 mg bid and ticagrelor 90 mg bid in the PEGASUS trial exhibited a higher incidence of TIMI major bleeding compared to placebo patients, consistent with the safety profile of other commercially available P2Y$_{12}$ receptor antagonists. The risk of event was described to increase with increasing drug exposure (ticagrelor $c_{ss,av}$) by a log-linear exposure-response relationship. The estimated relative risk increase versus placebo after 36 months was 142% and 160% for ticagrelor 60 and 90 mg bid, respectively, and the increased risk of TIMI major bleeding with ticagrelor exposure was similar and consistent across subgroups. FIG. 18 shows Kaplan-Meier estimates of patients without TIMI Major Bleeding events vs. time, stratified by dose. No subgroup was statistically identified to be more or less sensitive to ticagrelor exposure after accounting for risk factors.

Age was the only risk factor that was identified in both the final CV death/myocardial infarction/stroke model as well as in the final TIMI major bleeding model. However, the average risk of CV death, myocardial infarction, or stroke was reduced for patients in the ticagrelor 60 mg bid and ticagrelor 90 mg bid arms relative to the placebo arm for all compared age groups (Table 18). The absolute risk reduction for the composite endpoint of cardiovascular death, myocardial infarction, and stroke at three years with ticagrelor 60 mg bid compared to placebo was higher in patients greater than 75 years of age than in patients less than 65 years of age (2.15% vs 1.38%). However, the absolute risk increase for TIMI major bleeding at three years with ticagrelor (60 mg) compared to placebo was also higher in patients greater than 75 years of age than in patients less than 65 years of age (2.38% vs 1.05%).

TABLE 18

Predicted (observed) average risk at 3 years versus age group for cardiovascular death, myocardial infarction, and stroke events and TIMI major bleeding events

| Treatment Group | Age <65 years | | Age 65-75 years | | Age >75 years | |
|---|---|---|---|---|---|---|
| | CV Event* | Bleed** | CV Event* | Bleed** | CV Event* | Bleed** |
| Placebo | 7.30% | 0.75% | 8.68% | 1.13% | 12.06% | 1.62% |
| | (8.5%) | (0.82%) | (7.83%) | (1.04%) | (14.1%) | (1.7%) |
| Ticagrelor 60 mg bid | 5.92% | 1.80% | 6.93% | 2.75% | 9.91% | 4.00% |
| | (6.31%) | (1.52%) | (7.06%) | (2.88%) | (9.37%) | (4.25%) |
| Ticagrelor 90 mg bid | 5.80% | 1.93% | 6.98% | 2.94% | 9.31% | 4.24% |
| | (5.77%) | (2.29%) | (6.8%) | (2.46%) | (13.2%) | (5.76%) |

*CV Event: CV death, MI, or stroke
**Bleed: TIMI major bleeding

Figure 19:
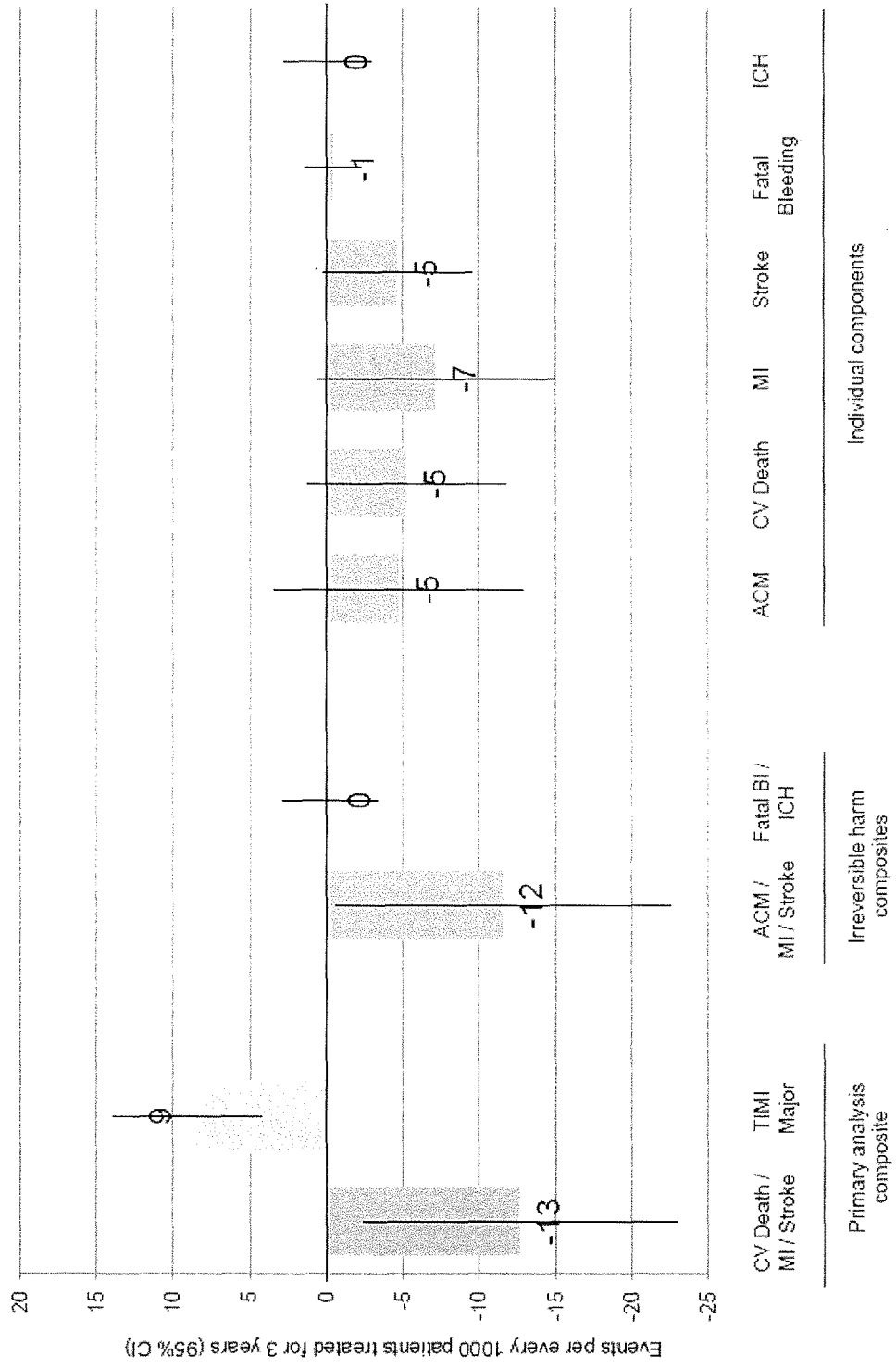
FIG. 19 depicts the events caused or prevented per every 1000 patients treated for 3 years in the PEGASUS-TIMI 54 trial in the ticagrelor 60 mg bid arm for various safety and efficacy endpoints.
Figure 20:
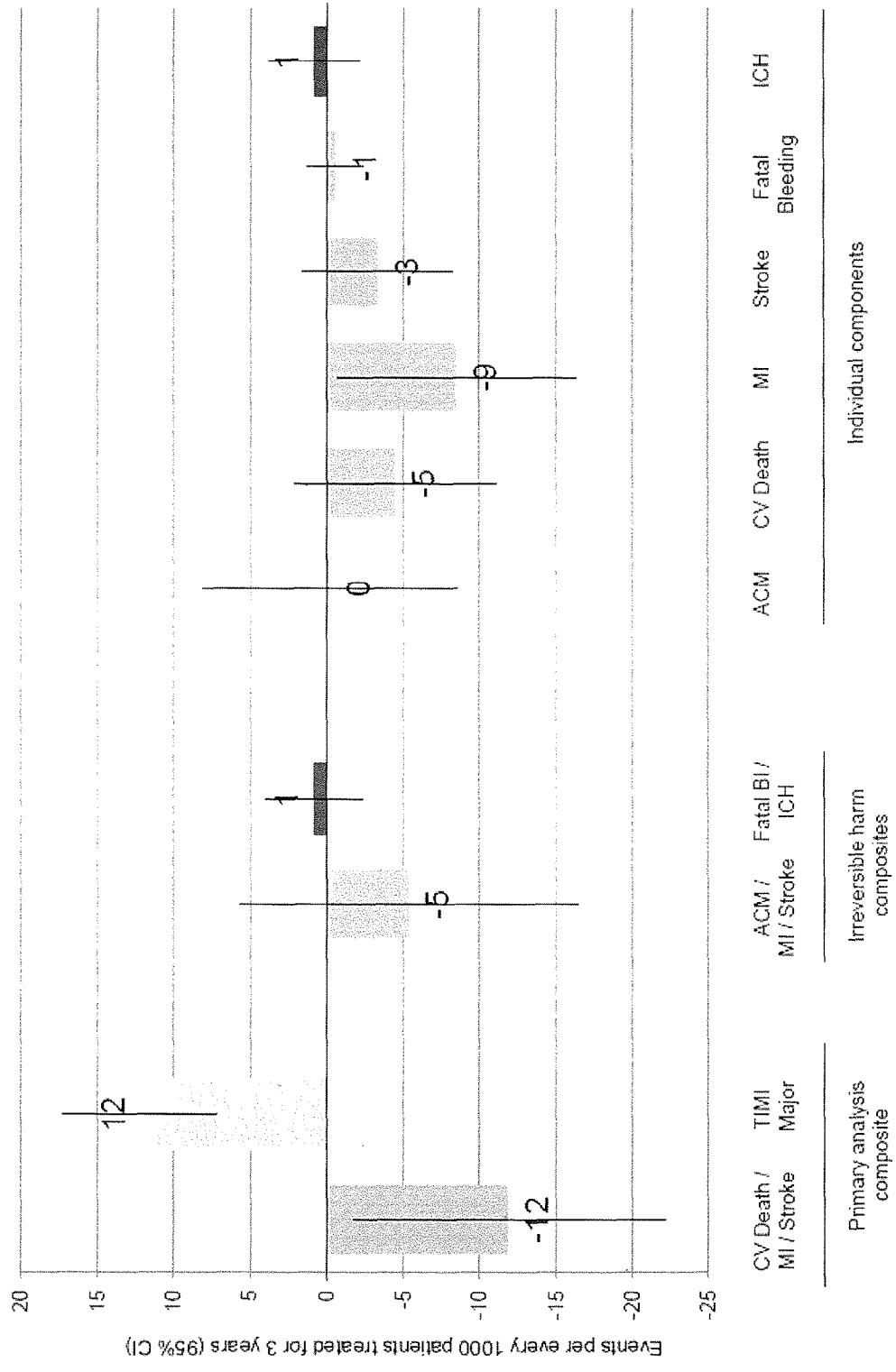
FIG. 20 depicts the events caused or prevented per every 1000 patients treated for 3 years in the PEGASUS-TIMI 54 trial in the ticagrelor 90 mg bid arm for various safety and efficacy endpoints.

Patients administered ticagrelor 60 mg bid experienced a net clinical benefit (time from randomization to first occurrence of any event from the composite of cardiovascular death, myocardial infarction, stroke, or TIMI major bleeding) in the PEGASUS-TIMI 54 trial, with a relative risk reduction of 5% relative to the placebo arm (Table 19). In addition, risk reduction for irreversible harm (time from randomization to first occurrence of any event from the composite of cardiovascular death, myocardial infarction (MI), stroke, intracranial hemorrhage (ICH), or fatal bleeding) was demonstrated for patients administered ticagrelor 60 mg bid and patients administered 90 mg bid compared to the placebo arm. A relative risk reduction for irreversible harm of 12% and 14% was demonstrated for ticagrelor 90 mg bid and ticagrelor 60 mg bid relative to the placebo arm in the PEGASUS trial. FIGS. 19 and 20 depict the events per every 1000 patients treated for 3 years in the PEGASUS trial in the ticagrelor 60 mg bid and ticagrelor 90 mg bid arms, respectively.

TABLE 19

Net Clinical Benefit and Irreversible Harm

| Characteristic | Ticagrelor 90 mg bid vs. placebo (N = 6988) | | | Ticagrelor 60 mg bid vs. placebo (N = 6958) | | |
|---|---|---|---|---|---|---|
| | RRR (%) | HR (95% CI) | P-value | RRR (%) | HR (95% CI) | P-value |
| Net clinical benefit* | 0 | 1.00 (0.90-1.22) | 0.9563 | 5 | 0.95 (0.85-1.06) | 0.3412 |
| Irreversible harm** | 12 | 0.88 (0.78-0.99) | 0.0372 | 14 | 0.86 (0.77-0.97) | 0.0160 |

*Net clinical benefit is a composite endpoint of CV death, MI, stroke, or TIMI major bleeding
**Irreversible harm is a composite endpoint of CV death, MI, stroke, ICH, or fatal bleeding Irreversible harm analysis focused on events with the most severe consequences and excluded "other TIMI major bleeding events." As used herein, "other TIMI major bleeding events" refers to TIMI major bleeding events other than intracranial hemorrhage or fatal bleeding. While "other TIMI major bleeding events" are clinically important because they cause morbidity and requirement for care, the events are still manageable clinically and do not cause irreversible harm. Excluding "other TIMI major bleeding events" from the benefit-risk evaluation is consistent with the approach previously used by the Food and Drug Administration for other drugs. Based on intention-to-treat data (i.e., regardless of study drug discontinuation), if 10,000 patients were started on treatment with ticagrelor versus placebo, 41 and 31 TIMI major bleeding events per year would be prevented with ticagrelor 90 mg bid and ticagrelor 60 mg bid, respectively.

An absolute risk reduction was observed for ticagrelor 90 mg bid and ticagrelor 60 mg bid relative to placebo for: the primary composite endpoint of CV death, MI, or stroke; and the individual endpoints CV death, MI, and stroke (Table 20). Accordingly, when the benefits are weighed against the risks for events of irreversible harm, a favorable benefit-risk balance is demonstrated for both ticagrelor 90 mg bid and ticagrelor 60 mg bid compared to placebo.

TABLE 20

Absolute Risk Reduction (ARR), Absolute Risk Increase (ARI) and Number Needed to Treat (NNT) or Harm (NNH)

| | Ticagrelor 90 mg bid | | Ticagrelor 60 mg bid | |
|---|---|---|---|---|
| Efficacy endpoint | ARR (%) | NNT | ARR (%) | NNT |
| CV death, MI, or stroke | 1.19 | 84 | 1.27 | 79 |
| CV death | 0.45 | 222 | 0.53 | 189 |
| MI | 0.85 | 118 | 0.72 | 139 |
| Stroke | 0.33 | 303 | 0.47 | 213 |
| Safety endpoint | ARI (%) | NNH | ARI (%) | NNH |
| TIMI major bleeding | 1.54 | 65 | 1.24 | 81 |
| ICH | 0.09 | 1111 | 0.14 | 714 |
| Fatal bleeding | −0.15 | n/a | −0.01 | n/a |

There has been much uncertainty regarding the duration of dual antiplatelet therapy required in patients with coronary disease. For patients with a history of spontaneous myocardial infarction, observations from other studies have suggested a benefit to a longer duration of more intensive antiplatelet therapy. For example, in landmark analyses from trials of the three principal $P2Y_{12}$ receptor antagonists (clopidogrel, prasugrel, and ticagrelor) in patients presenting with acute coronary syndromes, there appeared to be continued accrual of clinical benefit with $P2Y_{12}$ receptor blockade in the months beyond the immediate period following the acute coronary syndrome.

Similarly, in the subgroup of patients with prior myocardial infarction from a trial of a protease-activated platelet receptor antagonist, there appeared to be continued accrual of clinical benefit beyond the first year of therapy. Of note, though, a dedicated trial of long-term prevention with clopidogrel on a background of aspirin in a broad patient population with atherosclerotic disease or risk factors did not show a statistically significant benefit. A subsequent analysis specifically examining the subset of patients with prior myocardial infarction did suggest a reduction in ischemic risk, but this was post hoc and current practice guidelines continue to recommend stopping $P2Y_{12}$ receptor antagonists 1 year after a myocardial infarction.

Further contributing to uncertainty about the effectiveness of prolonged dual antiplatelet therapy, a series of randomized trials have not shown a benefit to prolonged dual antiplatelet therapy following percutaneous coronary intervention (PCI) (including after ACS). However, these studies were relatively small and enrolled relatively low risk patients.

Figure 21:
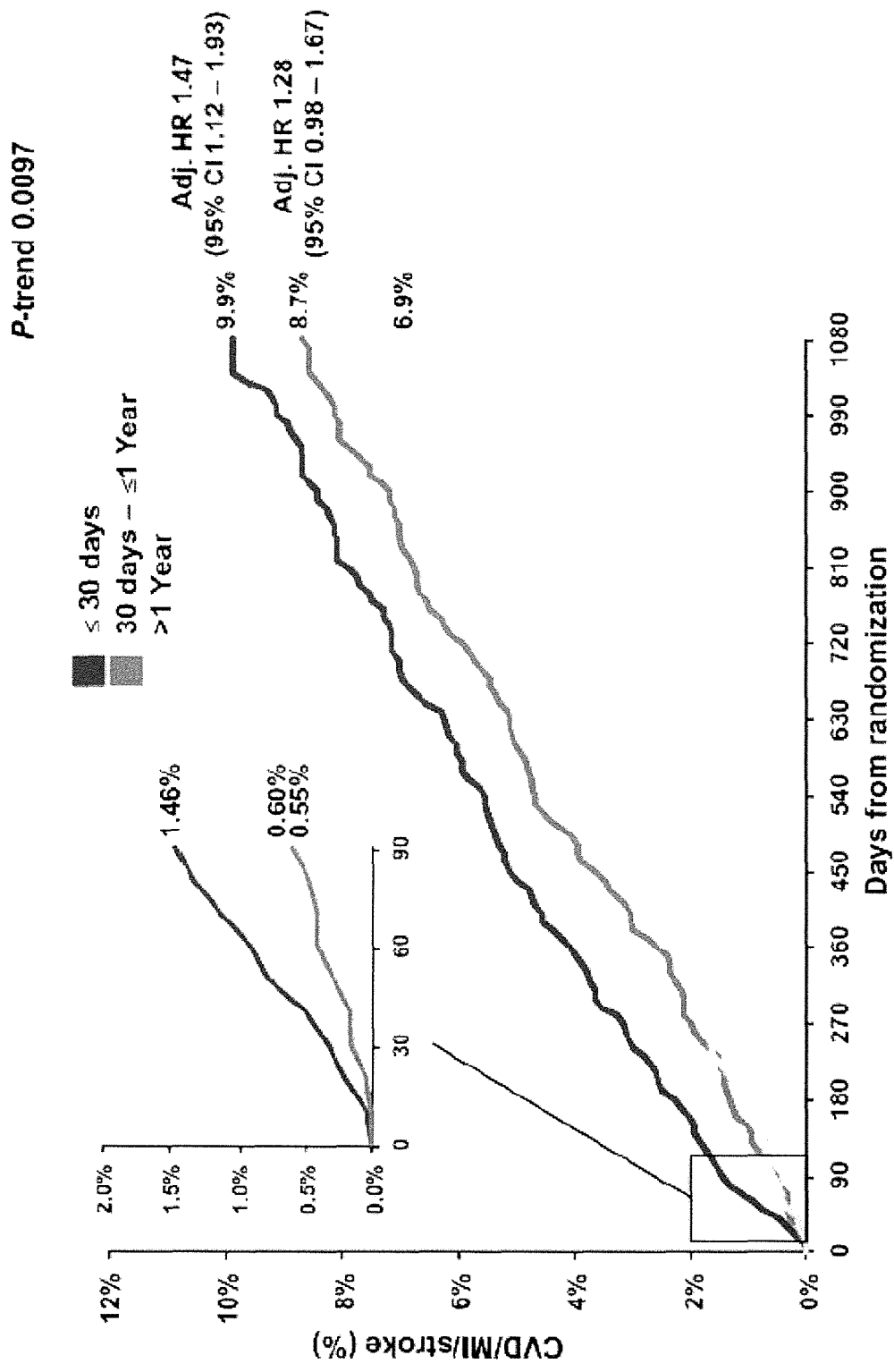
FIG. 21 depicts the Kaplan-Meier rates for the composite endpoint of cardiovascular death, myocardial infarction, or stroke in patients randomized to placebo at 90 days and 3 years by time from $P2Y_{12}$ inhibitor withdrawal.
Figure 22:
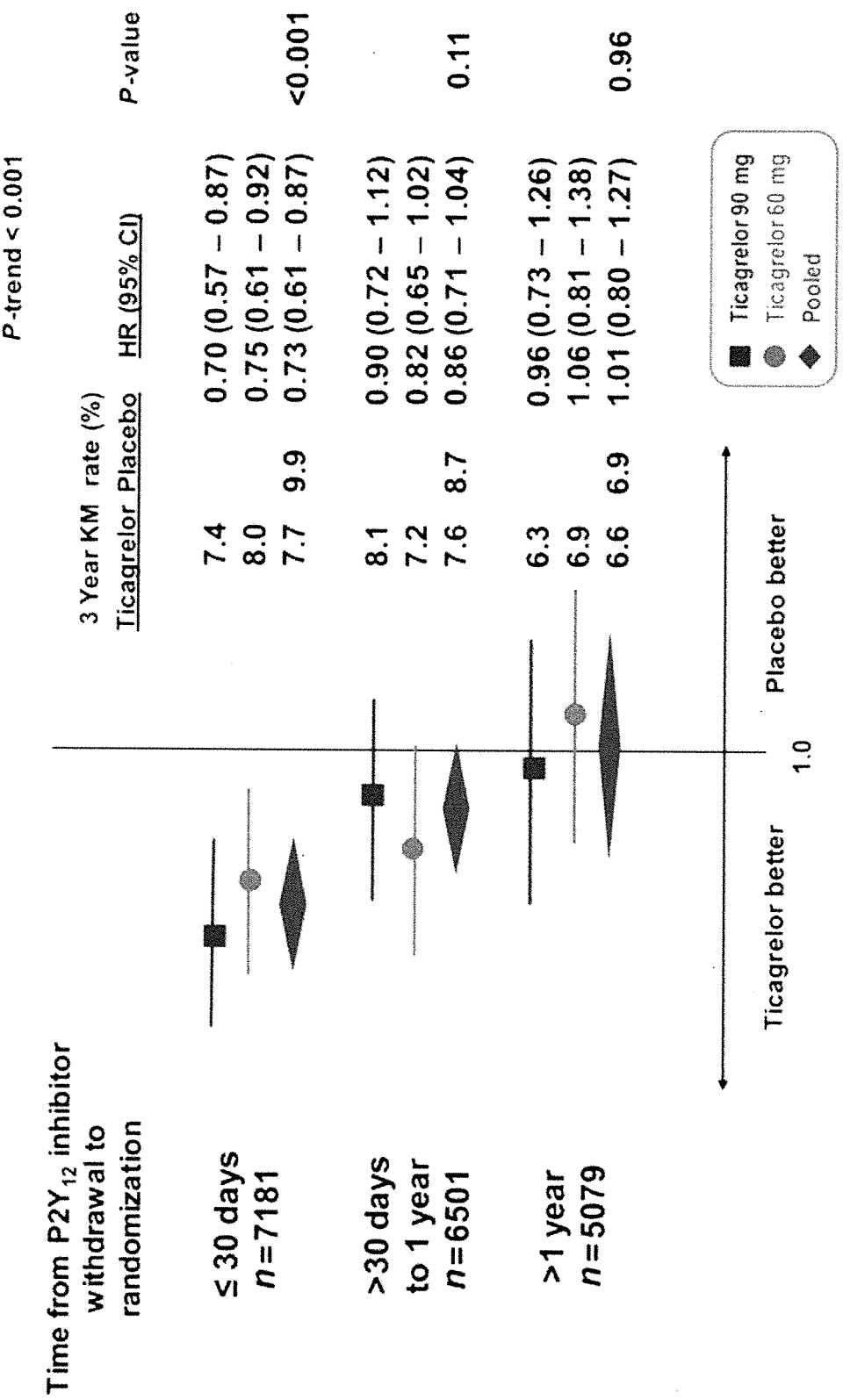
FIG. 22 depicts hazard ratios for cardiovascular death, myocardial infarction, or stroke at 3 years by time from $P2Y_{12}$ inhibitor withdrawal to randomization in the PEGASUS-TIMI 54 Study.
Figure 23:
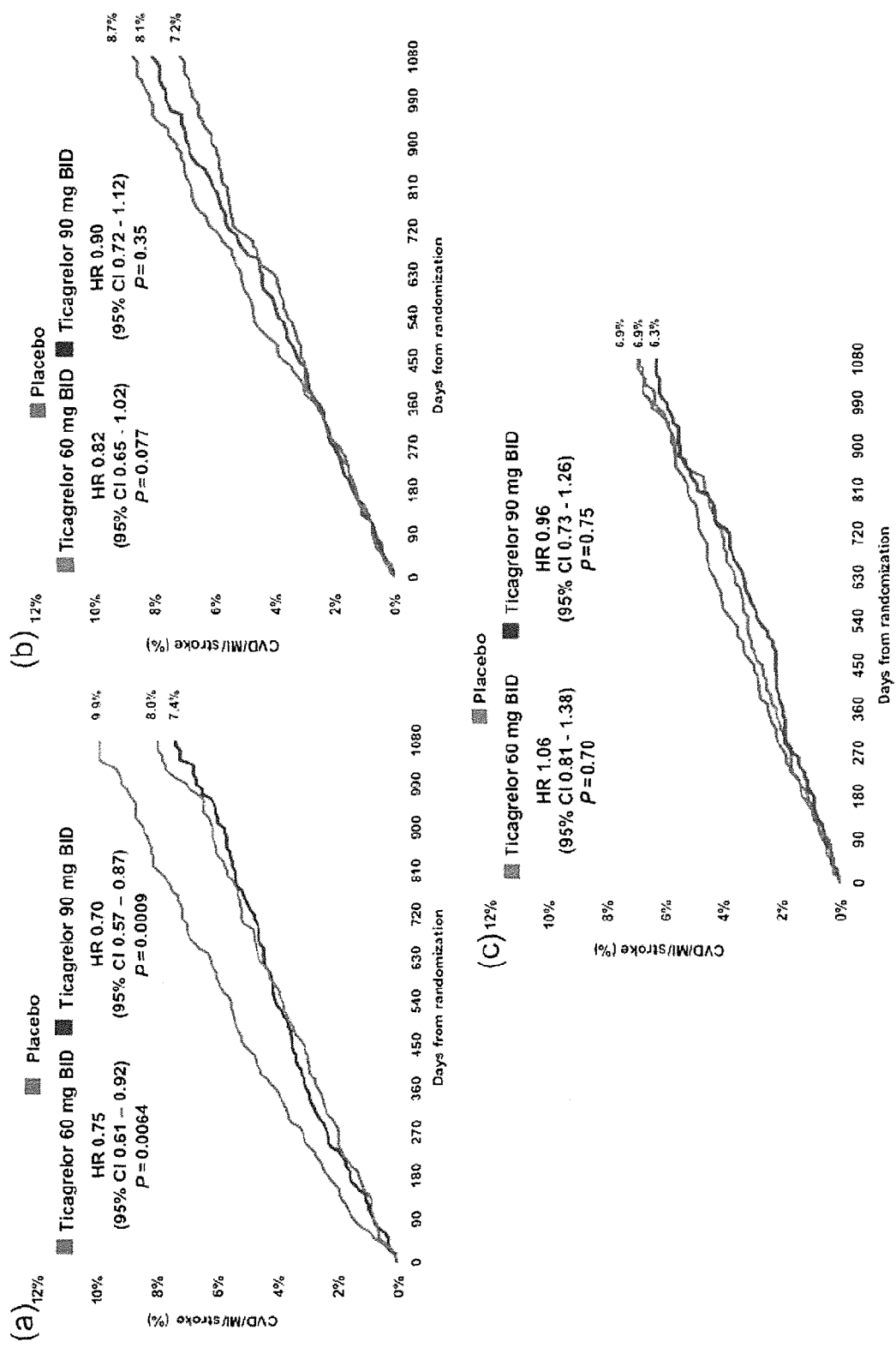
FIG. 23 depicts the Kaplan-Meier rates for cardiovascular death, myocardial infarction, or stroke at 3 years with ticagrelor 90 mg bid twice daily, ticagrelor 60 mg bid twice daily compared with placebo in patients withdrawn from $P2Y_{12}$ inhibitor therapy within 30 days (A), between 30 days and 1 year (B), and more than 1 year of randomization (C).
Figure 24:
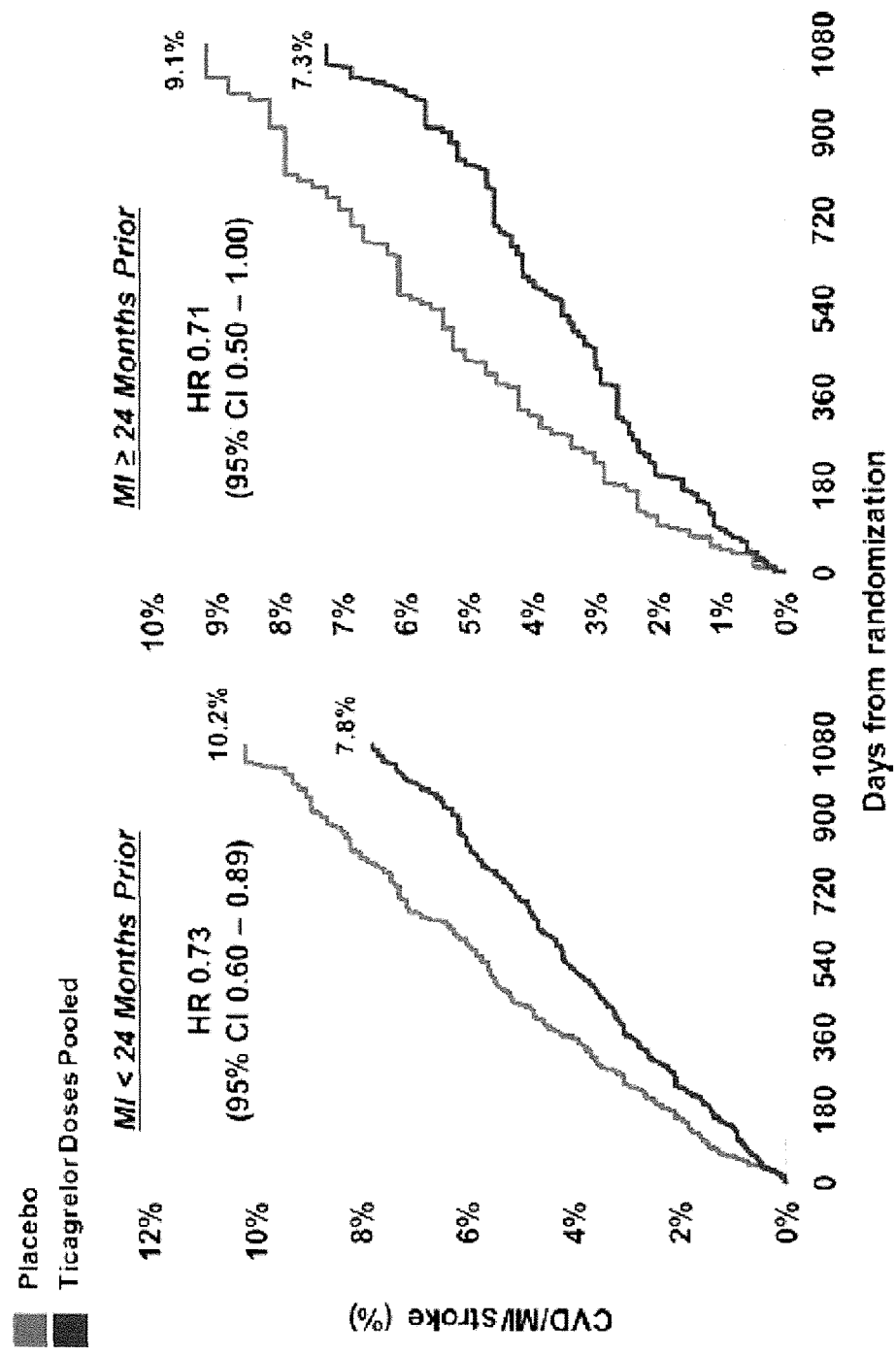
FIG. 24 depicts the Kaplan-Meier rates for the composite endpoint of cardiovascular death, myocardial infarction, or stroke at 3 years with ticagrelor doses pooled (purple) compared with placebo in patients withdrawn from P2Y12 inhibitor therapy within 30 days of randomization stratified by a qualifying myocardial infarction, 24 months prior to randomization (left) and ≥24 months prior to randomization (right).

Patients in PEGASUS-TIMI 54 were further categorized by time from last $P2Y_{12}$ inhibitor (days: ≤30 days, 31-360, >360). In the placebo arm, patients who more recently stopped $P2Y_{12}$ inhibitor therapy had a greater number of risk factors but still had a higher risk of MACE after multivariable adjustment [≤30 days, hazard ratio $(HR)_{adj}$ 1.47, 95% confidence interval (CI) 1.12-1.93, P=0.005; 30 days—1 year, $HR_{adj}$ 1.28, 95% CI 0.98-1.67, P=0.073) compared with those who stopped >1 year prior (P-trend=0.0097) (FIG. 21). The benefit of ticagrelor depended on the time from last dose, with HRs (95% CI) for ticagrelor (pooled doses) vs. placebo of 0.73 (0.61-0.87), 0.86 (0.71-1.04), and 1.01 (0.80-1.27), respectively, by category (P-trend for interaction <0.001) (FIG. 22). FIG. 23 shows the Kaplan-Meier curve for cardiovascular death, myocardial infarction, or stroke at 3 years with ticagrelor 90 mg bid twice daily, ticagrelor 60 mg bid twice daily compared with placebo in patients withdrawn from P2Y12 inhibitor therapy within 30 days, between 30 days and 1 year, and more than 1 year of randomization. The benefit in those ≤30 days of stopping was similar regardless of time from MI (<2 years, HR 0.73, 95% CI 0.60-0.89 vs. ≥2 years, HR 0.71, 95% CI 0.50-1.00) (FIG. 24).

TABLE 21

Efficacy of ticagrelor (doses pooled) vs. placebo for reduction of CVD, MI, or Stroke by time from $P2Y_{12}$ inhibitor withdrawal - restricted to N = 17,885 patients with no history of MI or PCI within one year of randomization.

| | Hazard Ratio | p-value | p-trend across groups |
|---|---|---|---|
| 0-30 day | 0.73 (95% CI 0.60-0.87) | 0.0005 | 0.0009 |
| >30 to 1 year | 0.84 (95% CI 0.70-1.02) | 0.0853 | |
| >1 year | 1.01 (95% CI 0.80-1.28) | 0.9249 | |

Patients enrolled in the PEGASUS study who began or recommenced treatment with ticagrelor (60 mg and 90 mg pooled) within 30 days following withdrawal of dual antiplatelet therapy experienced a 27% reduction in the risk of developing a subsequent atherothrombotic event (2.2% absolute reduction). Patients enrolled in the PEGASUS study who began or recommenced treatment with ticagrelor (60 mg and 90 mg pooled) between 31 days and one year following withdrawal of dual antiplatelet therapy experienced a 14% reduction in the risk of developing a subsequent atherothrombotic event (1.1% absolute reduction). Patients who began or recommenced treatment with ticagrelor more than one year after withdrawal of previous dual antiplatelet therapy event did not experience a reduction in the risk of developing a subsequent atherothrombotic event. Accordingly, the reduction in the risk of cardiovascular death, myocardial infarction, or stroke in stable patients with prior myocardial infarction is greatest in those who have more recently stopped $P2Y_{12}$ therapy, with hazard ratios of 0.75, 0.82, and 1.06 respectively for patients in the 60 mg ticagrelor bid arm.

Figure 25:
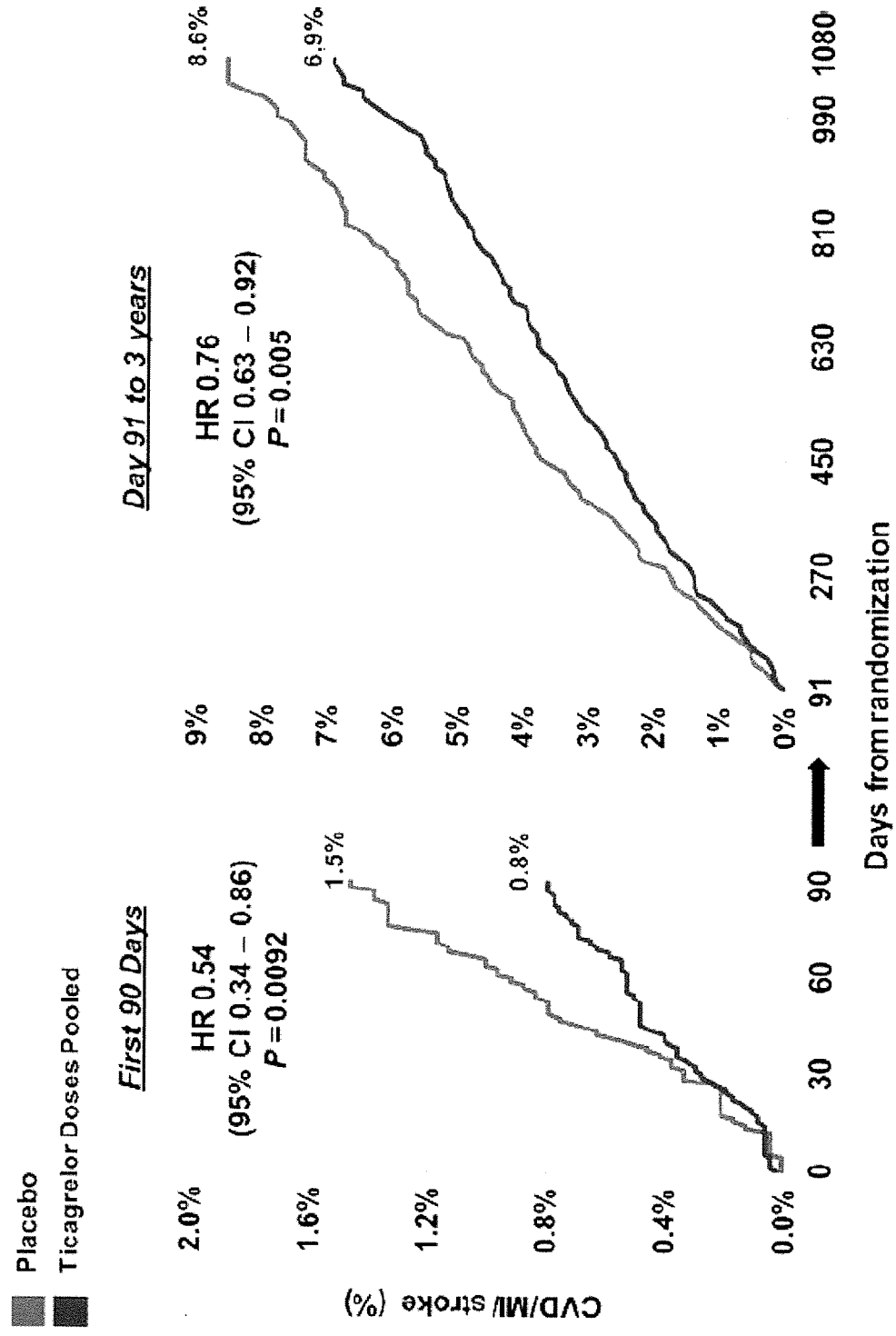
FIG. 25 depicts the Kaplan-Meier rates for the composite endpoint of cardiovascular death, myocardial infarction, or stroke for the first 90 days (left) and as a landmark from 90 days to 3 years (right) in patients withdrawn from $P2Y_{12}$ inhibition ≤30 days from randomization by treatment (placebo vs. ticagrelor doses pooled).
Figure 26:
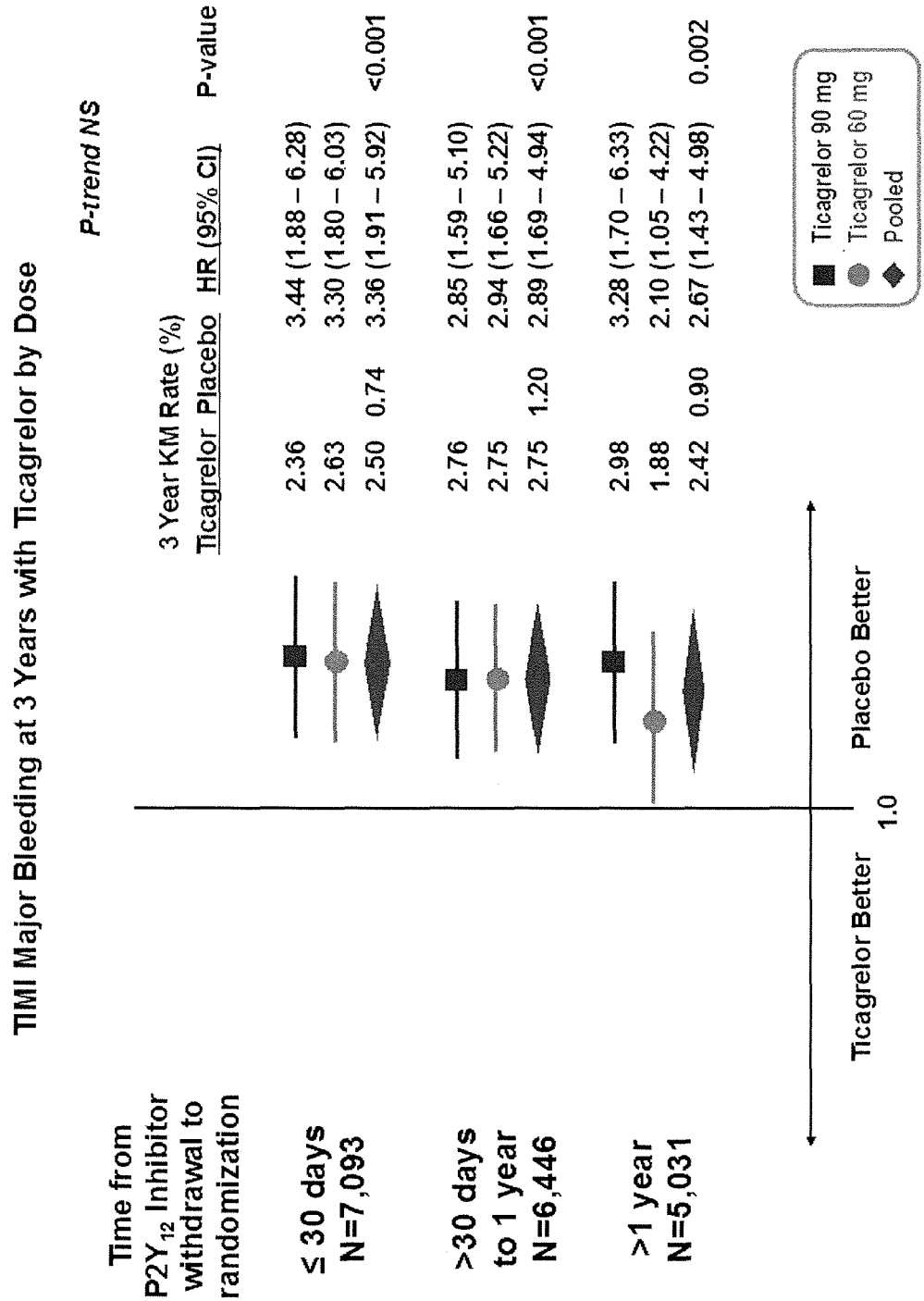
FIG. 26 depicts TIMI major bleeding at 3 years with ticagrelor 90 mg bid twice daily (red), ticagrelor 60 mg bid twice daily (blue), and both doses pooled (purple) compared to placebo by time from $P2Y_{12}$ inhibitor withdrawal.
Figure 27:
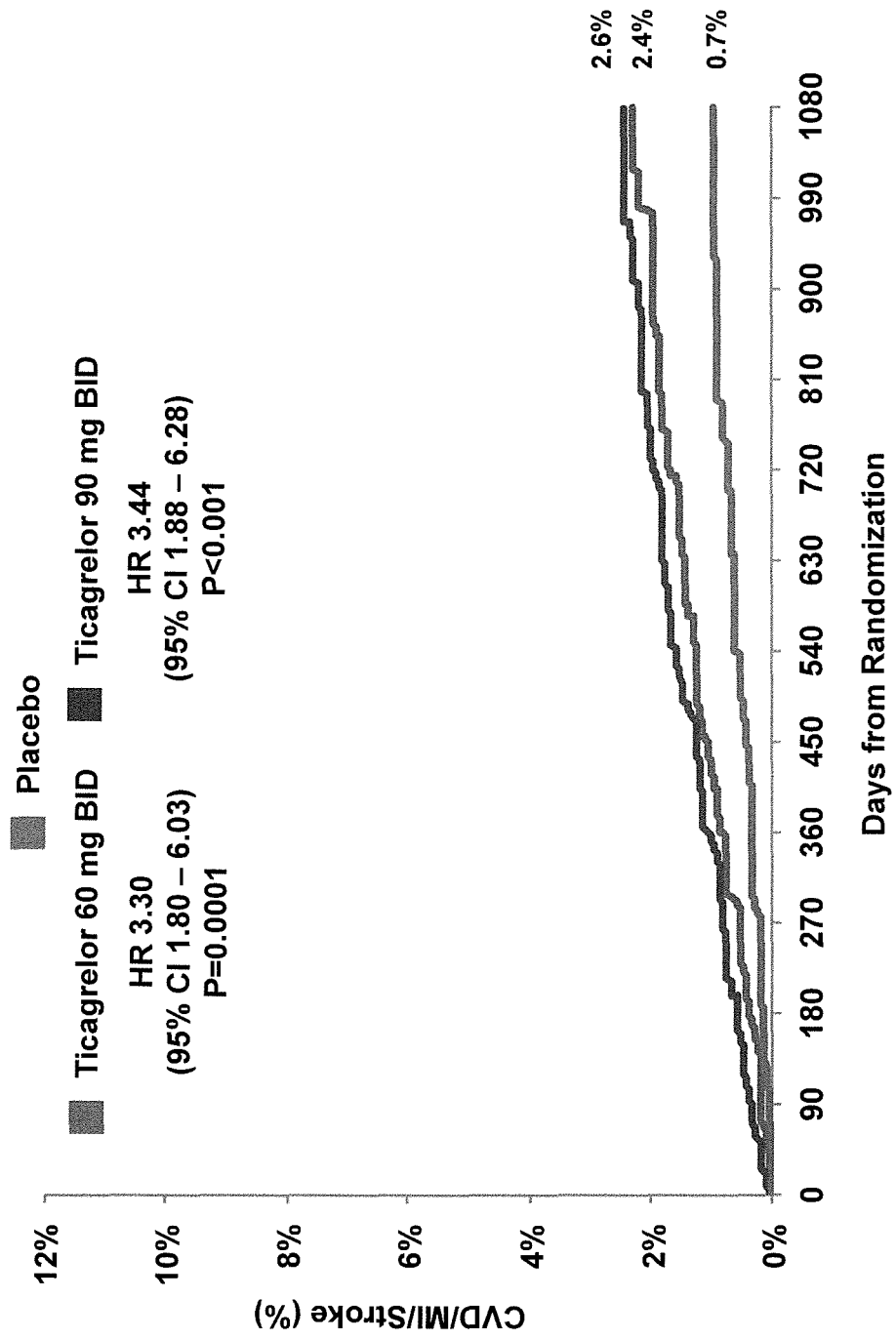
FIG. 27 depicts TIMI major bleeding at 3 years with ticagrelor 90 mg bid twice daily (red), ticagrelor 60 mg bid twice daily (blue) compared to placebo (green) in patients withdrawn from $P2Y_{12}$ inhibitor therapy within 30 days.

In the subgroup of patients who began or recommenced treatment with ticagrelor (60 mg and 90 mg pooled) within 30 days following withdrawal of dual antiplatelet therapy, the reduction in the risk of cardiovascular death, myocardial infarction, or stroke was similar regardless of whether the patient's qualifying myocardial infarction was less than 2 years prior to randomization (HR 0.73, 95% CI 0.60-0.89) or 2 years or more (HR 0.71, 95% CI 0.50-1.00). The benefit of ticagrelor (doses pooled) was notable both in the first 90 days after randomization, with an HR of 0.54 (95% CI 0.34-0.86), and also beyond 90 days (HR 0.76, 95% CI 0.63-0.92) for both doses pooled (FIG. 25). Similar effect sizes were seen for the individual components of the primary endpoint, with HRs for pooled ticagrelor doses vs. placebo for cardiovascular death of 0.78 (95% CI 0.57-1.07), for myocardial infarction of 0.72 (95% CI 0.58-0.90), and for stroke of 0.64 (95% CI 0.43-0.95).

Baseline characteristics for patients by timing from last dose of $P2Y_{12}$ inhibitor in the PEGASUS trial were similar between groups for most characteristics (Table 22). However, patients who had discontinued their $P2Y_{12}$ inhibitor within the past 30 days were, temporally closer to their most recent myocardial infarction (median 16 vs. 19 vs. 29 months, P<0.001). They also more frequently had diabetes, multivessel coronary artery disease (CAD), and prior PCI, and were more likely to be randomized in North America.

Of note, patients in the placebo arm who had discontinued their $P2Y_{12}$ inhibitor within the past 30 days were at higher risk for cardiovascular death, myocardial infarction, or stroke (9.91% at 3 years) when compared with those who had discontinued 30 days to 1 year prior (8.70%) and those who stopped more than 1 year before randomization (6.91%, P-trend 0.0097). On the other hand, TIMI major bleeding in patients randomized to placebo was similar across time bins from $P2Y_{12}$ inhibitor withdrawal with 3 year rates in those less than 30 days, 30 days to 1 year, and more than 1 year of 0.7, 1.2, and 0.9%, respectively. After adjusting for baseline differences, the hazard ratio for TIMI major bleeding was 0.51 (95% CI 0.20-1.33, P=0.17) for patients stopping less than 30 days and 0.69 (0.29-1.66, P=0.41) for those stopping 30 days to 1 year both compared with those stopping 0.1 year from randomization (P-trend across groups 0.18).

TABLE 22

Baseline characteristics, stratified by time from $P2Y_{12}$ inhibitor withdrawal

| Variable | ≤30 Days | | | >30 Days to 1 Year | | | >1 Year | | |
|---|---|---|---|---|---|---|---|---|---|
| | 90 mg | 60 mg | Placebo | 90 mg | 60 mg | Placebo | 90 mg | 60 mg | Placebo |
| N | 2397 | 2383 | 2401 | 2142 | 2178 | 2181 | 1706 | 1697 | 1676 |
| Demographics | | | | | | | | | |
| Age, median(IQR) | 65 | 65 | 65 | 65 | 65 | 65 | 66 | 66 | 66 |
| | (58, 71) | (57, 71) | (58, 71) | (59, 71) | (59, 71) | (60, 71) | (59, 71) | (59, 71) | (59, 71) |
| Female (%) | 22 | 21 | 22 | 22 | 23 | 25 | 25 | 23 | 21 |
| Caucasian* (%) | 82 | 82 | 82 | 91 | 90 | 90 | 90 | 92 | 92 |
| BMI, median (IQR) | 28 | 28 | 28 | 28 | 28 | 28 | 28 | 28 | 28 |
| | (25, 31) | (25, 31) | (25, 31) | (25, 31) | (25, 31) | (25, 31) | (25, 31) | (25, 31) | (26, 31) |
| Clinical Characteristics | | | | | | | | | |
| Hypertension (%) | 77 | 79 | 78 | 77 | 75 | 75 | 75 | 77 | 77 |
| Hyperlipidemia (%) | 81 | 80 | 81 | 77 | 75 | 76 | 76 | 78 | 79 |
| Current smoker (%) | 16 | 19 | 17 | 17 | 17 | 16 | 18 | 17 | 17 |
| Diabetes mellitus (%) | 33 | 34 | 33 | 29 | 31 | 30 | 31 | 31 | 31 |
| Multivessel CAD (%) | 67 | 69 | 68 | 61 | 60 | 59 | 57 | 57 | 59 |
| History of PCI (%) | 92 | 93 | 91 | 87 | 88 | 86 | 88 | 86 | 86 |
| History of >1 MI (%) | 15 | 16 | 17 | 16 | 16 | 16 | 16 | 16 | 17 |
| **eGFR <60 ml/min(%) | 22 | 22 | 23 | 23 | 21 | 22 | 24 | 22 | 24 |
| Region | | | | | | | | | |
| Western Europe (%) | 23 | 24 | 23 | 34 | 34 | 35 | 39 | 37 | 37 |
| Eastern Europe (%) | 25 | 25 | 25 | 31 | 31 | 30 | 28 | 30 | 31 |
| North America (%) | 29 | 27 | 28 | 16 | 16 | 16 | 14 | 13 | 13 |
| South America (%) | 6 | 7 | 7 | 12 | 12 | 13 | 12 | 14 | 11 |
| Asia/Pacific (%) | 17 | 17 | 17 | 8 | 8 | 7 | 8 | 7 | 7 |
| Qualifying Event | | | | | | | | | |
| Months from MI-M | 16 | 16 | 16 | 18 | 19 | 19 | 28 | 29 | 29 |
| (IQR) | (13, 24) | (13, 24) | (13, 24) | (15, 23) | (15, 23) | (15, 23) | (25, 32) | (25, 33) | (25, 33) |
| STEMI | 55 | 54 | 56 | 54 | 55 | 55 | 55 | 56 | 56 |
| NSTEMI | 41 | 42 | 41 | 43 | 42 | 41 | 42 | 40 | 40 |
| MI type unknown | 4 | 5 | 4 | 4 | 3 | 4 | 4 | 5 | 4 |

*Self Reported
**The estimated glomerular filtration rate was calculated with the use of the Modification of Diet in Renal Disease equation.

The benefit of ticagrelor for long-term secondary prevention in patients with prior MI and at least one additional risk factor appeared more marked in patients continuing on or re-starting after only a brief interruption of $P2Y_{12}$ inhibition, when compared with patients who had proved themselves stable more than 2 years from their MI and off $P2Y_{12}$ inhibitor therapy for more than a year. The increase in bleeding events with ticagrelor was similar regardless of this time interval. For clinicians considering a strategy of prolonged $P2Y_{12}$ inhibitor therapy in high-risk patients, these data suggest greater benefit in the continuation of such therapy without interruption after MI, rather than re-initiating such therapy in patients who have remained stable for an extended period. Table 23 shows outcomes at 36 months by time from $P2Y_{12}$ withdrawal to randomization.

TABLE 23

Outcomes at 3 years by time from P2Y$_{12}$ inhibitor withdrawal to randomization

| Timing from P2Y$_{12}$ inhibitor withdrawal | Endpoint | Placebo (n = 6258) n (%) | Ticagrelor pooled (n = 12 503) n (%) | Ticagrelor 90 mg bid (n = 6245) n (%) | Ticagrelor 60 mg bid (n = 6258) n (%) | HR (95% CI) P-value Ticagrelor pooled vs. placebo | Ticagrelor 90 mg bid vs. placebo | Ticagrelor 60 mg bid vs. placebo |
|---|---|---|---|---|---|---|---|---|
| ≤30 days | Efficacy | | | | | | | |
| | CV death, myocardial infarction, stroke | 213 (9.9) | 313 (7.7) | 152 (7.4) | 161 (8.0) | 0.73 (0.61-0.87) 0.0003 | 0.70 (0.57-0.87) 0.0009 | 0.75 (0.61-0.92) 0.0064 |
| | CV death | 64 (3) | 100 (2.5) | 53 (2.5) | 47 (2.4) | 0.78 (0.57-1.07) 0.13 | 0.83 (0.58-1.19) 0.31 | 0.74 (0.51-1.08) 0.12 |
| | Cor. heart dis. death | 36 (1.8) | 52 (1.3) | 24 (1.1) | 28 (1.5) | 0.72 (0.47-1.11) 0.14 | 0.67 (0.40-1.12) 0.12 | 0.78 (0.48-1.28) 0.33 |
| | Myocardial infarction | 134 (6.2) | 195 (4.9) | 90 (4.6) | 105 (5.2) | 0.72 (0.58-0.90) 0.0038 | 0.67 (0.51-0.87) (0.0028 | 0.78 (0.61-1.01) 0.061 |
| | Stroke | 44 (2.1) | 56 (1.4) | 28 (1.3) | 28 (1.5) | 0.64 (0.43-0.95) 0.025 | 0.64 (0.4-1.02) 0.061 | 0.64 (0.4-1.03) 0.064 |
| | Safety | | | | | | | |
| | TIMI Major Bleeding | 14 (0.7) | 86 (2.5) | 43 (2.4) | 43 (2.6) | 3.36 (1.91-5.92) <0.0001 | 3.44 (1.88-6.28) <0.001 | 3.3 (1.8-6.03) 0.0001 |
| | TIMI Major or Minor Bleeding | 21 (1.1) | 134 (4.0) | 67 (3.8) | 67 (4.1) | 3.50 (2.21-5.54) <0.0001 | 3.57 (2.19-.83) <0.0001 | 3.43 (2.1-5.60) <0.0001 |
| | Intracranial bleeding | 7 (0.4) | 23 (0.7) | 13 (0.7) | 10 (0.8) | 1.79 (0.77-4.18) 0.18 | 2.07 (0.82-5.18) 0.12 | 1.53 (0.58-4.03) 0.39 |
| | Fatal bleeding | 2 (0.1) | 8 (0.3) | 4 (0.2) | 4 (0.4) | 2.2 (0.47-13.34) 0.32 | 2.25 (0.41-12.28) 0.35 | 2.15 (0.4-11.76) 0.3 |
| | All-cause mortality | 106 (4.9) | 192 (4.7) | 108 (5.1) | 84 (4.3) | 0.91 (0.72-1.15) 0.43 | 1.02 (0.78-1.33) 0.90 | 0.80 (0.60-1.06) 0.12 |
| >30 days to ≤1 year | Efficacy | | | | | | | |
| | CV death, myocardial infarction, stroke | 171 (8.7) | 293 (7.6) | 152 (8.1) | 141 (7.2) | 0.86 (0.71-1.04) 0.11 | 0.90 (0.72-1.12) 0.35 | 0.82 (0.65-1.02) 0.08 |
| | CV death | 59 (3.1) | 90 (2.5) | 49 (2.8) | 41 (2.2) | 0.76 (0.55-1.06) 0.10 | 0.84 (0.57-1.22) 0.35 | 0.69 (0.46-1.02) 0.065 |
| | Cor. heart dis. death | 37 (1.8) | 52 (1.4) | 26 (1.4) | 26 (1.4) | 0.70 (0.46-1.07) 0.099 | 0.71 (0.43-1.17) 0.18 | 0.70 (0.42-1.15) 0.16 |
| | Myocardial infarction | 103 (5.2) | 174 (4.4) | 83 (4.2) | 91 (4.6) | 0.85 (0.66-1.08) 0.19 | 0.82 (0.61-1.09) 0.17 | 0.88 (0.66-1.16) 0.37 |
| | Stroke | 34 (1.9) | 62 (1.7) | 34 (1.9) | 28 (1.4) | 0.91 (0.6-1.39) 0.68 | 1.02 (0.63-1.64) 0.93) | 0.82 (0.49-1.35) 0.42 |
| | Safety | | | | | | | |
| | TIMI Major Bleeding | 16 (1.2) | 82 (2.7) | 39 (2.8) | 43 (2.7) | 2.89 (1.69-4.94) 0.0001 | 2.85 (1.59-5.1) 0.0004 | 2.94 (1.66-5.22) 0.0002 |
| | TIMI Major or Minor Bleeding | 21 (1.6) | 116 (3.8) | 57 (3.9) | 59 (3.8) | 3.11 (1.96-4.96) <0.0001 | 3.17 (1.92-5.23) <0.0001 | 3.07 (1.86-5.05) <0.0001 |
| | Intracranial bleeding | 5 (0.4) | 16 (0.5) | 7 (0.5) | 9 (0.6) | 1.81 (0.66-4.95) 0.25 | 1.63 (0.52-5.14) 0.40 | 1.97 (0.66-5.88) 0.22 |
| | Fatal bleeding | 5 (0.5) | 5 (0.2) | 1 (0.1) | 4 (0.3) | 0.57 (0.16-1.97) 0.37 | 0.24 (0.03-204) 0.19 | 0.87 (0.23-3.25) 0.84 |
| | All-cause mortality | 91 (4.9) | 161 (4.3) | 91 (4.8) | 70 (3.8) | 0.88 (0.68-1.14) 0.34 | 1.01 (0.75-1.35) 0.96 | 0.76 (0.56-1.04) 0.086 |

TABLE 23-continued

Outcomes at 3 years by time from P2Y$_{12}$ inhibitor withdrawal to randomization

| Timing from P2Y$_{12}$ inhibitor withdrawal | Endpoint | Placebo (n = 6258) n (%) | Ticagrelor pooled (n = 12 503) n (%) | Ticagrelor 90 mg bid (n = 6245) n (%) | Ticagrelor 60 mg bid (n = 6258) n (%) | HR (95% CI) P-value Ticagrelor pooled vs. placebo | HR (95% CI) P-value Ticagrelor 90 mg bid vs. placebo | HR (95% CI) P-value Ticagrelor 60 mg bid vs. placebo |
|---|---|---|---|---|---|---|---|---|
| >1 year | Efficacy | | | | | | | |
| | CV death, myocardial infarction, stroke | 103 (6.9) | 209 (6.6) | 100 (6.3) | 109 (6.9) | 1.01 (0.80-1.27) 0.96 | 0.96 (0.73-1.26) 0.75 | 1.05 (0.81-1.38) 0.70 |
| | CV death | 31 (2.2) | 81 (2.6) | 36 (2.3) | 45 (2.8) | 1.3 (0.86-1.97) 0.22 | 1.15 (0.71-1.86) 0.57 | 1.45 (0.92-2.29) 0.11 |
| | Cor. heart dis. death | 23 (1.6) | 40 (1.2) | 18 (1.1) | 22 (1.2) | 0.86 (0.52-1.44) 0.58 | 0.77 (0.42-1.43) 0.42 | 0.96 (0.53-1.71) 0.88 |
| | Myocardial infarction | 67 (4.4) | 121 (3.9) | 57 (3.6) | 64 (4.1) | 0.9 (0.66-1.21) 0.47 | 0.84 (0.59-1.19) 0.33 | 0.95 (0.68-1.34) 0.78 |
| | Stroke | 21 (1.4) | 44 (1.3) | 24 (1.5) | 20 (1.2) | 1.04 (0.62-1.75) 0.88 | 1.13 (0.63-2.03) 0.69 | 0.95 (0.51-1.75) 0.87 |
| | Safety | | | | | | | |
| | TIMI Major Bleeding | 12 (0.9) | 57 (2.4) | 34 (3) | 23 (1.9) | 2.67 (1.43-4.98) 0.0020 | 3.28 (1.7-6.33) 0.0004 | 2.1 (1.05-4.22) 0.037 |
| | TIMI Major or Minor Bleeding | 16 (1.2) | 84 (3.5) | 53 (4.4) | 31 (2.3) | 2.94 (1.72-5.02) <0.0001 | 3.82 (2.18-6.68) <0.0001) | 2.11 (1.16-3.87) 0.015 |
| | Intracranial bleeding | 5 (0.4) | 13 (0.6) | 6 (0.5) | 7 (0.6) | 1.48 (0.53-4.14) 0.46 | 1.42 (0.43-4.64) 0.57 | 1.56 (0.49-4.9) 0.45 |
| | Fatal bleeding | 1 (0) | 1 (0) | 0 (0) | 1 (0.1) | 0.57 (0.04-9.11) 0.69 | na | 1.11 (0.07-17.7) 0.94 |
| | All-cause mortality | 55 (3.8) | 147 (4.6) | 73 (4.7) | 74 (4.6) | 1.32 (0.97-1.80) 0.076 | 1.31 (0.92-1.86) 0.13 | 1.34 (0.94-1.9) 0.10 |

The results of PEGASUS-TIMI 54 now provide a prospectively defined evidence base affirming the hypothesis that long-term, more intensive platelet inhibition with ticagrelor reduces ischemic events in patients with prior spontaneous myocardial infarction.

Addressing a related but distinct question, the recently reported DAPT trial demonstrated a reduction in non-fatal ischemic events with continuation of dual antiplatelet therapy with a P2Y$_{12}$ receptor blocker on a background of aspirin for more than 12 months after coronary stenting. Of note, patients in DAPT were restricted to those without a bleeding complication in the prior 12 months and they were randomized immediately after the end of this period to continuation or withdrawal of therapy. Therefore, the trial selected a subset of patients who had recently tolerated P2Y$_{12}$ receptor blockade, which would tend to minimize their bleeding complications. Moreover, an increase in major adverse cardiovascular events was observed soon after discontinuation of P2Y$_{12}$ receptor blockade. (See Mauri L, Kereiakes D J, Yeh R W, et al. Twelve or 30 months of dual antiplatelet therapy after drug-eluting stents. *N Engl J Med* 2014; 371:2155-66.) This observation suggests that the clinical benefit observed in the PEGASUS trial, in which patients were further removed from their index event and from dual antiplatelet therapy, may underestimate the benefit that would be achieved in continuing ticagrelor without interruption in patients who had successfully completed a one-year course after their myocardial infarction.

Ticagrelor, like other antiplatelet agents, can cause significant, sometimes fatal bleeding. Ticagrelor at both doses increased bleeding including TIMI major bleeding, bleeding leading to transfusion and bleeding leading to study drug discontinuation. However, rates of the most severe bleeding events of intracranial hemorrhage and fatal bleeding were low over the three years of follow up and similar between the ticagrelor and placebo arms. Bleeding with ticagrelor did not differ in any of the major subgroups evaluated. However, it is important to note that the study protocol excluded patients with a recent bleed, prior stroke, or the need for oral anticoagulant therapy, and therefore the safety of long-term ticagrelor observed should not be generalized to other populations at higher risk of bleeding. Both doses of ticagrelor also caused dyspnea which occurred early after treatment initiation and contributed to higher rates of treatment discontinuation compared to placebo. The rates of drug discontinuation because of dyspnea seen with ticagrelor in this trial were higher than those seen in PLATO. However, that trial enrolled patients with acute coronary syndromes in whom transient dyspnea is frequently associated with their acute illness, in contrast to the stable patients in whom the onset of dyspnea may be surprising and hence more likely to lead to discontinuation.

Dyspnea would likely not manifest in patients already tolerating ticagrelor in whom one decides to continue treatment beyond one year after their myocardial infarction. Moreover, rates of drug discontinuation in PEGASUS were similar to those observed in other long-term secondary prevention studies, and most of the difference in discontinuation rates between the ticagrelor and placebo arms accumulated soon after randomization. Consequently, in clinical practice, if a patient was tolerating ticagrelor for 12 months after their myocardial infarction, continuing ticagrelor beyond 12 months would not be expected to trigger a new episode of dyspnea or further increase the risk of bleeding events.

The two doses of ticagrelor that were studied achieved a similar magnitude of efficacy in the intention-to-treat analysis. However, the rates of bleeding and dyspnea were numerically lower with ticagrelor 60 mg twice daily compared to ticagrelor 90 mg twice daily, resulting in a lower rate of treatment discontinuation and better tolerability for the 60 mg dose. Thus, in general, the 60 mg dose may offer a more attractive benefit-risk and tolerability profile. It should also be noted that both doses were studied on a background of low-dose aspirin, which is recommended for patients with stable ischemic heart disease.

The addition of ticagrelor 90 mg twice daily or 60 mg twice daily to low-dose aspirin reduced the risk of cardiovascular death, myocardial infarction, or stroke in patients with a myocardial infarction 1 to 3 years earlier. Ticagrelor increased TIMI major bleeding but did not significantly increase intracranial hemorrhage. Ticagrelor showed at least a trend of reducing fatal bleeding. Coupled with the established benefit of ticagrelor in the setting of an acute coronary syndrome, and taking into account the benefit-risk profile, these data support consideration of continuing ticagrelor beyond 1 year in patients with myocardial infarction who are at high risk of cardiovascular events and without major risk factors for bleeding. Taken together, the PLATO and PEGASUS-TIMI 54 clinical trials provide consistent evidence of the benefit ticagrelor can bring to patients with coronary artery disease in acute and chronic secondary prevention.

Example 2: Ticagrelor 60 mg Twice-Daily Provides Effective Platelet Inhibition in Patients with Prior Myocardial Infarction (MI)—the PEGASUS-TIMI 54 Platelet Function Substudy The PEGASUS-TIMI 54 trial studied 2 doses of ticagrelor, 90 mg orally twice daily (bid) and 60 mg bid, for long term prevention of ischaemic events in patients with prior MI. As shown in Example 1, compared to placebo, both doses reduced the risk of cardiovascular death, myocardial infarction, or stroke in patients who had a myocardial infarction 12 to 36 months earlier. The pharmacokinetics (PK) and pharmacodynamics of the 60 mg bid dose had not previously been studied. This substudy was aimed to characterize PK and platelet inhibition with ticagrelor 60 mg bid vs 90 mg bid. 180 patients who had received >4 weeks of study medication had blood sampling in the morning pre-maintenance dose and again 2 h post-dose. All patients were receiving aspirin. Plasma levels of ticagrelor and an active metabolite (AR-C124910XX) were determined. Well-known VerifyNow® P2Y12 assay and light transmittance aggregometry (LTA; ADP 20 uM) were performed. Groups were compared using Kruskal-Wallis test with significance attached to $P<0.01$ to allow for multiple group comparisons. Demographic characteristics at the time of randomization were generally well-matched between the groups (Table 23).

TABLE 23

Demographic Characteristics

|  | Placebo (N = 64) | Ticagrelor 60 mg bid (N = 58) | Ticagrelor 90 mg bid (N = 58) | All groups (N = 180) |
|---|---|---|---|---|
| Age mean (SD), years | 64.2 (6.6) | 63.3 (6.6) | 64.2 (6.9) | 63.9 (6.7) |
| Body weight, kg, median (IQR) | 86 (74.9-98) | 86 (76-99.8) | 81 (71-94) | 85 (74-98.5) |
| Female sex (%) | 21.9% | 8.6% | 17.2% | 16.1% |

Ticagrelor demonstrates dose proportional pharmacokinetics, which were similar in patients and healthy volunteers. The results showed that plasma ticagrelor levels were approximately ⅓ lower with 60 mg vs 90 mg (post dose: 448 vs 717 ng/mL; $P<0.001$). Both doses achieved high levels of platelet inhibition pre and post dose, with slightly more variability with 60 mg (Table 24). High platelet reactivity assessed by VerifyNow® (PRU >208) was rare with 60 mg pre-dose (3.5%) and absent post dose. Platelet reactivity pre- and post-dose as measured by LTA was numerically but not significantly lower with 90 mg than 60 mg. In addition, ticagrelor did not significantly affect measures of aspirin response: there were no differences in a VerifyNow Aspirin assay results between the placebo group and either ticagrelor group and no differences in serum thromboxane B2 levels.

Ticagrelor 60 mg bid achieved high levels of peak and trough platelet inhibition in nearly all patients, with similar consistency of effect compared to 90 mg bid. These results help to explain the efficacy of the lower ticagrelor dose in the PEGASUS-TIMI 54 study.

TABLE 24

Platelet Reactivity

|  | Placebo N = 64 | Ticagrelor 60 mg N = 58 | p value 60 mg vs placebo | Ticagrelor 90 mg N = 58 | p value 90 mg vs placebo | p value 90 mg vs 60 mg |
|---|---|---|---|---|---|---|
| VerifyNow ® PRU Pre dose | 265 (41) | 59 (63) | <0.001 | 47 (43) | <0.001 | 0.34 |
| VerifyNow ® PRU Post dose | 267 (40) | 29 (39) | <0.001 | 20 (19) | <0.001 | 0.73 |
| VerifyNow ® % inhibition Pre dose | 3 (5) | 78 (20) | <0.001 | 83 (14) | <0.001 | 0.34 |

TABLE 24-continued

| | | | Platelet Reactivity | | | |
|---|---|---|---|---|---|---|
| | Placebo N = 64 | Ticagrelor 60 mg N = 58 | p value 60 mg vs placebo | Ticagrelor 90 mg N = 58 | p value 90 mg vs placebo | p value 90 mg vs 60 mg |
| VerifyNow ® % inhibition Post dose | 4 (6) | 90 (13) | <0.001 | 92 (8) | <0.001 | 0.59 |
| LTA Max response Pre dose | 73 (10) | 39 (12) | <0.001 | 36 (14) | <0.001 | 0.18 |
| LTA Max response Post dose | 73 (9) | 33 (12) | <0.001 | 29 (11) | <0.001 | 0.053 |

Data are mean (SD).
Max response: maximum % aggregation response.

Other Embodiments

Should the meaning of the terms in any of the portions of the patents or publications incorporated by reference conflict with the meaning of the terms used in this disclosure, the meaning of the terms in this disclosure controls. In one aspect, the present disclosure provides a method for reducing the rate of cardiovascular death, myocardial infarction, or stroke in a patient in recognized need thereof, comprising administering to the patient a pharmaceutical composition comprising 60 mg ticagrelor twice daily, wherein the patient is also administered a daily maintenance dose of aspirin of 75 to 150 mg, and further wherein the rate of cardiovascular death, myocardial infarction, or stroke in the patient is reduced relative to a dosing regimen where the patient receives the daily maintenance dose of aspirin of 75 to 150 mg only.

In some embodiments, the daily maintenance dose of aspirin is 75 mg to 100 mg.

In some embodiments, the daily maintenance dose of aspirin is 75 mg to 81 mg.

In some embodiments, the daily maintenance dose of aspirin is 100 mg.

In some embodiments, the patient has a history of myocardial infarction.

In some embodiments, the patient has a history of myocardial infarction as a result of a ST-segment-elevation myocardial infarction.

In some embodiments, the patient has a history of myocardial infarction at least 12 months prior to the twice daily administration of the pharmaceutical composition comprising 60 mg ticagrelor and a pharmaceutically acceptable carrier.

In some embodiments, the patient has a history of myocardial infarction 12 to 36 months prior to the twice daily administration of the pharmaceutical composition comprising 60 mg ticagrelor and a pharmaceutically acceptable carrier.

In some embodiments, the patient has a coronary stent.

In some embodiments, the patient is also administered a lipid lowering therapy.

In some embodiments, the patient is also administered at least one medication selected from a statin, beta-blocker, ACEI, or ARB.

In some embodiments, the patient satisfies the inclusion criteria for the PEGASUS-TIMI 54 study listed in Table 2.

In some embodiments, the patient is at least 50 years old. In some further embodiments, the patient is at least 65 years old.

In some embodiments, the patient has diabetes mellitus requiring medication.

In some embodiments, the patient has a history of angiographic evidence of a multivessel CAD.

In some embodiments, the patient has chronic non-end stage renal dysfunction.

In some embodiments, the patient has more than one risk factor atherothrombosis. In some further embodiments, the patient has three or more risk factors for atherothrombosis.

In some embodiments, the patient is Caucasian.

In some embodiments, the patient is Japanese. In some further embodiments, the patient is Japanese and the methods results in a hazard ratio for time to first composite endpoint of cardiovascular death, myocardial infarction, or stroke of 0.29 relative to a dosing regimen where the patient receives the daily maintenance dose of aspirin of 75 mg to 150 mg only.

In some embodiments, the patient has hypertension.

In some embodiments, the patient has hypercholesterolemia.

In some embodiments, the patient is a current smoker.

In some embodiments, the patient has a history of more than one prior myocardial infarction.

In some embodiments, the patient has peripheral artery disease.

In some embodiments, the patient has a history of percutaneous coronary intervention (PCI).

In some embodiments, the patient has a creatinine clearance of less than 60 mL/min.

In some embodiments, the patient does not meet any of the exclusion criteria for the PEGASUS-TIMI 54 study listed in Table 2.

In some embodiments, the patient is not taking dipyridamole or cilostazol.

In some embodiments, the patient is not taking a potent inducer, inhibitor, or substrate of CYP3A.

In some embodiments, the patient does not have chronic anticoagulation.

In some embodiments, the patient does not have a known bleeding diathesis or coagulation disorder.

In some embodiments, the patient is not at increased risk of bleeding due to:
  A history of intracranial bleed at any time,
  A central nervous system tumor or intracranial vascular abnormality (eg, aneurysm, arteriovenous malformation) at any time,
  Intracranial or spinal cord surgery within 5 years, or
  A gastrointestinal (GI) bleed within the past 6 months, or major surgery within 30 days In some embodiments, the patient does not have a history of ischemic stroke.

In some embodiments, the patient is not considered to be at risk of bradycardic events.

In some embodiments, the patient is considered to be at risk of bradycardic events but is treated with a permanent pacemaker.

In some embodiments, the patient has not undergone coronary-artery bypass grafting in the last 5 years.

In some embodiments, the patient does not have known severe liver disease.

In some embodiments, the patient has a life expectancy of at least one year.

In some embodiments, the patient has a history of myocardial infarction as a result of an acute coronary syndrome. In some further embodiments, prior to the administration, the patient was administered twice daily a pharmaceutical composition comprising 90 mg ticagrelor and a pharmaceutically acceptable carrier for a portion of 12 months after the acute coronary syndrome. In some further embodiments, prior to the administration, the patient was administered twice daily a pharmaceutical composition comprising 90 mg ticagrelor and a pharmaceutically acceptable carrier for 12 months after the acute coronary syndrome. In still some further embodiments, prior to the administration, the patient was administered a pharmaceutical composition comprising a 180 mg ticagrelor loading dose prior to administration twice daily of a pharmaceutical composition comprising 90 mg ticagrelor and a pharmaceutically acceptable carrier for a portion of the 12 months after the acute coronary syndrome.

In some embodiments, the patient was previous treated with an ADP receptor blocker. In some further embodiments, the patient was previous treated with an ADP receptor blocker selected from clopidogrel, prasugrel, ticlodipine, or ticagrelor.

In some embodiments, the patient's last dose of ADP receptor blocker occurred less than 7 days prior to administration. In some embodiments, the patient's last dose of ADP receptor blocker occurred 8 to 90 days prior to administration. In some embodiments, the patient's last dose of ADP receptor blocker occurred within 30 days prior to administration. In some embodiments, the patient's last dose of ADP receptor blocker occurred 3 to 12 months prior to administration. In some embodiments, the patient's last dose of ADP receptor blocker occurred more than 12 months prior to administration.

In some embodiments, the primary efficacy endpoint in a patient subgroup is consistent with the primary efficacy subgroup analyses shown in FIGS. 4-7.

In some embodiments, TIMI major bleeding in a patient subgroup is consistent with the TIMI major bleeding subgroup analyses shown in FIGS. 9-11.

In some embodiments, safety and tolerability endpoints are consistent with the data shown in Table 14.

In some embodiments, bleeding events are consistent with the data shown in Table 15.

In some embodiments, adverse events occur at rates consistent with those disclosed in Tables 16 and 17.

In some embodiments, the average risk at three years for patients less than 65 years of age is consistent with the data shown in Table 18.

In some embodiments, the average risk at three years for patients 65 to 75 years of age is consistent with the data shown in Table 18.

In some embodiments, the average risk at three years for patients over 75 years of age is consistent with the data shown in Table 18.

In some embodiments, the Kaplan-Meier rate of patients without TIMI Major Bleeding events vs. time is consistent with the curves shown in FIG. 18.

In some embodiments, the safety and efficacy outcomes at 3 years by time from $P2Y_{12}$ inhibitor withdrawal to randomization are consistent with the data shown in Table 22.

In some embodiments, the method results in platelet reactivity consistent with the data shown in Table 24.

In some embodiments, the method satisfies at least one of the following efficacy endpoints:

1. the method numerically reduces the rate of the composite endpoint of cardiovascular death, myocardial infarction, or stroke relative to a dosing regimen where the patient receives the daily maintenance dose of aspirin of 75 mg to 150 mg only;
2. the method numerically reduces the absolute risk of the composite endpoint of cardiovascular death, myocardial infarction, or stroke relative to a dosing regimen where the patient receives the daily maintenance dose of aspirin of 75 mg to 150 mg only;
3. the method results in a relative risk of the composite endpoint of cardiovascular death, myocardial infarction, or stroke of less than one relative to a dosing regimen where the patient receives the daily maintenance dose of aspirin of 75 mg to 150 mg only;
4. the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only;
5. the method results in a statistically significant reduction in the rate of the composite endpoint of cardiovascular death, myocardial infarction, or stroke relative to a dosing regimen where the patient receives the daily maintenance dose of aspirin of 75 mg to 150 mg only;
6. the method results in a relative risk of the composite endpoint of cardiovascular death, myocardial infarction, or stroke that is statistically significantly less than one relative to a dosing regimen where the patient receives the daily maintenance dose of aspirin of 75 mg to 150 mg only;
7. the method results in a Kaplan-Meier rate for the composite endpoint of cardiovascular death, myocardial infarction, or stroke at three years of approximately 7.8%;
8. the method results in a Kaplan-Meier rate for the composite endpoint of cardiovascular death, myocardial infarction, or stroke at three years of 7.8%;
9. the method results in a Kaplan-Meier rate for the composite endpoint of cardiovascular death, myocardial infarction, or stroke at three years of 7.77%;
10. the method results in a hazard ratio for the composite endpoint of cardiovascular death, myocardial infarction, or stroke of less than 1 relative to a dosing regimen where the patient receives the daily maintenance dose of aspirin of 75 mg to 150 mg only;
11. the method results in a hazard ratio for time to first composite endpoint of cardiovascular death, myocardial infarction, or stroke that is statistically significantly less than 1 relative to a dosing regimen where the patient receives the daily maintenance dose of aspirin of 75 mg to 150 mg only;
12. the method results in a numerical reduction in the percentage of patients with composite endpoint of cardiovascular death, myocardial infarction, or stroke events relative to a dosing regimen where the patient receives the daily maintenance dose of aspirin of 75 mg to 150 mg only;
13. the method results in a hazard ratio for time to first composite endpoint of cardiovascular death, myocardial infarction, or stroke at three years of approximately 0.84 relative to a dosing regimen where the patient receives the daily maintenance dose of aspirin of 75 mg to 150 mg only;

14. the method results in a hazard ratio for time to first composite endpoint of cardiovascular death, myocardial infarction, or stroke at three years of 0.84 relative to a dosing regimen where the patient receives the daily maintenance dose of aspirin of 75 mg to 150 mg only;
15. the method results in a hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only;
16. the method results in a 95% confidence interval for the hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only;
17. the method reduces the absolute risk of the composite endpoint of cardiovascular death, myocardial infarction, or stroke at three years by approximately 1.27% relative to a dosing regimen where the patient receives the daily maintenance dose of aspirin of 75 mg to 150 mg only;
18. the method reduces the absolute risk of the composite endpoint of cardiovascular death, myocardial infarction, or stroke at three years by 1.27% relative to a dosing regimen where the patient receives the daily maintenance dose of aspirin of 75 mg to 150 mg only;
19. the method results in an approximately 17% relative risk reduction for the composite endpoint of cardiovascular death, myocardial infarction, or stroke from 1 to 360 days relative to a dosing regimen where the patient receives the daily maintenance dose of aspirin of 75 mg to 150 mg only;
20. the method results in 17% relative risk reduction for the composite endpoint of cardiovascular death, myocardial infarction, or stroke from 1 to 360 days relative to a dosing regimen where the patient receives the daily maintenance dose of aspirin of 75 mg to 150 mg only;
21. the method reduces the Kaplan-Meier rate for the composite endpoint of cardiovascular death, myocardial infarction, or stroke at three years by approximately 1.2% compared to a dosing regimen where the patient receives the daily maintenance dose of aspirin of 75 mg to 150 mg only;
22. the method reduces the Kaplan-Meier rate for the composite endpoint of cardiovascular death, myocardial infarction, or stroke at three years by 1.2% compared to a dosing regimen where the patient receives the daily maintenance dose of aspirin of 75 mg to 150 mg only;
23. the method reduces the percentage of patients with composite endpoint of cardiovascular death, myocardial infarction, or stroke events at three years by approximately 1.3% relative to a dosing regimen where the patient receives the daily maintenance dose of aspirin of 75 mg to 150 mg only;
24. the method reduces the percentage of patients with composite endpoint of cardiovascular death, myocardial infarction, or stroke events at three years by 1.3% relative to a dosing regimen where the patient receives the daily maintenance dose of aspirin of 75 mg to 150 mg only;
25. the method numerically reduces the absolute risk of at least one of cardiovascular death, myocardial infarction, or stroke relative to a dosing regimen where the patient receives the daily maintenance dose of aspirin of 75 mg to 150 mg only;
26. the method results in a relative risk of less than one for at least one of cardiovascular death, myocardial infarction, or stroke relative to a dosing regimen where the patient receives the daily maintenance dose of aspirin of 75 mg to 150 mg only;
27. the method numerically reduces the Kaplan-Meier rate for at least one of cardiovascular death, myocardial infarction, or stroke compared to a dosing regimen where the patient receives the daily maintenance dose of aspirin of 75 mg to 150 mg only;
28. the method results in a relative risk for time to first cardiovascular death event of less than 1 relative to a dosing regimen where the patient receives the daily maintenance dose of aspirin of 75 mg to 150 mg only;
29. the method results in a hazard ratio for time to first cardiovascular death event of less than 1 relative to a dosing regimen where the patient receives the daily maintenance dose of aspirin of 75 mg to 150 mg only;
30. the method results in a numerical reduction in the percentage of patients with a cardiovascular death event relative to a dosing regimen where the patient receives the daily maintenance dose of aspirin of 75 mg to 150 mg only;
31. the method results in a Kaplan-Meier rate for cardiovascular death at three years of approximately 2.9%;
32. the method results in a Kaplan-Meier rate for cardiovascular death at three years of 2.9%;
33. the method reduces the Kaplan-Meier rate for cardiovascular death at three years by approximately 0.5% compared to a dosing regimen where the patient receives the daily maintenance dose of aspirin of 75 mg to 150 mg only;
34. the method reduces the Kaplan-Meier rate for cardiovascular death at three years by 0.5% compared to a dosing regimen where the patient receives the daily maintenance dose of aspirin of 75 mg to 150 mg only;
35. the method results in a hazard ratio for time to first cardiovascular death event at three years of approximately 0.83 relative to a dosing regimen where the patient receives the daily maintenance dose of aspirin of 75 mg to 150 mg only;
36. the method results in a hazard ratio for time to first cardiovascular death event at three years of 0.83 relative to a dosing regimen where the patient receives the daily maintenance dose of aspirin of 75 mg to 150 mg only;
37. the method results in a hazard ratio for time to first cardiovascular death event at three years of 0.68 to 1.01 relative to a dosing regimen where the patient receives the daily maintenance dose of aspirin of 75 mg to 150 mg only;
38. the method results in a 95% confidence interval for the hazard ratio for time to first cardiovascular death event at three years of 0.68 to 1.01 relative to a dosing regimen where the patient receives the daily maintenance dose of aspirin of 75 mg to 150 mg only;
39. the method results in a hazard ratio for time to first myocardial infarction event of less than 1 relative to a dosing regimen where the patient receives the daily maintenance dose of aspirin of 75 mg to 150 mg only;
40. the method results in a relative risk for time to first myocardial infarction event of less than 1 relative to a dosing regimen where the patient receives the daily maintenance dose of aspirin of 75 mg to 150 mg only;

41. the method results in a numerical reduction in the percentage of patients with a myocardial infarction event relative to a dosing regimen where the patient receives the daily maintenance dose of aspirin of 75 mg to 150 mg only;
42. the method results in a reduction in the percentage of patients with a myocardial infarction event relative to a dosing regimen where the patient receives the daily maintenance dose of aspirin of 75 mg to 150 mg only;
43. the method results in a hazard ratio for time to first myocardial infarction event at three years of approximately 0.84 relative to a dosing regimen where the patient receives the daily maintenance dose of aspirin of 75 mg to 150 mg only;
44. the method results in a hazard ratio for time to first myocardial infarction event at three years of 0.84 relative to a dosing regimen where the patient receives the daily maintenance dose of aspirin of 75 mg to 150 mg only;
45. the method results in a hazard ratio for time to first myocardial infarction event at three years of 0.72 to 0.98 relative to a dosing regimen where the patient receives the daily maintenance dose of aspirin of 75 mg to 150 mg only;
46. the method results in a 95% confidence interval for the hazard ratio for time to first myocardial infarction event at three years of 0.72 to 0.98 relative to a dosing regimen where the patient receives the daily maintenance dose of aspirin of 75 mg to 150 mg only;
47. the method results in a Kaplan-Meier rate for myocardial infarction at three years of approximately 4.5%;
48. the method results in a Kaplan-Meier rate for myocardial infarction at three years of 4.5%;
49. the method reduces the Kaplan-Meier rate for myocardial infarction at three years by approximately 0.7% compared to a dosing regimen where the patient receives the daily maintenance dose of aspirin of 75 mg to 150 mg only;
50. the method reduces the Kaplan-Meier rate for myocardial infarction at three years by 0.7% compared to a dosing regimen where the patient receives the daily maintenance dose of aspirin of 75 mg to 150 mg only;
51. the method results in a hazard ratio for time to first stroke event of less than 1 relative to a dosing regimen where the patient receives the daily maintenance dose of aspirin of 75 mg to 150 mg only;
52. the method results in a relative risk for time to first stroke event of less than 1 relative to a dosing regimen where the patient receives the daily maintenance dose of aspirin of 75 mg to 150 mg only;
53. the method results in a numerical reduction in the percentage of patients with a stroke event relative to a dosing regimen where the patient receives the daily maintenance dose of aspirin of 75 mg to 150 mg only;
54. the method results in a hazard ratio for time to first stroke event at three years of approximately 0.75 relative to a dosing regimen where the patient receives the daily maintenance dose of aspirin of 75 mg to 150 mg only;
55. the method results in a hazard ratio for time to first stroke event at three years of 0.75 relative to a dosing regimen where the patient receives the daily maintenance dose of aspirin of 75 mg to 150 mg only;
56. the method results in a hazard ratio for time to first stroke event at three years of 0.57 to 0.98 relative to a dosing regimen where the patient receives the daily maintenance dose of aspirin of 75 mg to 150 mg only;
57. the method results in a 95% confidence interval for the hazard ratio for time to first stroke event at three years of 0.57 to 0.98 relative to a dosing regimen where the patient receives the daily maintenance dose of aspirin of 75 mg to 150 mg only;
58. the method results in a Kaplan-Meier rate for stroke at three years of approximately 1.5%;
59. the method results in a Kaplan-Meier rate for stroke at three years of 1.5%;
60. the method reduces the Kaplan-Meier rate for stroke at three years by approximately 0.5% compared to a dosing regimen where the patient receives the daily maintenance dose of aspirin of 75 mg to 150 mg only;
61. the method reduces the Kaplan-Meier rate for stroke at three years by 0.5% compared to a dosing regimen where the patient receives the daily maintenance dose of aspirin of 75 mg to 150 mg only;
62. the method results in a hazard ratio for time to first ischemic stroke event of less than 1 relative to a dosing regimen where the patient receives the daily maintenance dose of aspirin of 75 mg to 150 mg only;
63. the method results in a relative risk for time to first ischemic stroke event of less than 1 relative to a dosing regimen where the patient receives the daily maintenance dose of aspirin of 75 mg to 150 mg only;
64. the method results in a numerical reduction in the percentage of patients with an ischemic stroke event relative to a dosing regimen where the patient receives the daily maintenance dose of aspirin of 75 mg to 150 mg only;
65. the method results in a hazard ratio for time to first ischemic stroke event at three years of approximately 0.76 relative to a dosing regimen where the patient receives the daily maintenance dose of aspirin of 75 mg to 150 mg only;
66. the method results in a hazard ratio for time to first ischemic stroke event at three years of 0.76 relative to a dosing regimen where the patient receives the daily maintenance dose of aspirin of 75 mg to 150 mg only;
67. the method results in a hazard ratio for time to first ischemic stroke event at three years of 0.56 to 1.02 relative to a dosing regimen where the patient receives the daily maintenance dose of aspirin of 75 mg to 150 mg only;
68. the method results in a 95% confidence interval for the hazard ratio for time to first ischemic stroke event at three years of 0.56 to 1.02 relative to a dosing regimen where the patient receives the daily maintenance dose of aspirin of 75 mg to 150 mg only;
69. the method results in a Kaplan-Meier rate for ischemic stroke at three years of approximately 1.3%;
70. the method results in a Kaplan-Meier rate for ischemic stroke at three years of 1.3%;
71. the method reduces the Kaplan-Meier rate for ischemic stroke at three years by approximately 0.4% compared to a dosing regimen where the patient receives the daily maintenance dose of aspirin of 75 mg to 150 mg only;
72. the method reduces the Kaplan-Meier rate for ischemic stroke at three years by 0.4% compared to a dosing regimen where the patient receives the daily maintenance dose of aspirin of 75 mg to 150 mg only;
73. the method results in a hazard ratio for time to first coronary heart disease death event of less than 1 relative to a dosing regimen where the patient receives the daily maintenance dose of aspirin of 75 mg to 150 mg only;

74. the method results in a relative risk for time to first coronary heart disease death event of less than 1 relative to a dosing regimen where the patient receives the daily maintenance dose of aspirin of 75 mg to 150 mg only;
75. the method results in a numerical reduction in the percentage of patients with a coronary heart disease death event relative to a dosing regimen where the patient receives the daily maintenance dose of aspirin of 75 mg to 150 mg only;
76. the method results in a hazard ratio for time to first coronary heart disease death event at three years of approximately 0.80 relative to a dosing regimen where the patient receives the daily maintenance dose of aspirin of 75 mg to 150 mg only;
77. the method results in a hazard ratio for time to first coronary heart disease death event at three years of 0.80 relative to a dosing regimen where the patient receives the daily maintenance dose of aspirin of 75 mg to 150 mg only;
78. the method results in a hazard ratio for time to first coronary heart disease death event at three years of 0.62 to 1.04 relative to a dosing regimen where the patient receives the daily maintenance dose of aspirin of 75 mg to 150 mg only;
79. the method results in a 95% confidence interval for the hazard ratio for time to first coronary heart disease death event of at three years 0.62 to 1.04 relative to a dosing regimen where the patient receives the daily maintenance dose of aspirin of 75 mg to 150 mg only;
80. the method results in a Kaplan-Meier rate for coronary heart disease death at three years of approximately 1.7%;
81. the method results in a Kaplan-Meier rate for coronary heart disease death at three years of 1.7%;
82. the method reduces the Kaplan-Meier rate for ischemic stroke at three years by approximately 0.4% compared to a dosing regimen where the patient receives the daily maintenance dose of aspirin of 75 mg to 150 mg only;
83. the method reduces the Kaplan-Meier rate for ischemic stroke at three years by 0.4% compared to a dosing regimen where the patient receives the daily maintenance dose of aspirin of 75 mg to 150 mg only;
84. the method numerically reduces the rate of the composite endpoint of coronary heart disease death, myocardial infarction, or stroke relative to a dosing regimen where the patient receives the daily maintenance dose of aspirin of 75 mg to 150 mg only;
85. the method numerically reduces the absolute risk of the composite endpoint of coronary heart disease death, myocardial infarction, or stroke relative to a dosing regimen where the patient receives the daily maintenance dose of aspirin of 75 mg to 150 mg only;
86. the method results in a relative risk of the composite endpoint of coronary heart disease death, myocardial infarction, or stroke of less than one relative to a dosing regimen where the patient receives the daily maintenance dose of aspirin of 75 mg to 150 mg only;
87. the method numerically reduces the Kaplan-Meier rate for the composite endpoint of coronary heart disease death, myocardial infarction, or stroke compared to a dosing regimen where the patient receives the daily maintenance dose of aspirin of 75 mg to 150 mg only.
88. the method results in a relative risk reduction for the composite endpoint of coronary heart disease death, myocardial infarction, or stroke at three years of approximately 17%;
89. the method results in a relative risk reduction for the composite endpoint of coronary heart disease death, myocardial infarction, or stroke at three years of 17%;
90. the method results in a hazard ratio for time to first composite endpoint of coronary heart disease death, myocardial infarction, or stroke of less than 1 relative to a dosing regimen where the patient receives the daily maintenance dose of aspirin of 75 mg to 150 mg only;
91. the method results in a numerical reduction in the percentage of patients with composite endpoint of coronary heart disease death, myocardial infarction, or stroke events relative to a dosing regimen where the patient receives the daily maintenance dose of aspirin of 75 mg to 150 mg only;
92. the method results in a hazard ratio for time to first composite endpoint of coronary heart disease death, myocardial infarction, or stroke at three years of approximately 0.83 relative to a dosing regimen where the patient receives the daily maintenance dose of aspirin of 75 mg to 150 mg only;
93. the method results in a hazard ratio for time to first composite endpoint of coronary heart disease death, myocardial infarction, or stroke at three years of 0.83 relative to a dosing regimen where the patient receives the daily maintenance dose of aspirin of 75 mg to 150 mg only;
94. the method results in a hazard ratio for time to first composite endpoint of coronary heart disease death, myocardial infarction, or stroke at three years of 0.73 to 0.94 relative to a dosing regimen where the patient receives the daily maintenance dose of aspirin of 75 mg to 150 mg only;
95. the method results in a 95% confidence interval for the hazard ratio for time to first composite endpoint of coronary heart disease death, myocardial infarction, or stroke at three years of 0.73 to 0.94 relative to a dosing regimen where the patient receives the daily maintenance dose of aspirin of 75 mg to 150 mg only;
96. the method results in a Kaplan-Meier rate for the composite endpoint of coronary heart disease death, myocardial infarction, or stroke at three years of approximately 7.1%;
97. the method results in a Kaplan-Meier rate for the composite endpoint of coronary heart disease death, myocardial infarction, or stroke at three years of 7.1%;
98. the method reduces the Kaplan-Meier rate for the composite endpoint of coronary heart disease death, myocardial infarction, or stroke at three years by approximately 1.2% compared to a dosing regimen where the patient receives the daily maintenance dose of aspirin of 75 mg to 150 mg only;
99. the method reduces the Kaplan-Meier rate for the composite endpoint of coronary heart disease death, myocardial infarction, or stroke at three years by 1.2% compared to a dosing regimen where the patient receives the daily maintenance dose of aspirin of 75 mg to 150 mg only;
100. the method numerically reduces the rate of the composite endpoint of coronary heart disease death or myocardial infarction relative to a dosing regimen where the patient receives the daily maintenance dose of aspirin of 75 mg to 150 mg only;

101. the method numerically reduces the absolute risk of the composite endpoint of coronary heart disease death or myocardial infarction relative to a dosing regimen where the patient receives the daily maintenance dose of aspirin of 75 mg to 150 mg only;

102. the method results in a relative risk of the composite endpoint of coronary heart disease death or myocardial infarction of less than one relative to a dosing regimen where the patient receives the daily maintenance dose of aspirin of 75 mg to 150 mg only;

103. the method numerically reduces the Kaplan-Meier rate for the composite endpoint of coronary heart disease death or myocardial infarction compared to a dosing regimen where the patient receives the daily maintenance dose of aspirin of 75 mg to 150 mg only;

104. the method results in a hazard ratio for time to first composite endpoint of coronary heart disease death or myocardial infarction of less than 1 relative to a dosing regimen where the patient receives the daily maintenance dose of aspirin of 75 mg to 150 mg only;

105. the method results in a numerical reduction in the percentage of patients with composite endpoint of coronary heart disease death or myocardial infarction events relative to a dosing regimen where the patient receives the daily maintenance dose of aspirin of 75 mg to 150 mg only;

106. the method results in a hazard ratio for time to first composite endpoint of coronary heart disease death or myocardial infarction at three years of approximately 0.84 relative to a dosing regimen where the patient receives the daily maintenance dose of aspirin of 75 mg to 150 mg only;

107. the method results in a hazard ratio for time to first composite endpoint of coronary heart disease death or myocardial infarction at three years of 0.84 relative to a dosing regimen where the patient receives the daily maintenance dose of aspirin of 75 mg to 150 mg only;

108. the method results in a hazard ratio for time to first composite endpoint of coronary heart disease death or myocardial infarction at three years of 0.73 to 0.96 relative to a dosing regimen where the patient receives the daily maintenance dose of aspirin of 75 mg to 150 mg only;

109. the method results in a 95% confidence interval for the hazard ratio for time to first composite endpoint of coronary heart disease death or myocardial infarction at three years of 0.73 to 0.96 relative to a dosing regimen where the patient receives the daily maintenance dose of aspirin of 75 mg to 150 mg only;

110. the method results in a Kaplan-Meier rate for the composite endpoint of coronary heart disease death or myocardial infarction at three years of approximately 5.6%;

111. the method results in a Kaplan-Meier rate for the composite endpoint of coronary heart disease death or myocardial infarction at three years of 5.6%;

112. the method reduces the Kaplan-Meier rate for the composite endpoint of coronary heart disease death or myocardial infarction at three years by 1.1% compared to a dosing regimen where the patient receives the daily maintenance dose of aspirin of 75 mg to 150 mg only;

113. the method reduces the Kaplan-Meier rate for the composite endpoint of coronary heart disease death or myocardial infarction at three years by approximately 1.1% compared to a dosing regimen where the patient receives the daily maintenance dose of aspirin of 75 mg to 150 mg only;

114. the method numerically reduces the rate of the composite endpoint of cardiovascular death or myocardial infarction relative to a dosing regimen where the patient receives the daily maintenance dose of aspirin of 75 mg to 150 mg only;

115. the method numerically reduces the absolute risk of the composite endpoint of cardiovascular death or myocardial infarction relative to a dosing regimen where the patient receives the daily maintenance dose of aspirin of 75 mg to 150 mg only;

116. the method results in a relative risk of the composite endpoint of cardiovascular death or myocardial infarction of less than one relative to a dosing regimen where the patient receives the daily maintenance dose of aspirin of 75 mg to 150 mg only;

117. the method numerically reduces the Kaplan-Meier rate for the composite endpoint of cardiovascular death or myocardial infarction compared to a dosing regimen where the patient receives the daily maintenance dose of aspirin of 75 mg to 150 mg only;

118. the method results in a hazard ratio for time to first composite endpoint of cardiovascular death or myocardial infarction of less than 1 relative to a dosing regimen where the patient receives the daily maintenance dose of aspirin of 75 mg to 150 mg only;

119. the method results in a numerical reduction in the percentage of patients with composite endpoint of cardiovascular death or myocardial infarction events relative to a dosing regimen where the patient receives the daily maintenance dose of aspirin of 75 mg to 150 mg only;

120. the method results in a hazard ratio for time to first composite endpoint of cardiovascular death or myocardial infarction at three years of approximately 0.85 relative to a dosing regimen where the patient receives the daily maintenance dose of aspirin of 75 mg to 150 mg only;

121. the method results in a hazard ratio for time to first composite endpoint of cardiovascular death or myocardial infarction at three years of 0.85 relative to a dosing regimen where the patient receives the daily maintenance dose of aspirin of 75 mg to 150 mg only;

122. the method results in a hazard ratio for time to first composite endpoint of cardiovascular death or myocardial infarction at three years of 0.74 to 0.96 relative to a dosing regimen where the patient receives the daily maintenance dose of aspirin of 75 mg to 150 mg only;

123. the method results in a 95% confidence interval for the hazard ratio for time to first composite endpoint of cardiovascular death or myocardial infarction at three years of 0.74 to 0.96 relative to a dosing regimen where the patient receives the daily maintenance dose of aspirin of 75 mg to 150 mg only;

124. the method results in a Kaplan-Meier rate for the composite endpoint of cardiovascular death or myocardial infarction at three years of approximately 6.8%;

125. the method results in a Kaplan-Meier rate for the composite endpoint of cardiovascular death or myocardial infarction at three years of 6.8%;

126. the method reduces the Kaplan-Meier rate for the composite endpoint of cardiovascular death or myocardial infarction at three years by approximately 1.0% compared to a dosing regimen where the patient receives the daily maintenance dose of aspirin of 75 mg to 150 mg only;

127. the method reduces the Kaplan-Meier rate for the composite endpoint of cardiovascular death or myocardial infarction at three years by 1.0% compared to a dosing regimen where the patient receives the daily maintenance dose of aspirin of 75 mg to 150 mg only;

128. the method numerically reduces the rate of death from any cause relative to a dosing regimen where the patient receives the daily maintenance dose of aspirin of 75 mg to 150 mg only;

129. the method numerically reduces the Kaplan-Meier rate for death from any cause compared to a dosing regimen where the patient receives the daily maintenance dose of aspirin of 75 mg to 150 mg only;

130. the method results in a hazard ratio for time to first death from any cause of less than 1 relative to a dosing regimen where the patient receives the daily maintenance dose of aspirin of 75 mg to 150 mg only;

131. the method results in a relative risk for time to first death from any cause of less than 1 relative to a dosing regimen where the patient receives the daily maintenance dose of aspirin of 75 mg to 150 mg only;

132. the method results in a numerical reduction in the percentage of patients with death from any cause events relative to a dosing regimen where the patient receives the daily maintenance dose of aspirin of 75 mg to 150 mg only;

133. the method results in a hazard ratio for time to first death from any cause at three years of approximately 0.89 relative to a dosing regimen where the patient receives the daily maintenance dose of aspirin of 75 mg to 150 mg only;

134. the method results in a hazard ratio for time to first death from any cause at three years of 0.89 relative to a dosing regimen where the patient receives the daily maintenance dose of aspirin of 75 mg to 150 mg only;

135. the method results in a hazard ratio for time to first death from any cause at three years of 0.76 to 1.04 relative to a dosing regimen where the patient receives the daily maintenance dose of aspirin of 75 mg to 150 mg only;

136. the method results in a 95% confidence interval for the hazard ratio for time to first death from any cause at three years of 0.76 to 1.04 relative to a dosing regimen where the patient receives the daily maintenance dose of aspirin of 75 mg to 150 mg only.

137. the method results in a Kaplan-Meier rate for death from any cause at three years of approximately 4.7%;

138. the method results in a Kaplan-Meier rate for death from any cause at three years of 4.7%;

139. the method reduces the Kaplan-Meier rate for death from any cause at three years by approximately 0.5% compared to a dosing regimen where the patient receives the daily maintenance dose of aspirin of 75 mg to 150 mg only;

the method reduces the Kaplan-Meier rate for death from any cause at three years by 0.5% compared to a dosing regimen where the patient receives the daily maintenance dose of aspirin of 75 mg to 150 mg only;

140. the method numerically reduces the rate of urgent coronary revascularization for unstable angina from any cause relative to a dosing regimen where the patient receives the daily maintenance dose of aspirin of 75 mg to 150 mg only;

141. the method numerically reduces the Kaplan-Meier rate for urgent coronary revascularization for unstable angina compared to a dosing regimen where the patient receives the daily maintenance dose of aspirin of 75 mg to 150 mg only;

142. the method results in a hazard ratio for time to first urgent coronary revascularization for unstable angina of less than 1 relative to a dosing regimen where the patient receives the daily maintenance dose of aspirin of 75 mg to 150 mg only;

143. the method results in a numerical reduction in the percentage of patients with urgent coronary revascularization for unstable angina events relative to a dosing regimen where the patient receives the daily maintenance dose of aspirin of 75 mg to 150 mg only;

144. the method results in a hazard ratio for time to first urgent coronary revascularization for unstable angina at three years of approximately 0.82 relative to a dosing regimen where the patient receives the daily maintenance dose of aspirin of 75 mg to 150 mg only;

145. the method results in a hazard ratio for time to first urgent coronary revascularization for unstable angina at three years of 0.82 relative to a dosing regimen where the patient receives the daily maintenance dose of aspirin of 75 mg to 150 mg only;

146. the method results in a hazard ratio for time to first urgent coronary revascularization for unstable angina at three years of 0.58 to 1.14 relative to a dosing regimen where the patient receives the daily maintenance dose of aspirin of 75 mg to 150 mg only;

147. the method results in a 95% confidence interval for the hazard ratio for time to first urgent coronary revascularization for unstable angina at three years of 0.58 to 1.14 relative to a dosing regimen where the patient receives the daily maintenance dose of aspirin of 75 mg to 150 mg only;

148. the method numerically reduces the rate of coronary stent thrombosis from any cause relative to a dosing regimen where the patient receives the daily maintenance dose of aspirin of 75 mg to 150 mg only;

149. the method numerically reduces the Kaplan-Meier rate for coronary stent thrombosis compared to a dosing regimen where the patient receives the daily maintenance dose of aspirin of 75 mg to 150 mg only;

150. the method results in a hazard ratio for time to first coronary stent thrombosis of less than 1 relative to a dosing regimen where the patient receives the daily maintenance dose of aspirin of 75 mg to 150 mg only;

151. the method results in a numerical reduction in the percentage of patients with coronary stent thrombosis events relative to a dosing regimen where the patient receives the daily maintenance dose of aspirin of 75 mg to 150 mg only;

152. the method results in a hazard ratio for time to first coronary stent thrombosis at three years of approximately 0.82 relative to a dosing regimen where the patient receives the daily maintenance dose of aspirin of 75 mg to 150 mg only;

153. the method results in a hazard ratio for time to first coronary stent thrombosis at three years of 0.82 relative to a dosing regimen where the patient receives the daily maintenance dose of aspirin of 75 mg to 150 mg only;

154. the method results in a hazard ratio for time to first coronary stent thrombosis at three years of 0.54 to 1.23 relative to a dosing regimen where the patient receives the daily maintenance dose of aspirin of 75 mg to 150 mg only;

155. the method results in a 95% confidence interval for the hazard ratio for time to first coronary stent thrombosis at three years of 0.54 to 1.23 relative to a dosing regimen where the patient receives the daily maintenance dose of aspirin of 75 mg to 150 mg only;

156. the method results in a relative risk of coronary stent thrombosis of less than one relative to a dosing regimen where the patient receives the daily maintenance dose of aspirin of 75 mg to 150 mg only;

157. the method results in a relative risk reduction of approximately 18% for coronary stent thrombosis at three years relative to a dosing regimen where the patient receives the daily maintenance dose of aspirin of 75 mg to 150 mg only;

158. the method results in a relative risk reduction of 18% for coronary stent thrombosis at three years relative to a dosing regimen where the patient receives the daily maintenance dose of aspirin of 75 mg to 150 mg only;

159. the method numerically reduces the rate of the composite endpoint of cardiovascular death, myocardial infarction, or stroke relative to a dosing regimen where the patient receives the daily maintenance dose of aspirin of 75 mg to 150 mg only in a subgroup shown in FIGS. 4-7, excluding subgroups wherein the hazard ratio for time to first composite endpoint of cardiovascular death, myocardial infarction, or stroke shown in FIGS. 4-7 is greater than 1 relative to a dosing regimen where the patient receives the daily maintenance dose of aspirin of 75 mg to 150 mg only;

160. the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only for a subgroup shown in FIGS. 4-7 to have an average hazard ratio less than 1;

161. the method results in a numerical reduction in the percentage of patients with composite endpoint of cardiovascular death, myocardial infarction, or stroke events relative to a dosing regimen where the patient receives the daily maintenance dose of aspirin of 75 mg to 150 mg only for a subgroup shown in FIGS. 4-7 to have an average hazard ratio less than 1;

162. the method results in a hazard ratio for time to first composite endpoint of cardiovascular death, myocardial infarction, or stroke as shown in FIGS. 4-7 relative to a dosing regimen where the patient receives the daily maintenance dose of aspirin of 75 mg to 150 mg only for a subgroup shown in FIGS. 4-7;

163. the method results in a 95% confidence interval for the hazard ratio for time to first composite endpoint of cardiovascular death, myocardial infarction, or stroke as shown in FIGS. 4-7 relative to a dosing regimen where the patient receives the daily maintenance dose of aspirin of 75 mg to 150 mg only for a subgroup shown in FIGS. 4-7;

164. the method results in an absolute risk reduction for the composite endpoint of cardiovascular death, myocardial infarction, and stroke at three years of approximately 2.15%, wherein the patient is more than 75 years of age;

165. the method results in an absolute risk reduction for the composite endpoint of cardiovascular death, myocardial infarction, and stroke at three years of 2.15%, wherein the patient is more than 75 years of age;

166. the method results in an absolute risk reduction for the composite endpoint of cardiovascular death, myocardial infarction, and stroke at three years of approximately 1.38%, wherein the patient is less than 65 years of age;

167. the method results in an absolute risk reduction for the composite endpoint of cardiovascular death, myocardial infarction, and stroke at three years of 1.38%, wherein the patient is less than 65 years of age;

168. the method numerically reduces the rate of the composite endpoint of cardiovascular death, myocardial infarction, stroke, or TIMI major bleeding relative to a dosing regimen where the patient receives the daily maintenance dose of aspirin of 75 mg to 150 mg only;

169. the method numerically reduces the absolute risk of the composite endpoint of cardiovascular death, myocardial infarction, stroke, or TIMI major bleeding relative to a dosing regimen where the patient receives the daily maintenance dose of aspirin of 75 mg to 150 mg only;

170. the method numerically reduces the relative risk of the composite endpoint of cardiovascular death, myocardial infarction, stroke, or TIMI major bleeding compared to a dosing regimen where the patient receives the daily maintenance dose of aspirin of 75 mg to 150 mg only;

171. the method results in a hazard ratio for time to first composite endpoint of cardiovascular death, myocardial infarction, stroke, or TIMI major bleeding of less than 1 relative to a dosing regimen where the patient receives the daily maintenance dose of aspirin of 75 mg to 150 mg only;

172. the method results in a numerical reduction in the percentage of patients with the composite endpoint of cardiovascular death, myocardial infarction, stroke, or TIMI major bleeding events relative to a dosing regimen where the patient receives the daily maintenance dose of aspirin of 75 mg to 150 mg only;

173. the method results in a hazard ratio for time to first composite endpoint of cardiovascular death, myocardial infarction, stroke, or TIMI major bleeding at three years of approximately 0.95 relative to a dosing regimen where the patient receives the daily maintenance dose of aspirin of 75 mg to 150 mg only;

174. the method results in a hazard ratio for time to first composite endpoint of cardiovascular death, myocardial infarction, stroke, or TIMI major bleeding at three years of 0.95 relative to a dosing regimen where the patient receives the daily maintenance dose of aspirin of 75 mg to 150 mg only;

175. the method results in a hazard ratio for time to first composite endpoint of cardiovascular death, myocardial infarction, stroke, or TIMI major bleeding at three years of 0.85 to 1.06 relative to a dosing regimen where the patient receives the daily maintenance dose of aspirin of 75 mg to 150 mg only;

176. the method results in a 95% confidence interval for the hazard ratio for time to first composite endpoint of cardiovascular death, myocardial infarction, stroke, or TIMI major bleeding at three years of 0.85 to 1.06 relative to a dosing regimen where the patient receives the daily maintenance dose of aspirin of 75 mg to 150 mg only;

177. the method results in a relative risk reduction of approximately 5% for the composite endpoint of cardiovascular death, myocardial infarction, stroke, or TIMI major bleeding at three years relative to a dosing regimen where the patient receives the daily maintenance dose of aspirin of 75 mg to 150 mg only;

178. the method results in a relative risk reduction of 5% for the composite endpoint of cardiovascular death, myocardial infarction, stroke, or TIMI major bleeding at three years relative to a dosing regimen where the patient receives the daily maintenance dose of aspirin of 75 mg to 150 mg only;

179. the method numerically reduces the rate of the composite endpoint of cardiovascular death, myocardial infarction, stroke, intracranial hemorrhage, or fatal bleeding relative to a dosing regimen where the patient receives the daily maintenance dose of aspirin of 75 mg to 150 mg only;

180. the method numerically reduces the absolute risk of the composite endpoint of cardiovascular death, myocardial infarction, stroke, intracranial hemorrhage, or fatal bleeding relative to a dosing regimen where the patient receives the daily maintenance dose of aspirin of 75 mg to 150 mg only;

181. the method results in a relative risk of the composite endpoint of cardiovascular death, myocardial infarction, stroke, intracranial hemorrhage, or fatal bleeding of less than one relative to a dosing regimen where the patient receives the daily maintenance dose of aspirin of 75 mg to 150 mg only;

182. the method results in a hazard ratio for time to first composite endpoint of cardiovascular death, myocardial infarction, stroke, intracranial hemorrhage, or fatal bleeding of less than 1 relative to a dosing regimen where the patient receives the daily maintenance dose of aspirin of 75 mg to 150 mg only;

183. the method results in a numerical reduction in the percentage of patients with the composite endpoint of cardiovascular death, myocardial infarction, stroke, intracranial hemorrhage, or fatal bleeding events relative to a dosing regimen where the patient receives the daily maintenance dose of aspirin of 75 mg to 150 mg only;

184. the method results in a hazard ratio for time to first composite endpoint of cardiovascular death, myocardial infarction, stroke, intracranial hemorrhage, or fatal bleeding of less than one relative to a dosing regimen where the patient receives the daily maintenance dose of aspirin of 75 mg to 150 mg only;

185. the method results in a hazard ratio for time to first composite endpoint of cardiovascular death, myocardial infarction, stroke, intracranial hemorrhage, or fatal bleeding at three years of approximately 0.86 relative to a dosing regimen where the patient receives the daily maintenance dose of aspirin of 75 mg to 150 mg only;

186. the method results in a hazard ratio for time to first composite endpoint of cardiovascular death, myocardial infarction, stroke, intracranial hemorrhage, or fatal bleeding at three years of 0.86 relative to a dosing regimen where the patient receives the daily maintenance dose of aspirin of 75 mg to 150 mg only;

187. the method results in a hazard ratio for time to first composite endpoint of cardiovascular death, myocardial infarction, stroke, intracranial hemorrhage, or fatal bleeding at three years of 0.77 to 0.97 relative to a dosing regimen where the patient receives the daily maintenance dose of aspirin of 75 mg to 150 mg only;

188. the method results in a 95% confidence interval for the hazard ratio for time to first composite endpoint of cardiovascular death, myocardial infarction, stroke, intracranial hemorrhage, or fatal bleeding at three years of 0.77 to 0.97 relative to a dosing regimen where the patient receives the daily maintenance dose of aspirin of 75 mg to 150 mg only;

189. the method results in a relative risk reduction of approximately 14% for the composite endpoint of cardiovascular death, myocardial infarction, stroke, intracranial hemorrhage, or fatal bleeding at three years relative to a dosing regimen where the patient receives the daily maintenance dose of aspirin of 75 mg to 150 mg only;

190. the method results in a relative risk reduction of 14% for the composite endpoint of cardiovascular death, myocardial infarction, stroke, intracranial hemorrhage, or fatal bleeding at three years relative to a dosing regimen where the patient receives the daily maintenance dose of aspirin of 75 mg to 150 mg only;

191. the method results in an absolute risk reduction of approximately 1.27% for the composite endpoint of cardiovascular death, myocardial infarction, or stroke at three years relative to a dosing regimen where the patient receives the daily maintenance dose of aspirin of 75 mg to 150 mg only;

192. the method results in an absolute risk reduction of 1.27% for the composite endpoint of cardiovascular death, myocardial infarction, or stroke at three years relative to a dosing regimen where the patient receives the daily maintenance dose of aspirin of 75 mg to 150 mg only;

193. the method results in an absolute risk reduction of approximately 0.53% for cardiovascular death at three years relative to a dosing regimen where the patient receives the daily maintenance dose of aspirin of 75 mg to 150 mg only;

194. the method results in an absolute risk reduction of 0.53% for cardiovascular death at three years relative to a dosing regimen where the patient receives the daily maintenance dose of aspirin of 75 mg to 150 mg only;

195. the method results in an absolute risk reduction of approximately 0.72% for myocardial infarction at three years relative to a dosing regimen where the patient receives the daily maintenance dose of aspirin of 75 mg to 150 mg only;

196. the method results in an absolute risk reduction of 0.72% for myocardial infarction at three years relative to a dosing regimen where the patient receives the daily maintenance dose of aspirin of 75 mg to 150 mg only;

197. the method results in an absolute risk reduction of approximately 0.47% for myocardial infarction at three years relative to a dosing regimen where the patient receives the daily maintenance dose of aspirin of 75 mg to 150 mg only;

198. the method results in an absolute risk reduction of 0.47% for myocardial infarction relative at three years to a dosing regimen where the patient receives the daily maintenance dose of aspirin of 75 mg to 150 mg only;

199. the method results in a composite endpoint of cardiovascular death, myocardial infarction, or stroke number needed to treat of approximately 79 relative to a dosing regimen where the patient receives the daily maintenance dose of aspirin of 75 mg to 150 mg only;

200. the method results in a composite endpoint of cardiovascular death, myocardial infarction, or stroke number needed to treat of 79 relative to a dosing regimen where the patient receives the daily maintenance dose of aspirin of 75 mg to 150 mg only;

201. the method results in a cardiovascular death number needed to treat of approximately 189 relative to a dosing regimen where the patient receives the daily maintenance dose of aspirin of 75 mg to 150 mg only;

202. the method results in a cardiovascular death number needed to treat of 189 relative to a dosing regimen where the patient receives the daily maintenance dose of aspirin of 75 mg to 150 mg only;
203. the method results in a myocardial infarction number needed to treat of approximately 139 relative to a dosing regimen where the patient receives the daily maintenance dose of aspirin of 75 mg to 150 mg only;
204. the method results in a myocardial infarction number needed to treat of 139 relative to a dosing regimen where the patient receives the daily maintenance dose of aspirin of 75 mg to 150 mg only;
205. the method results in a stroke number needed to treat of approximately 213 relative to a dosing regimen where the patient receives the daily maintenance dose of aspirin of 75 mg to 150 mg only;
206. the method results in a stroke number needed to treat of 213 relative to a dosing regimen where the patient receives the daily maintenance dose of aspirin of 75 mg to 150 mg only;
207. the method results in a hazard ratio for time to first composite endpoint of cardiovascular death, myocardial infarction, or stroke event of less than one relative to a dosing regimen where the patient receives the daily maintenance dose of aspirin of 75 mg to 150 mg only, wherein the patient stopped a previous $P2Y_{12}$ inhibitor therapy within 30 days prior to administration;
208. the method results in a hazard ratio for time to first composite endpoint of cardiovascular death, myocardial infarction, or stroke event at three years of approximately 0.75 relative to a dosing regimen where the patient receives the daily maintenance dose of aspirin of 75 mg to 150 mg only, wherein the patient stopped a previous $P2Y_{12}$ inhibitor therapy within 30 days prior to administration;
209. the method results in a hazard ratio for time to first composite endpoint of cardiovascular death, myocardial infarction, or stroke event at three years of 0.75 relative to a dosing regimen where the patient receives the daily maintenance dose of aspirin of 75 mg to 150 mg only, wherein the patient stopped a previous $P2Y_{12}$ inhibitor therapy within 30 days prior to administration;
210. the method results in a hazard ratio for time to first composite endpoint of cardiovascular death, myocardial infarction, or stroke event at three years of 0.61 to 0.92 relative to a dosing regimen where the patient receives the daily maintenance dose of aspirin of 75 mg to 150 mg only, wherein the patient stopped a previous $P2Y_{12}$ inhibitor therapy within 30 days prior to administration;
211. the method results in a 95% confidence interval for the hazard ratio for time to first composite endpoint of cardiovascular death, myocardial infarction, or stroke event at three years of 0.61 to 0.92 relative to a dosing regimen where the patient receives the daily maintenance dose of aspirin of 75 mg to 150 mg only, wherein the patient stopped a previous $P2Y_{12}$ inhibitor therapy within 30 days prior to administration;
212. the method results in a hazard ratio for time to first composite endpoint of cardiovascular death, myocardial infarction, or stroke event at three years of less than one relative to a dosing regimen where the patient receives the daily maintenance dose of aspirin of 75 mg to 150 mg only, wherein the patient stopped a previous $P2Y_{12}$ inhibitor therapy 30 days to 1 year prior to administration;
213. the method results in a hazard ratio for time to first composite endpoint of cardiovascular death, myocardial infarction, or stroke event at three years of approximately 0.82 relative to a dosing regimen where the patient receives the daily maintenance dose of aspirin of 75 mg to 150 mg only, wherein the patient stopped a previous $P2Y_{12}$ inhibitor therapy 30 days to 1 year prior to administration;
214. the method results in a hazard ratio for time to first composite endpoint of cardiovascular death, myocardial infarction, or stroke event at three years of 0.82 relative to a dosing regimen where the patient receives the daily maintenance dose of aspirin of 75 mg to 150 mg only, wherein the patient stopped a previous $P2Y_{12}$ inhibitor therapy 30 days to 1 year prior to administration;
215. the method results in a hazard ratio for time to first composite endpoint of cardiovascular death, myocardial infarction, or stroke event at three years of 0.65 to 1.02 relative to a dosing regimen where the patient receives the daily maintenance dose of aspirin of 75 mg to 150 mg only, wherein the patient stopped a previous $P2Y_{12}$ inhibitor therapy 31 days to 1 year prior to administration;
216. the method results in a 95% confidence interval for the hazard ratio for time to first composite endpoint of cardiovascular death, myocardial infarction, or stroke event at three years of 0.65 to 1.02 relative to a dosing regimen where the patient receives the daily maintenance dose of aspirin of 75 mg to 150 mg only, wherein the patient stopped a previous $P2Y_{12}$ inhibitor therapy 31 days to 1 year prior to administration;
217. the method results in a relative risk reduction of 27% for the composite endpoint of cardiovascular death, myocardial infarction, or stroke at three years relative to a dosing regimen where the patient receives the daily maintenance dose of aspirin of 75 mg to 150 mg only, wherein the patient stopped a previous $P2Y_{12}$ inhibitor therapy within 30 days prior to administration;
218. the method results in a relative risk reduction of approximately 27% for the composite endpoint of cardiovascular death, myocardial infarction, or stroke at three years relative to a dosing regimen where the patient receives the daily maintenance dose of aspirin of 75 mg to 150 mg only, wherein the patient stopped a previous $P2Y_{12}$ inhibitor therapy within 30 days prior to administration;
219. the method results in an absolute risk reduction of approximately 2.2% for the composite endpoint of cardiovascular death, myocardial infarction, or stroke at three years relative to a dosing regimen where the patient receives the daily maintenance dose of aspirin of 75 mg to 150 mg only, wherein the patient stopped a previous $P2Y_{12}$ inhibitor therapy within 30 days prior to administration;
220. the method results in an absolute risk reduction of 2.2% for the composite endpoint of cardiovascular death, myocardial infarction, or stroke at three years relative to a dosing regimen where the patient receives the daily maintenance dose of aspirin of 75 mg to 150 mg only, wherein the patient stopped a previous $P2Y_{12}$ inhibitor therapy within 30 days prior to administration;
221. the method results in a relative risk reduction of approximately 14% for the composite endpoint of cardiovascular death, myocardial infarction, or stroke at three years relative to a dosing regimen where the patient receives the daily maintenance dose of aspirin of 75 mg to 150 mg only, wherein the patient stopped a previous P2Y$_{12}$ inhibitor therapy 31 days to one year prior to administration;

222. the method results in a relative risk reduction of 14% for the composite endpoint of cardiovascular death, myocardial infarction, or stroke at three years relative to a dosing regimen where the patient receives the daily maintenance dose of aspirin of 75 mg to 150 mg only, wherein the patient stopped a previous P2Y$_{12}$ inhibitor therapy 31 days to one year prior to administration;

223. the method results in an absolute risk reduction of approximately 1.1% for the composite endpoint of cardiovascular death, myocardial infarction, or stroke at three years relative to a dosing regimen where the patient receives the daily maintenance dose of aspirin of 75 mg to 150 mg only, wherein the patient stopped a previous P2Y$_{12}$ inhibitor therapy 31 days to one year prior to administration;

224. the method results in an absolute risk reduction of 1.1% for the composite endpoint of cardiovascular death, myocardial infarction, or stroke at three years relative to a dosing regimen where the patient receives the daily maintenance dose of aspirin of 75 mg to 150 mg only, wherein the patient stopped a previous P2Y$_{12}$ inhibitor therapy 31 days to one year prior to administration;

225. the method numerically reduces the rate of the composite endpoint of cardiovascular death, myocardial infarction, or stroke relative to a dosing regimen where the patient receives the daily maintenance dose of aspirin of 75 mg to 150 mg only, wherein the patient stopped a previous P2Y$_{12}$ inhibitor therapy within 30 days prior to administration;

226. the method numerically reduces the absolute risk of the composite endpoint of cardiovascular death, myocardial infarction, or stroke relative to a dosing regimen where the patient receives the daily maintenance dose of aspirin of 75 mg to 150 mg only, wherein the patient stopped a previous P2Y$_{12}$ inhibitor therapy within 30 days prior to administration;

227. the method results in a relative risk of the composite endpoint of cardiovascular death, myocardial infarction, or stroke of less than one relative to a dosing regimen where the patient receives the daily maintenance dose of aspirin of 75 mg to 150 mg only, wherein the patient stopped a previous P2Y$_{12}$ inhibitor therapy within 30 days prior to administration;

228. the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only, wherein the patient stopped a previous P2Y$_{12}$ inhibitor therapy within 30 days prior to administration;

229. the method results in a Kaplan-Meier rate for the composite endpoint of cardiovascular death, myocardial infarction, or stroke at three years of approximately 8.0%, wherein the patient stopped a previous P2Y$_{12}$ inhibitor therapy within 30 days prior to administration;

230. the method results in a Kaplan-Meier rate for the composite endpoint of cardiovascular death, myocardial infarction, or stroke at three years of 8.0%, wherein the patient stopped a previous P2Y$_{12}$ inhibitor therapy within 30 days prior to administration;

231. the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only, wherein the patient stopped a previous P2Y$_{12}$ inhibitor therapy within 30 days prior to administration;

232. the method results in a numerical reduction in the percentage of patients with composite endpoint of cardiovascular death, myocardial infarction, or stroke events relative to a dosing regimen where the patient receives the daily maintenance dose of aspirin of 75 mg to 150 mg only, wherein the patient stopped a previous P2Y$_{12}$ inhibitor therapy within 30 days prior to administration;

233. the method reduces the Kaplan-Meier rate for the composite endpoint of cardiovascular death, myocardial infarction, or stroke at three years by approximately 1.9% compared to a dosing regimen where the patient receives the daily maintenance dose of aspirin of 75 mg to 150 mg only, wherein the patient stopped a previous P2Y$_{12}$ inhibitor therapy within 30 days prior to administration;

234. the method reduces the Kaplan-Meier rate for the composite endpoint of cardiovascular death, myocardial infarction, or stroke at three years by 1.9% compared to a dosing regimen where the patient receives the daily maintenance dose of aspirin of 75 mg to 150 mg only, wherein the patient stopped a previous P2Y$_{12}$ inhibitor therapy within 30 days prior to administration;

235. the method numerically reduces the rate of the composite endpoint of cardiovascular death, myocardial infarction, or stroke relative to a dosing regimen where the patient receives the daily maintenance dose of aspirin of 75 mg to 150 mg only, wherein the patient stopped a previous P2Y$_{12}$ inhibitor therapy 31 days to one year prior to administration;

236. the method numerically reduces the absolute risk of the composite endpoint of cardiovascular death, myocardial infarction, or stroke relative to a dosing regimen where the patient receives the daily maintenance dose of aspirin of 75 mg to 150 mg only, wherein the patient stopped a previous P2Y$_{12}$ inhibitor therapy 31 days to one year prior to administration;

237. the method results in a relative risk of the composite endpoint of cardiovascular death, myocardial infarction, or stroke of less than one to a dosing regimen where the patient receives the daily maintenance dose of aspirin of 75 mg to 150 mg only, wherein the patient stopped a previous P2Y$_{12}$ inhibitor therapy 31 days to one year prior to administration;

238. the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only, wherein the patient stopped a previous P2Y$_{12}$ inhibitor therapy 31 days to one year prior to administration;

239. the method results in a Kaplan-Meier rate for the composite endpoint of cardiovascular death, myocardial infarction, or stroke at three years of approximately 8.1%, wherein the patient stopped a previous P2Y$_{12}$ inhibitor therapy 31 days to one year prior to administration;

240. the method results in a Kaplan-Meier rate for the composite endpoint of cardiovascular death, myocardial infarction, or stroke at three years of 8.1%, wherein the patient stopped a previous P2Y$_{12}$ inhibitor therapy 31 days to one year prior to administration;
241. the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only, wherein the patient stopped a previous P2Y$_{12}$ inhibitor therapy 31 days to one year prior to administration;
242. the method results in a numerical reduction in the percentage of patients with composite endpoint of cardiovascular death, myocardial infarction, or stroke events relative to a dosing regimen where the patient receives the daily maintenance dose of aspirin of 75 mg to 150 mg only, wherein the patient stopped a previous P2Y$_{12}$ inhibitor therapy 31 days to one year prior to administration;
243. the method reduces the Kaplan-Meier rate for the composite endpoint of cardiovascular death, myocardial infarction, or stroke at three years by approximately 0.6% compared to a dosing regimen where the patient receives the daily maintenance dose of aspirin of 75 mg to 150 mg only, wherein the patient stopped a previous P2Y$_{12}$ inhibitor therapy 31 days to one year prior to administration;
244. the method reduces the Kaplan-Meier rate for the composite endpoint of cardiovascular death, myocardial infarction, or stroke at three years by 0.6% compared to a dosing regimen where the patient receives the daily maintenance dose of aspirin of 75 mg to 150 mg only, wherein the patient stopped a previous P2Y$_{12}$ inhibitor therapy 31 days to one year prior to administration;
245. the method results in a numerical reduction in the rate of all-cause mortality compared to a dosing regimen where the patient receives the daily maintenance dose of aspirin of 75 mg to 150 mg only;
246. the method is as effective in reducing the rate for the composite end point of cardiovascular death, myocardial infarction, or stroke in the patient as a method wherein the patient is administered twice daily a pharmaceutical composition comprising 90 mg ticagrelor and a pharmaceutically acceptable carrier and a daily maintenance dose of aspirin of 75 to 100 mg;
247. the method reduces the rate of irreversible harm to the patient relative to a method wherein the patient is administered twice daily a pharmaceutical composition comprising 90 mg ticagrelor and a pharmaceutically acceptable carrier and a daily maintenance dose of aspirin of 75 to 100 mg;
248. the method reduces the rate of the composite endpoint of cardiovascular death, myocardial infarction, stroke, intracranial hemorrhage, or fatal bleeding relative to a method wherein the patient is administered twice daily a pharmaceutical composition comprising 90 mg ticagrelor and a pharmaceutically acceptable carrier and a daily maintenance dose of aspirin of 75 to 100 mg;
249. the method numerically reduces the rate of the composite endpoint of cardiovascular death, myocardial infarction, stroke, intracranial hemorrhage, or fatal bleeding relative to a method wherein the patient is administered twice daily a pharmaceutical composition comprising 90 mg ticagrelor and a pharmaceutically acceptable carrier and a daily maintenance dose of aspirin of 75 to 100 mg;
250. the method improves the risk-benefit profile relative to a method wherein the patient is administered twice daily a pharmaceutical composition comprising 90 mg ticagrelor and a pharmaceutically acceptable carrier and a daily maintenance dose of aspirin of 75 to 100 mg; or
251. the method improves the risk-benefit profile of ticagrelor administered on a background of aspirin.

In some embodiments, the method satisfies at least one of the following safety endpoints:
1. the method does not result in a hazard ratio for fatal bleeding at 3 years of greater than one relative to a dosing regimen where the patient receives a daily maintenance dose of aspirin of 75 mg to 150 mg only;
2. the method does not result in a hazard ratio for fatal bleeding at 3 years that is nominally significantly greater than one relative to a dosing regimen where the patient receives a daily maintenance dose of aspirin of 75 mg to 150 mg only;
3. the method does not result in a hazard ratio for intracranial hemorrhage at 3 years of greater than one relative to a dosing regimen where the patient receives a daily maintenance dose of aspirin of 75 mg to 150 mg only;
4. the method does not result in a hazard ratio for intracranial hemorrhage at 3 years that is nominally significantly greater than one relative to a dosing regimen where the patient receives a daily maintenance dose of aspirin of 75 mg to 150 mg only;
5. the method results in a numerical increase in the number of TIMI major bleeding events per 100 patient years of less than 0.5 relative to a dosing regimen where the patient receives the daily maintenance dose of aspirin of 75 mg to 150 mg only;
6. the method results in a numerical increase in the number of TIMI major bleeding events per 100 patient years of approximately 0.44 relative to a dosing regimen where the patient receives the daily maintenance dose of aspirin of 75 mg to 150 mg only;
7. the method results in a numerical increase in the number of TIMI major bleeding events per 100 patient years of 0.44 relative to a dosing regimen where the patient receives the daily maintenance dose of aspirin of 75 mg to 150 mg only;
8. the method does not result in a numerical increase in the number of fatal bleeding events per 100 patient years relative to a dosing regimen where the patient receives the daily maintenance dose of aspirin of 75 mg to 150 mg only;
9. the method results in a numerical increase in the number of intracranial hemorrhage events per 100 patient years of approximately 0.05 relative to a dosing regimen where the patient receives the daily maintenance dose of aspirin of 75 mg to 150 mg only;
10. the method results in a numerical increase in the number of intracranial hemorrhage events per 100 patient years of 0.05 relative to a dosing regimen where the patient receives the daily maintenance dose of aspirin of 75 mg to 150 mg only;
11. the method results in a difference in the Kaplan-Meier rate of fatal bleeding at three years of less than 0.05% relative to a dosing regimen where the patient receives the daily maintenance dose of aspirin of 75 mg to 150 mg only;
12. the method results in a difference in the Kaplan-Meier rate of intracranial hemorrhage at three years of less than 0.1% relative to a dosing regimen where the patient receives the daily maintenance dose of aspirin of 75 mg to 150 mg only;
13. the method results in a Kaplan-Meier rate for fatal bleeding at three years of approximately 0.3%;
14. the method results in a Kaplan-Meier rate for fatal bleeding at three years of 0.3%;
15. the method results in a numerical decrease in the ratio of fatal bleeding events over TIMI major bleeding events relative to a dosing regimen where the patient receives the daily maintenance dose of aspirin of 75 mg to 150 mg only;
16. the method results in a numerical decrease in the ratio of fatal bleeding events over TIMI major bleeding events relative to a dosing regimen where the patient receives the daily maintenance dose of aspirin of 75 mg to 150 mg only;
17. the method results in a decrease in the ratio of fatal bleeding events over TIMI major bleeding events relative to a dosing regimen where the patient receives the daily maintenance dose of aspirin of 75 mg to 150 mg only;
18. the method results in a decrease in the ratio of fatal bleeding events over TIMI major bleeding events relative to a dosing regimen where the patient receives the daily maintenance dose of aspirin of 75 mg to 150 mg only;
19. the method results in a numerical decrease of approximately 0.13 in the ratio of fatal bleeding events over TIMI major bleeding events relative to a dosing regimen where the patient receives the daily maintenance dose of aspirin of 75 mg to 150 mg only;
20. the method results in a numerical decrease of 0.13 in the ratio of fatal bleeding events over TIMI major bleeding events relative to a dosing regimen where the patient receives the daily maintenance dose of aspirin of 75 mg to 150 mg only;
21. the method results in a 3-year dyspnea event rate of approximately 15.8%;
22. the method results in a 3-year dyspnea event rate of 15.8%;
23. the method results in a numerical decrease in median duration of resolved dyspnea adverse events relative to a dosing regimen where the patient receives the daily maintenance dose of aspirin of 75 mg to 150 mg only;
24. the method results in a decrease in the median duration of resolved dyspnea adverse events relative to a dosing regimen where the patient receives the daily maintenance dose of aspirin of 75 mg to 150 mg only;
25. the method results in a numerical decrease of approximately 18 days in the median duration of resolved dyspnea adverse events relative to a dosing regimen where the patient receives the daily maintenance dose of aspirin of 75 mg to 150 mg only;
26. the method results in a numerical decrease of 18 days in the median duration of resolved dyspnea adverse events relative to a dosing regimen where the patient receives the daily maintenance dose of aspirin of 75 mg to 150 mg only;
27. the method results in a numerical decrease in median duration of resolved dyspnea adverse events relative to a dosing regimen where the patient receives the daily maintenance dose of aspirin of 75 mg to 150 mg only;
28. the method does not result in a decrease in pulmonary function after one month;
29. the method does not result in a decrease in pulmonary function after at least six months;
30. the method does not result in a hazard ratio greater than one for renal adverse events at 3 years relative to a dosing regimen where the patient receives a daily maintenance dose of aspirin of 75 mg to 150 mg only;
31. the method does not result in a hazard ratio that is nominally significantly greater than one for renal adverse events at 3 years relative to a dosing regimen where the patient receives a daily maintenance dose of aspirin of 75 mg to 150 mg only;
32. the method does not result in a hazard ratio greater than one for gout adverse events at 3 years relative to a dosing regimen where the patient receives a daily maintenance dose of aspirin of 75 mg to 150 mg only;
33. the method does not result in a hazard ratio that is nominally significantly greater than one for gout adverse events at 3 years relative to a dosing regimen where the patient receives a daily maintenance dose of aspirin of 75 mg to 150 mg only;
34. the method does not result in a hazard ratio greater than one for bradyarrhythmia adverse events at 3 years relative to a dosing regimen where the patient receives a daily maintenance dose of aspirin of 75 mg to 150 mg only;
35. the method does not result in a hazard ratio that is nominally significantly greater than one for bradyarrhythmia adverse events at 3 years relative to a dosing regimen where the patient receives a daily maintenance dose of aspirin of 75 mg to 150 mg only;
36. the method results in syncope in approximately 0.9% of patients;
37. the method results in syncope in 0.9% of patients;
38. the method results in a reversible increase in serum uric acid levels;
39. the method results in a serum uric acid level increase of approximately 0.2 mg/dL relative to serum uric acid levels prior to administration;
40. the method results in a numerical increase in the relative risk of TIMI major bleeding of approximately 142% relative to a dosing regimen where the patient receives the daily maintenance dose of aspirin of 75 mg to 150 mg only based on the final dose-exposure-response model;
41. the method results in a numerical increase in the relative risk of TIMI major bleeding of 142% relative to a dosing regimen where the patient receives the daily maintenance dose of aspirin of 75 mg to 150 mg only based on the final dose-exposure-response model;
42. the method results in an absolute risk increase for TIMI major bleeding at three years of approximately 2.38% relative to a dosing regimen where the patient receives the daily maintenance dose of aspirin of 75 mg to 150 mg, wherein the patient is more than 75 years of age;
43. the method results in an absolute risk increase for TIMI major bleeding at three years of approximately 1.05% relative to a dosing regimen where the patient receives the daily maintenance dose of aspirin of 75 mg to 150 mg, wherein the patient is less than 65 years of age;
44. the method results in an absolute risk increase of approximately 1.24% for TIMI major bleeding relative to a dosing regimen where the patient receives the daily maintenance dose of aspirin of 75 mg to 150 mg only;
45. the method results in an absolute risk increase of 1.24% for TIMI major bleeding relative to a dosing regimen where the patient receives the daily maintenance dose of aspirin of 75 mg to 150 mg only;

46. the method results in an absolute risk increase of approximately 0.14% for intracranial hemorrhage relative to a dosing regimen where the patient receives the daily maintenance dose of aspirin of 75 mg to 150 mg only;
47. the method results in an absolute risk increase of 0.14% for intracranial hemorrhage relative to a dosing regimen where the patient receives the daily maintenance dose of aspirin of 75 mg to 150 mg only;
48. the method results in an absolute risk reduction of approximately 0.01% for fatal bleeding relative to a dosing regimen where the patient receives the daily maintenance dose of aspirin of 75 mg to 150 mg only;
49. the method results in an absolute risk reduction of 0.01% for fatal bleeding relative to a dosing regimen where the patient receives the daily maintenance dose of aspirin of 75 mg to 150 mg only;
50. the method results in a TIMI major bleeding number needed to harm of approximately 81 relative to a dosing regimen where the patient receives the daily maintenance dose of aspirin of 75 mg to 150 mg only;
51. the method results in a TIMI major bleeding number needed to harm of 81 relative to a dosing regimen where the patient receives the daily maintenance dose of aspirin of 75 mg to 150 mg only;
52. the method results in an intracranial hemorrhage number needed to harm of approximately 714 relative to a dosing regimen where the patient receives the daily maintenance dose of aspirin of 75 mg to 150 mg only; or
53. the method results in an intracranial hemorrhage number needed to harm of 714 relative to a dosing regimen where the patient receives the daily maintenance dose of aspirin of 75 mg to 150 mg only.

In some embodiments, the disclosed method results in one of the efficacy endpoints recited above. In some further embodiments, the disclosed method results in at least one of the efficacy endpoints recited above. In some further embodiments, the disclosed method results in at least two of the efficacy endpoints recited above. In still some further embodiments, the disclosed method results in two, three, or four of the efficacy endpoints recited above. In some further embodiments, the disclosed methods results in five to 251 of the efficacy endpoints recited above.

In some embodiments, the disclosed method results in one of the safety endpoints recited above. In some further embodiments, the disclosed method results in at least one of the safety endpoints recited above. In some further embodiments, the disclosed method results in at least two of the safety endpoints recited above. In still some further embodiments, the disclosed method results in two, three, or four of the safety endpoints recited above. In some further embodiments, the disclosed methods results in five to 53 of the safety endpoints recited above.

In some embodiments, the disclosed method results in one of the efficacy endpoints recited above and one of the safety endpoints recited above. In some further embodiments, the disclosed method results in at least one of the efficacy endpoints recited above and at least one of the safety endpoints recited above. In still some further embodiments, the disclosed method results in two, three, four, five, or six of the efficacy endpoints recited above and two, three, four, five, or six of the safety endpoints recited above. In some further embodiments, the disclosed method results in one to 251 of the efficacy endpoints recited above and one to 53 of the safety endpoints recited above.

For example, in some embodiments, the method satisfies at least one of the following combined safety and efficacy conditions:

(a) the method numerically reduces the absolute risk of the composite endpoint of cardiovascular death, myocardial infarction, or stroke at three years relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(b) the method results in a relative risk of the composite endpoint of cardiovascular death, myocardial infarction, or stroke of less than one relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(c) the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(d) the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(e) the method results in a relative risk of the composite endpoint of cardiovascular death, myocardial infarction, or stroke that is statistically significantly less than one relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(f) the method results in a Kaplan-Meier rate for the composite endpoint of cardiovascular death, myocardial infarction, or stroke at three years of approximately 7.8% and the method does not result in a hazard ratio for fatal bleeding at 3 years of greater than one relative to a dosing regimen where the patient receives a daily maintenance dose of aspirin of 75 mg to 150 mg only;

(g) the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(h) the method results in a numerical reduction in the percentage of patients with composite endpoint events of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(i) the method results in a hazard ratio for time to first composite endpoint of cardiovascular death, myocardial infarction, or stroke that is statistically significantly less than 1 relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(j) the method results in a hazard ratio for time to first composite endpoint of cardiovascular death, myocardial infarction, or stroke at three years of approximately 0.84 relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(k) the method results in a hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(l) the method results in a 95% confidence interval for the hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(m) the method reduces the absolute risk of the composite endpoint of cardiovascular death, myocardial infarction, or stroke at three years by approximately 1.27% relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(n) the method results in a relative risk reduction of approximately 17% for the composite endpoint of cardiovascular death, myocardial infarction, or stroke at three years relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only;

(o) the method reduces the Kaplan-Meier rate for the composite endpoint of cardiovascular death, myocardial infarction, or stroke at three years by approximately 1.2% compared to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only; or (p) the method reduces the percentage of patients with composite endpoint events of cardiovascular death, myocardial infarction, or stroke at three years by approximately 1.3% relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only.

In some other exemplary embodiments, the method satisfies at least one of the following combined safety and efficacy conditions:

(a) the method numerically reduces the absolute risk of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(b) the method results in a relative risk of the composite endpoint of cardiovascular death, myocardial infarction, or stroke of less than one relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(c) the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(d) the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(e) the method results in a relative risk of the composite endpoint of cardiovascular death, myocardial infarction, or stroke that is statistically significantly less than one relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(f) the method results in a Kaplan-Meier rate for the composite endpoint of cardiovascular death, myocardial infarction, or stroke at three years of approximately 7.8% and the method does not result in a hazard ratio for fatal bleeding at 3 years that is nominally significantly greater than one relative to a dosing regimen where the patient receives a daily maintenance dose of aspirin of 75 mg to 150 mg only;

(g) the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(h) the method results in a numerical reduction in the percentage of patients with composite endpoint events of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(i) the method results in a hazard ratio for time to first composite endpoint of cardiovascular death, myocardial infarction, or stroke that is statistically significantly less than 1 relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(j) the method results in a hazard ratio for time to first composite endpoint of cardiovascular death, myocardial infarction, or stroke at three years of approximately 0.84 relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(k) the method results in a hazard ratio for time to first composite endpoint of cardiovascular death, myocardial infarction, or stroke at 3 years of 0.74 to 0.95 relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(l) the method results in a 95% confidence interval for the hazard ratio for time to first composite endpoint of cardiovascular death, myocardial infarction, or stroke at 3 years of 0.74 to 0.95 relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(m) the method reduces the absolute risk of the composite endpoint of cardiovascular death, myocardial infarction, or stroke at three years by approximately 1.27% relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(n) the method results in a relative risk reduction of approximately 17% for the composite endpoint of cardiovascular death, myocardial infarction, or stroke at three years relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only;

(o) the method reduces the Kaplan-Meier rate for the composite endpoint of cardiovascular death, myocardial infarction, or stroke at three years by approximately 1.2% compared to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only; or (p) the method reduces the percentage of patients with composite endpoint events of cardiovascular death, myocardial infarction, or stroke at 3 years by approximately 1.3% relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only.

In some further exemplary embodiments, the method satisfies at least one of the following combined safety and efficacy conditions:

(a) the method numerically reduces the absolute risk of the composite endpoint of cardiovascular death, myocardial infarction, or stroke relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(b) the method results in a relative risk of the composite endpoint of cardiovascular death, myocardial infarction, or stroke of less than one relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(c) the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(d) the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(e) the method results in a relative risk of the composite endpoint of cardiovascular death, myocardial infarction, or stroke that is statistically significantly less than one relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(f) the method results in a Kaplan-Meier rate for the composite endpoint of cardiovascular death, myocardial infarction, or stroke at three years of approximately 7.8% and the method does not result in a hazard ratio for intracranial hemorrhage at 3 years of greater than one relative to a dosing regimen where the patient receives a daily maintenance dose of aspirin of 75 mg to 150 mg only;

(g) the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(h) the method results in a numerical reduction in the percentage of patients with composite endpoint events of cardiovascular death, myocardial infarction, or stroke relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(i) the method results in a hazard ratio for time to first composite endpoint of cardiovascular death, myocardial infarction, or stroke that is statistically significantly less than 1 relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(j) the method results in a hazard ratio for time to first composite endpoint of cardiovascular death, myocardial infarction, or stroke at 3 years of approximately 0.84 relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(k) the method results in a hazard ratio for time to first composite endpoint of cardiovascular death, myocardial infarction, or stroke at 3 years of 0.74 to 0.95 relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(l) the method results in a 95% confidence interval for the hazard ratio for time to first composite endpoint of cardiovascular death, myocardial infarction, or stroke at 3 years of 0.74 to 0.95 relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(m) the method reduces the absolute risk of the composite endpoint of cardiovascular death, myocardial infarction, or stroke at three years by approximately 1.27% relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(n) the method results in a relative risk reduction of approximately 17% for the composite endpoint of cardiovascular death, myocardial infarction, or stroke at three years relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only;

(o) the method reduces the Kaplan-Meier rate for the composite endpoint of cardiovascular death, myocardial infarction, or stroke at three years by approximately 1.2% compared to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only; or (p) the method reduces the percentage of patients with composite endpoint events of cardiovascular death, myocardial infarction, or stroke at 3 years by approximately 1.3% relative to a dosing regimen where the patient receives the daily maintenance dose of aspirin of 75 mg to 150 mg only and the method does not result in a hazard ratio for intracranial hemorrhage at 3 years of greater than one relative to a dosing regimen where the patient receives a daily maintenance dose of aspirin of 75 mg to 150 mg only.

In some still further exemplary embodiments, the method satisfies at least one of the following combined safety and efficacy conditions:

(a) the method numerically reduces the absolute risk of the composite endpoint of cardiovascular death, myocardial infarction, or stroke relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(b) the method results in a relative risk of the composite endpoint of cardiovascular death, myocardial infarction, or stroke of less than one relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(c) the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(d) the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(e) the method results in a relative risk of the composite endpoint of cardiovascular death, myocardial infarction, or stroke that is statistically significantly less than one relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(f) the method results in a Kaplan-Meier rate for the composite endpoint of cardiovascular death, myocardial infarction, or stroke at three years of approximately 7.8% and the method does not result in a hazard ratio for intracranial hemorrhage at 3 years that is nominally significantly greater than one relative to a dosing regimen where the patient receives a daily maintenance dose of aspirin of 75 mg to 150 mg only;

(g) the method results in a hazard ratio for time to first composite endpoint of cardiovascular death, myocardial infarction, or stroke of less than 1 relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(h) the method results in a numerical reduction in the percentage of patients with composite endpoint events of cardiovascular death, myocardial infarction, or stroke relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(i) the method results in a hazard ratio for time to first composite endpoint of cardiovascular death, myocardial infarction, or stroke that is statistically significantly less than 1 relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(j) the method results in a hazard ratio for time to first composite endpoint of cardiovascular death, myocardial infarction, or stroke at 3 years of approximately 0.84 relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(k) the method results in a hazard ratio for time to first composite endpoint of cardiovascular death, myocardial infarction, or stroke at 3 years of 0.74 to 0.95 relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(l) the method results in a 95% confidence interval for the hazard ratio for time to first composite endpoint of cardiovascular death, myocardial infarction, or stroke at 3 years of 0.74 to 0.95 relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(m) the method reduces the absolute risk of the composite endpoint of cardiovascular death, myocardial infarction, or stroke at three years by approximately 1.27% relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(n) the method results in a relative risk reduction of approximately 17% for the composite endpoint of cardiovascular death, myocardial infarction, or stroke at three years relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only;

(o) the method reduces the Kaplan-Meier rate for the composite endpoint of cardiovascular death, myocardial infarction, or stroke at three years by approximately 1.2% compared to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only; or (p) the method reduces the percentage of patients with composite endpoint events of cardiovascular death, myocardial infarction, or stroke at 3 years by approximately 1.3% relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only.

In some embodiments, the method results in a numerical reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only.

In some embodiments, the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only.

In some embodiments, the method results in a numerical reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only.

In some embodiments, the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years of greater than one relative to a dosing regimen where the patient receives a daily maintenance dose of aspirin of 75 mg to 150 mg only.

In some embodiments, the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for fatal bleeding at 3 years that is nominally significantly greater than one relative to a dosing regimen where the patient receives a daily maintenance dose of aspirin of 75 mg to 150 mg only.

In some embodiments, the method results in a statistically significant reduction in the rate of the composite endpoint of cardiovascular death, myocardial infarction, or stroke relative to a dosing regimen where the patient receives the daily maintenance dose of aspirin of 75 mg to 150 mg only and the method does not result in a hazard ratio for intracranial hemorrhage at 3 years that is nominally significantly greater than one relative to a dosing regimen where the patient receives a daily maintenance dose of aspirin of 75 mg to 150 mg only.

What is claimed is:

1. A method for reducing the rate of a composite endpoint of cardiovascular death, myocardial infarction, or stroke in a patient in recognized need thereof, comprising administering to the patient twice daily a pharmaceutical composition comprising 60 mg ticagrelor and a pharmaceutically acceptable carrier;
   wherein the patient has a history of myocardial infarction;
   wherein the patient is also administered a daily maintenance dose of aspirin of 75 mg to 150 mg; and
   wherein the rate of the composite endpoint in the patient is reduced relative to a dosing regimen where the patient receives the daily maintenance dose of aspirin of 75 mg to 150 mg only.

2. The method of claim 1, wherein the daily maintenance dose of aspirin is 75 mg to 100 mg.

3. The method of claim 1, wherein the patient has a history of myocardial infarction at least 12 months prior to the twice daily administration of the pharmaceutical composition comprising 60 mg ticagrelor and a pharmaceutically acceptable carrier.

4. The method of claim 1, wherein the patient has a history of myocardial infarction 12 to 36 months prior to the twice daily administration of the pharmaceutical composition comprising 60 mg ticagrelor and a pharmaceutically acceptable carrier.

5. The method of claim 1, wherein the patient has a history of myocardial infarction as a result of an acute coronary syndrome.

6. The method of claim 5, wherein prior to the administration, the patient was administered twice daily a pharmaceutical composition comprising 90 mg ticagrelor and a pharmaceutically acceptable carrier for a portion of 12 months after the acute coronary syndrome.

7. The method of claim 5, wherein prior to the administration, the patient was administered twice daily a pharmaceutical composition comprising 90 mg ticagrelor and a pharmaceutically acceptable carrier for 12 months after the acute coronary syndrome.

8. The method of claim 6, wherein the patient was administered a pharmaceutical composition comprising a 180 mg ticagrelor loading dose prior to administration twice daily of a pharmaceutical composition comprising 90 mg ticagrelor and a pharmaceutically acceptable carrier for a portion of the 12 months after the acute coronary syndrome.

9. The method of claim 1, wherein the method satisfies at least one of the following conditions:
   (a) the method numerically reduces the absolute risk of the composite endpoint of cardiovascular death, myocardial infarction, or stroke relative to a dosing regimen where the patient receives the daily maintenance dose of aspirin of 75 mg to 150 mg only;
   (b) the method results in a relative risk of the composite endpoint of cardiovascular death, myocardial infarction, or stroke of less than one relative to a dosing regimen where the patient receives the daily maintenance dose of aspirin of 75 mg to 150 mg only;
   (c) the method numerically reduces the Kaplan-Meier rate for the composite endpoint of cardiovascular death, myocardial infarction, or stroke compared to a dosing regimen where the patient receives the daily maintenance dose of aspirin of 75 mg to 150 mg only;
   (d) the method results in a statistically significant reduction in the rate of the composite endpoint of cardiovascular death, myocardial infarction, or stroke relative to a dosing regimen where the patient receives the daily maintenance dose of aspirin of 75 mg to 150 mg only;
   (e) the method results in a relative risk of the composite endpoint of cardiovascular death, myocardial infarction, or stroke that is statistically significantly less than one relative to a dosing regimen where the patient receives the daily maintenance dose of aspirin of 75 mg to 150 mg only;
   (f) the method results in a Kaplan-Meier rate for the composite endpoint of cardiovascular death, myocardial infarction, or stroke at three years of approximately 7.8%;
   (g) the method results in a hazard ratio for time to first composite endpoint of cardiovascular death, myocardial infarction, or stroke of less than one relative to a dosing regimen where the patient receives the daily maintenance dose of aspirin of 75 mg to 150 mg only;

(h) the method results in a numerical reduction in the percentage of patients with composite endpoint events of cardiovascular death, myocardial infarction, or stroke relative to a dosing regimen where the patient receives the daily maintenance dose of aspirin of 75 mg to 150 mg only;

(i) the method results in a hazard ratio for time to first composite endpoint of cardiovascular death, myocardial infarction, or stroke that is statistically significantly less than one relative to a dosing regimen where the patient receives the daily maintenance dose of aspirin of 75 mg to 150 mg only;

(j) the method results in a hazard ratio for time to first composite endpoint of cardiovascular death, myocardial infarction, or stroke at three years of approximately 0.84 relative to a dosing regimen where the patient receives the daily maintenance dose of aspirin of 75 mg to 150 mg only;

(k) the method results in a hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only;

(l) the method results in a 95% confidence interval for the hazard ratio for time to first composite endpoint of cardiovascular death, myocardial infarction, or stroke at three years of 0.74 to 0.95 relative to a dosing regimen where the patient receives the daily maintenance dose of aspirin of 75 mg to 150 mg only;

(m) the method reduces the absolute risk of the composite endpoint of cardiovascular death, myocardial infarction, or stroke at three years by approximately 1.27% relative to a dosing regimen where the patient receives the daily maintenance dose of aspirin of 75 mg to 150 mg only;

(n) the method results in a relative risk reduction of approximately 17% for the composite endpoint of cardiovascular death, myocardial infarction, or stroke at three years relative to a dosing regimen where the patient receives the daily maintenance dose of aspirin of 75 mg to 150 mg only;

(o) the method reduces the Kaplan-Meier rate for the composite endpoint of cardiovascular death, myocardial infarction, or stroke at three years by approximately 1.2% compared to a dosing regimen where the patient receives the daily maintenance dose of aspirin of 75 mg to 150 mg only;

(p) the method reduces the percentage of patients with composite endpoint events of cardiovascular death, myocardial infarction, or stroke at three years by approximately 1.3% relative to a dosing regimen where the patient receives the daily maintenance dose of aspirin of 75 mg to 150 mg only;

(q) the method results in a numerical reduction in the rare of the cardiovascular death relative to a dosing regimen where the patient receives the daily maintenance dose of aspirin of 75 mg to 150 mg only; or (r) the method results in a numerical reduction in the rate of the all-cause mortality relative to a dosing regimen where the patient receives the daily maintenance dose of aspirin of 75 mg to 150 mg only.

10. The method of claim 1, wherein the method satisfies at least one of the following conditions:

(a) the method does not result in a hazard ratio for fatal bleeding at 3 years of greater than one relative to a dosing regimen where the patient receives a daily maintenance dose of aspirin of 75 mg to 150 mg only;

(b) the method does not result in a hazard ratio for fatal bleeding at 3 years that is nominally significantly greater than one relative to a dosing regimen where the patient receives a daily maintenance dose of aspirin of 75 mg to 150 mg only;

(c) the method does not result in a hazard ratio for intracranial hemorrhage at 3 years of greater than one relative to a dosing regimen where the patient receives a daily maintenance dose of aspirin of 75 mg to 150 mg only;

(d) the method does not result in a hazard ratio for intracranial hemorrhage at 3 years that is nominally significantly greater than one relative to a dosing regimen where the patient receives a daily maintenance dose of aspirin of 75 mg to 150 mg only;

(e) the method does not result in a relative risk for fatal bleeding at 3 years of greater than one relative to a dosing regimen where the patient receives a daily maintenance dose of aspirin of 75 mg to 150 mg only;

(f) the method does not result in a relative risk for fatal bleeding at 3 years that is nominally significantly greater than one relative to a dosing regimen where the patient receives a daily maintenance dose of aspirin of 75 mg to 150 mg only;

(g) the method does not result in a relative risk for intracranial hemorrhage at 3 years of greater than one relative to a dosing regimen where the patient receives a daily maintenance dose of aspirin of 75 mg to 150 mg only;

(h) the method does not result in a relative risk for intracranial hemorrhage at 3 years that is nominally significantly greater than one relative to a dosing regimen where the patient receives a daily maintenance dose of aspirin of 75 mg to 150 mg only;

(i) the method results in a numerical increase in the number of TIMI major bleeding events per 100 patient years of less than 0.5 relative to a dosing regimen where the patient receives the daily maintenance dose of aspirin of 75 mg to 150 mg only;

(j) the method results in a numerical increase in the number of TIMI major bleeding events per 100 patient years of approximately 0.44 relative to a dosing regimen where the patient receives the daily maintenance dose of aspirin of 75 mg to 150 mg only;

(k) the method does not result in a numerical increase in the number of fatal bleeding events per 100 patient years relative to a dosing regimen where the patient receives the daily maintenance dose of aspirin of 75 mg to 150 mg only;

(l) the method results in a numerical increase in the number of intracranial hemorrhage events per 100 patient years of approximately 0.05 relative to a dosing regimen where the patient receives the daily maintenance dose of aspirin of 75 mg to 150 mg only;

(m) the method results in a difference in the Kaplan-Meier rate of fatal bleeding at three years of less than 0.05% relative to a dosing regimen where the patient receives the daily maintenance dose of aspirin of 75 mg to 150 mg only; or (n) the method results in a difference in the Kaplan-Meier rate of intracranial hemorrhage at three years of less than 0.1% relative to a dosing regimen where the patient receives the daily maintenance dose of aspirin of 75 mg to 150 mg only.

11. The method of claim 1, wherein the method satisfies at least the following conditions:
   the method results in a statistically significant reduction in the rate of the composite endpoint of cardiovascular death, myocardial infarction, or stroke relative to a dosing regimen where the patient receives the daily maintenance dose of aspirin of 75 mg to 150 mg only; and
   the method does not result in a hazard ratio for fatal bleeding at 3 years of greater than one relative to a dosing regimen where the patient receives a daily maintenance dose of aspirin of 75 mg to 150 mg only.

12. The method of claim 1, wherein the method satisfies at least the following conditions:
   the method results in a statistically significant reduction in the rate of the composite endpoint of cardiovascular death, myocardial infarction, or stroke relative to a dosing regimen where the patient receives the daily maintenance dose of aspirin of 75 mg to 150 mg only; and
   the method does not result in a hazard ratio for fatal bleeding at 3 years that is nominally significantly greater than one relative to a dosing regimen where the patient receives a daily maintenance dose of aspirin of 75 mg to 150 mg only.

13. The method of claim 1, wherein the method satisfies at least the following conditions:
   the method results in a statistically significant reduction in the rate of the composite endpoint of cardiovascular death, myocardial infarction, or stroke relative to a dosing regimen where the patient receives the daily maintenance dose of aspirin of 75 mg to 150 mg only; and
   the method does not result in a hazard ratio for intracranial hemorrhage at 3 years of greater than one relative to a dosing regimen where the patient receives a daily maintenance dose of aspirin of 75 mg to 150 mg only.

14. The method of claim 1, wherein the method satisfies at least the following conditions:
   the method results in a statistically significant reduction in the rate of the composite endpoint of cardiovascular death, myocardial infarction, or stroke relative to a dosing regimen where the patient receives the daily maintenance dose of aspirin of 75 mg to 150 mg only; and
   the method does not result in a hazard ratio for intracranial hemorrhage at 3 years that is nominally significantly greater than one relative to a dosing regimen where the patient receives a daily maintenance dose of aspirin of 75 mg to 150 mg only.

15. The method of claim 1; wherein the method satisfies at least the following conditions:
   the method results in a statistically significant reduction in the rate of the composite endpoint of cardiovascular death, myocardial infarction, or stroke relative to a dosing regimen where the patient receives the daily maintenance dose of aspirin of 75 mg to 150 mg only; and
   the method does not result in a relative risk for fatal bleeding at 3 years of greater than one relative to a dosing regimen where the patient receives a daily maintenance dose of aspirin of 75 mg to 150 mg only.

16. The method of claim 1, wherein the pharmaceutical composition comprising 60 mg ticagrelor and a pharmaceutically acceptable carrier is a tablet administered orally.

17. The method of claim 16, wherein the tablet comprises a filler present in an amount of 20 to 70% by weight, a binder present in an amount of 3 to 6% by weight, a disintegrant present in an amount of 2 to 6% by weight, and a lubricant present in an amount of 0.5 to 1% by weight.

18. A method for reducing the rate of a composite endpoint of cardiovascular death, myocardial infarction, or stroke in a patient in recognized need thereof, comprising administering to the patient twice daily a pharmaceutical composition comprising 60 mg ticagrelor and a pharmaceutically acceptable carrier;
   wherein the patient has or had acute coronary syndrome;
   wherein the patient is also administered a daily maintenance dose of aspirin of 75 mg to 150 mg; and
   wherein the rate of the composite endpoint in the patient is reduced relative to a dosing regimen where the patient receives the daily maintenance dose of aspirin of 75 mg to 150 mg only.

19. The method of claim 18, wherein the patient has acute coronary syndrome.

20. The method of claim 18, wherein the daily maintenance dose of aspirin is 75 mg to 100 mg.

21. The method of claim 7, wherein the patient was administered a pharmaceutical composition comprising a 180 mg ticagrelor loading dose prior to administration twice daily of a pharmaceutical composition comprising 90 mg ticagrelor and a pharmaceutically acceptable carrier for a portion of the 12 months after the acute coronary syndrome.

* * * * *